United States Patent
Abbot et al.

(10) Patent No.: US 11,512,282 B2
(45) Date of Patent: Nov. 29, 2022

(54) ENHANCED PLACENTAL STEM CELLS AND USES THEREOF

(71) Applicant: Celularity Inc., Florham Park, NJ (US)

(72) Inventors: Stewart Abbot, San Diego, CA (US); Katarzyna Karasiewicz-Mendez, Hillsborough, NJ (US); Robert J Hariri, Bernardsville, NJ (US); Xiaokui Zhang, Martinsville, NJ (US)

(73) Assignee: Celularity Inc., Florham Park, NJ (US)

( * ) Notice: Subject to any disclaimer, the term of this patent is extended or adjusted under 35 U.S.C. 154(b) by 0 days.

(21) Appl. No.: 16/384,857

(22) Filed: Apr. 15, 2019

(65) Prior Publication Data

US 2021/0238544 A1    Aug. 5, 2021

Related U.S. Application Data

(63) Continuation of application No. 14/774,250, filed as application No. PCT/US2014/025202 on Mar. 13, 2014, now Pat. No. 10,329,529.

(60) Provisional application No. 61/785,222, filed on Mar. 14, 2013.

(51) Int. Cl.
```
C12N 5/073      (2010.01)
C12N 15/11      (2006.01)
C12N 15/113     (2010.01)
A61K 35/50      (2015.01)
```

(52) U.S. Cl.
CPC ............ C12N 5/0605 (2013.01); A61K 35/50 (2013.01); C12N 15/111 (2013.01); C12N 15/113 (2013.01); C12N 2310/141 (2013.01); C12N 2501/65 (2013.01)

(58) Field of Classification Search
CPC .................... C12N 2501/65; C12N 5/0605
USPC ................................................ 435/375, 377
See application file for complete search history.

(56) References Cited

U.S. PATENT DOCUMENTS

2006/0099194 A1   5/2006  Geng
2012/0230959 A1*  9/2012  Abbot ............... A61K 31/7088
                                                    424/93.7

FOREIGN PATENT DOCUMENTS

WO    2005001076    1/2005
WO    2014093753    6/2014

OTHER PUBLICATIONS

Wang et al. (Bcl2 Enhances Induced Hematopoietic Differentiation of Murine Embryonic Stem Cells' (Experimental Hematology, Feb. 2008, vol. 36, No. 2, pp. 128-139; hereinafter'Wang') (Year: 2008).*
Yaping Wang et al, "miR-16 inhibits the proliferation and angiogenesis-regulating potential of mesenchymal stem cells in severe pre-eclampsia", FEBS Journal, GB, (Nov. 22, 2012), vol. 279, No. 24, doi:10.1111/febs.12037, ISSN 1742-464X, pp. 4510-4524, XP055310688.
Sheng-Hua Zhou, "Mesenchymal stem cells modified with miR-126 release angiogenic factors and activate Notch ligand Delta-like-4, enhancing ischemic angiogenesis and cell survival", International Journal of Molecular Medicine, GR, (Dec. 3, 2012), doi:10.3892/ijmm.2012.1200, ISSN 1107-3756, XP055310694.
Yu Nie et al, "Identification of MicroRNAs Involved in Hypoxia- and Serum Deprivation-Induced Apoptosis in Mesenchymal Stem Cells", International Journal of Biological Sciences, (Jan. 1, 2011), doi:10.7150/ijbs.7.762, ISSN 1449-2288, pp. 762-768, XP055204995.
Alexander Rudov et al, "Involvement of miRNAs in Placental Alterations Mediated by Oxidative Stress", Oxidative Medicine and Cellular Longevity, US, (Jan. 1, 2014), vol. 19, No. 1-2, doi:10.1095/biolreprod.108.075481, ISSN 1942-0900, pp. 544-547, XP055310691.
Wang, YY et al., "Bcl2 Enhances Induced Hematopoietic Differentiation of Murine Embryonic Stem Cells.", Experimental Hematology, (Nov. 26, 2008), vol. 36, No. 2, doi:10.1016/J.EXPHEM.2007.09.004, pp. 128-139, XP022425429.

* cited by examiner

Primary Examiner — Janet L Epps-Smith
(74) Attorney, Agent, or Firm — Geoffry T. Knudsen

(57) ABSTRACT

Provided herein are placental stem cells that exhibit increased survival ("enhanced placental stem cells"), compositions comprising such placental stem cells, and methods of using such placental stem cells and compositions.

15 Claims, 11 Drawing Sheets

Specification includes a Sequence Listing.

ENHANCED PLACENTAL STEM CELLS AND USES THEREOF

This application is a continuation of U.S. patent application Ser. No. 14/774,250, filed Sep. 10, 2015 which is a national stage entry of International Patent Application No. PCT/US2014/025202, filed Mar. 13, 2014, which claims priority to U.S. Provisional Patent Application No. 61/785,222, filed Mar. 14, 2013, the disclosures of which are incorporated herein by reference in their entireties.

The Sequence Listing for this application was submitted via EFS Web as a file named "16384857.txt" which was created on Feb. 10, 2020. The file is 1.45 KB. The entire contents of this file is incorporated herein by reference in its entirety.

1. FIELD

Provided herein are placental stem cells that exhibit increased survival ("enhanced placental stem cells"), compositions comprising such placental stem cells, and methods of using such placental stem cells and compositions.

2. BACKGROUND

Because mammalian placentas are plentiful and are normally discarded as medical waste, they represent a unique source of medically-useful cells, e.g., placental stem cells. When cultured/present in certain environments, e.g., in vivo, cells can exhibit decreased survival due to the presence of environmental factors that act as insults to the cells. There exists a need for populations of placental stem cells that are resistant to such insults, and thus survive for longer periods of time in environments that would normally cause cell survival to diminish.

3. SUMMARY

In one aspect, provided herein is a method of modifying placental stem cells such that the placental stem cells survive for longer durations of time under certain conditions as compared to corresponding unmodified placental stem cells, e.g., modifying the cells to make them resistant to conditions that lead to cell death. Such modified placental stem cells are herein termed "enhanced placental stem cells." The enhanced placental stem cells provided herein demonstrate increased survival, and thus can advantageously be used in therapy, particularly in therapy where the placental stem cells are exposed to conditions that can lead to cell death, e.g., exposure to host cells, blood and blood components (e.g., serum, antibodies, complement) and other conditions that cause or contribute to cell death. In another aspect, presented herein are enhanced placental stem cells and pharmaceutical compositions comprising enhanced placental stem cells.

In certain embodiments, placental stem cells modified in accordance with the methods described herein are considered enhanced placental stem cells if they are capable of surviving when exposed to a given condition for a longer duration of time than corresponding unmodified placental stem cells exposed to the same condition. For example, in one embodiment, an enhanced placental stem cell demonstrates increased survival in the presence of serum (e.g., human or rat serum), complement, antibody(ies), other cells (e.g., cells of the immune system), or conditions that can lead to anoikis (e.g., low-attachment conditions) as compared to corresponding unmodified placental stem cells.

Corresponding unmodified placental stem cells, as used herein, can include any placental stem cell, or population thereof, having the same characteristics of the placental stem cell or population thereof used to generate the enhanced placental stem cells to which the corresponding unmodified placental stem cells are compared to. For example, corresponding unmodified placental stem cells can possess any of the physical and/or morphological characteristics of placental stem cells described in Section 5.3.1, below, and/or can possess any of the cell surface, molecular, and/or genetic markers of placental stem cells described in Section 5.3.2, below. In certain embodiments, corresponding unmodified placental stem cells, when compared to enhanced placental stem cells (i.e., placental stem cells modified in accordance with the methods described herein) are the same as the enhanced placental stem cells with respect to physical, morphological, and/or genetic makeup except for the fact that the corresponding unmodified placental stem cells have not been modified in accordance with the methods described herein.

In certain embodiments, placental stem cells modified in accordance with the methods described herein are considered enhanced placental stem cells if they demonstrate one or more of (i) decreased caspase 3/7 activity, (ii) increased mitochondrial membrane potential, and/or (iii) increased metabolic activity when exposed to a given condition as compared to corresponding unmodified placental stem cells exposed to the same condition. In a specific embodiment, enhanced placental stem cells demonstrate decreased caspase 3/7 activity, increased mitochondrial membrane potential, and increased metabolic activity when exposed to a given condition as compared to corresponding unmodified placental stem cells exposed to the same condition. Methods and kits for assaying caspase 3/7 activity are known in the art, e.g., the Caspase-Glo® 3/7 Assay System (Promega). Also known in the art are assays and kits for measuring cellular metabolic activity (e.g., Cell Titer Glo Kit (Promega), ATP Determination Kit (Life Technologies), and Amplex® Red Glutamic Acid/Glutamate Oxidase Assay Kit (Life Technologies)) and assays and kits for measuring mitochondrial membrane potential (e.g., TMRE—Mitochondrial Membrane Potential Assay Kit (Abcam). Such methods and kits also are described herein (see Sections 6.1.1.1.3 and 6.1.1.1.2, below).

In certain embodiments, placental stem cells modified in accordance with the methods described herein are considered enhanced placental stem cells if they enter a quiescent state when exposed to a condition known to cause cell death of the placental stem cell, e.g., culturing of the placental stem cells in serum (e.g., rat serum).

In one embodiment, provided herein is a method of generating enhanced placental stem cells, comprising contacting a population of placental stem cells with an effective amount of oligomeric or polymeric molecules, such that one or more genes associated with survival of the placental stem cells is inhibited (e.g., downregulated as compared to placental stem cells that have not been modified, e.g., that have not been contacted with said molecules). In another embodiment, provided herein is a method of generating enhanced placental stem cells, comprising contacting a population of placental stem cells with an effective amount of oligomeric or polymeric molecules, such that one or more genes associated with survival of the placental stem cells is upregulated (e.g., upregulated as compared to placental stem cells that have not been modified, e.g., that have not been contacted with said molecules). In certain embodiments, said oligomeric or polymeric molecules are nucleic acid molecules, such as modulatory RNA molecules. In specific embodiments, the modulatory RNA molecules are microRNAs, microRNA mimics, small interfering RNAs (siRNAs), antisense RNAs, antisense DNAs, small hairpin RNAs (shRNAs), microRNA-adapted shRNA (shRNAmirs), or any combination thereof.

In certain embodiments, the oligomeric or polymeric molecules, e.g., modulatory RNA molecules, used in the methods described herein for generating enhanced placental stem cells target one or more placental stem cell genes identified herein as being associated with augmentation of placental stem cell survival under suboptimal conditions (herein termed "survival-associated genes"). For example, the oligomeric or polymeric molecules, e.g., modulatory RNA molecules, target said one or more placental stem cell genes as a result of having an RNA or DNA sequence that is complementary to a nucleic acid or amino acid sequence of said one or more placental stem cell genes. In certain embodiments, inhibition or upregulation of such survival-associated genes in placental stem cells results in an increased ability of the placental stem cells to survive in the presence of one or more conditions that would otherwise cause death of the placental stem cells. In certain embodiments, inhibition or upregulation of such survival-associated genes in placental stem cells results in the ability of the placental stem cells to survive in the presence of one or more conditions that would otherwise cause death of the placental stem cells for a longer duration of time than corresponding unmodified placental stem cells in the presence of the same condition(s). In certain embodiments, inhibition or upregulation of such survival-associated genes in placental stem cells results in (i) decreased caspase 3/7 activity, (ii) increased mitochondrial membrane potential, and/or (iii) increased metabolic activity of the placental stem cells when exposed to a given condition as compared to corresponding unmodified placental stem cells exposed to the same condition. In certain embodiments, inhibition or upregulation of such survival-associated genes in placental stem cells results in entry of the placental stem cells into a quiescent state when exposed to a condition or conditions known to cause cell death of the placental stem cell. In a specific embodiment, said one or more survival-associated genes targeted in the methods described herein to produce enhanced placental stem cells comprise one or more of the genes listed in Table 1, below:

TABLE 1

SURVIVAL-ASSOCIATED GENES
(Number in parentheses is the NCBI GENE ID NUMBER)

| | | | | | |
|---|---|---|---|---|---|
| ADAMTS9 (56999) | ABCF2 (1061) | DNAJB4 (11080) | MYB (4602) | RTN4 (57142) | ANLN (54443) |
| BACE1 (23621) | ABHD10 (55347) | EGFR (1956) | NAA15 (80155) | SEC24A (10802) | MAP2K1 (5604) |
| BCL2 (596) | ACTR1A (10121) | EIF4E (1977) | NAA25 (80018) | SHOC2 (8036) | CCNF (899) |
| CAV2 (858) | ACVR2A (92) | EPT1 (85465) | NAPG (8774) | SLC12A2 (6558) | CDC14A (8556) |
| CD276 (80381) | ADSS (159) | FGF2 (2247) | NOB1 (28987) | SLC16A3 (9123) | CDC25A (993) |
| CDC42 (998) | ALG3 (10195) | FNDC3B (64778) | NOTCH2 (4853) | SLC25A22 (79751) | CHEK1 (1111) |
| CDK6 (1021) | ARHGDIA (396) | GALNT7 (51809) | PAFAH1B2 (5049) | SLC38A5 (92745) | CUL2 (8453) |
| COL3A1 (1281) | ARL2 (402) | GPAM (57678) | PDCD4 (27250) | SLC7A1 (6541) | FGFR1 (2260) |
| COL4A1 (1282) | ATG9A (79065) | HACE1 (57531) | PDCD6IP (10015) | SNX15 (29907) | ITPR1 (3708) |
| COL4A2 (1284) | PLAG1 (5324) | HARS (3035) | PHKB (5257) | SPTLC1 (10558) | KIF23 (9493) |
| CPEB3 (22849) | C9ORF167/TOR4A (54863) | HARS2 (23438) | PISD (23761) | SQSTM1 (8878) | TRIM63 (84676) |
| CXXC6/TET1 (80312) | C9ORF89 (84270) | HERC6 (55008) | PLK1 (5347) | SRPR (6734) | CSHL1 (1444) |
| DIABLO (56616) | CACNA2D1 (781) | HMGA1 (3159) | PNN (5411) | SRPRB (58477) | WEE1 (7465) |
| DNMT3A (1788) | CAPRIN1 (4076) | HSDL2 (84263) | PNPLA6 (10908) | TMEM43 (79188) | MLLT1 (4298) |
| DNMT3B (3) | CCDC109A/MCU (90550) | IGF2R (3482) | PPIF (10105) | TNFSF9 (8744) | MMS19 (64210) |
| FGA (2243) | CCND1 (595) | IPO4 (79711) | SIAH1 (6477) | TOMM34 (10953) | RECK (8434) |
| IMPDH1 (3614) | CCND3 (896) | ITGA2 (3673) | PPP2R5C (5527) | TPM3 (7170) | RNASEL (6041) |
| INSIG1 (3638) | CCNE1 (898) | KCNN4 (3783) | PSAT1 (29968) | TPPP3 (51673) | WT1 (7490) |
| KREMEN2 (79412) | CCNT2 (905) | KPNA3 (3839) | PTCD3 (55037) | UBE2V1 (7335) | YIF1B (90522) |
| LPL (4023) | CDC14B (8555) | LAMC1 (3915) | PTGS2 (5743) | UBE4A (9354) | ZNF622 (90441) |
| MCL1 (4170) | CDK5RAP1 (51654) | LAMTOR3 (8649) | PURA (5813) | UGDH (7358) | |
| PIK3R1 (5295) | CENPJ (55835) | LUZP1 (7798) | RAB9B (51209) | UTP15 (84135) | |

TABLE 1-continued

SURVIVAL-ASSOCIATED GENES
(Number in parentheses is the NCBI GENE ID NUMBER)

| | | | | |
|---|---|---|---|---|
| PPM1D (8493) | CHORDC1 (26973) | LYPLA2 (11313) | RAD51C (5889) | VEGFA (7422) |
| SPARC (6678) | CREBL2 (1389) | PIAS1 (8554) | RARS (6097) | WNT3A (89780) |

In one embodiment, the modulatory RNA molecules used in the methods described herein for generating enhanced placental stem cells are microRNAs (miRNAs). In a specific embodiment, said miRNAs target one or more (e.g., a combination) of the genes listed in Table 1, above. In another specific embodiment, said miRNAs target at least two, at least 3, at least 4, or at least 5 of the genes listed in Table 1, above. In another specific embodiment, said miRNAs are double-stranded, wherein one strand of said miRNAs have a sequence at least about 70%, 80%, 90%, 95%, 98% or 100% complementary to the sequence of one of the genes identified in Table 1, above (as identified based on the Gene ID of the gene provided in the table).

In another specific embodiment, a microRNA used to generate enhanced placental stem cells in accordance with the methods described herein includes a microRNA listed in Table 2, below. In another specific embodiment, a combination (two or more) of the microRNA listed in Table 2, below, are used to generate enhanced placental stem cells in accordance with the methods described herein. In another specific embodiment, the microRNA used to generate enhanced placental stem cells in accordance with the methods described herein is miR-16, miR-29a, miR-424, miR-4305, miR-3142, or miR-613. In another specific embodiment, the microRNA used to generate enhanced placental stem cells in accordance with the methods described herein are a combination of two or more of miR-16, miR-29a, miR-424, miR-4305, miR-3142, and/or miR-613. In another specific embodiment, the microRNA used to generate enhanced placental stem cells in accordance with the methods described herein is miR-16. In another specific embodiment, the microRNA used to generate enhanced placental stem cells in accordance with the methods described herein is miR-29a. In another specific embodiment, the microRNA used to generate enhanced placental stem cells in accordance with the methods described herein is miR-424.

enhanced placental stem cells target the placental stem cell survival-associated gene CCND1. In another specific embodiment, the miRNAs or miRNA mimics used in the methods described herein for generating enhanced placental stem cells target the placental stem cell survival-associated gene CCND3. In another specific embodiment, the miRNAs or miRNA mimics used in the methods described herein for generating enhanced placental stem cells target the placental stem cell survival-associated gene CCNE1. In another specific embodiment, the miRNAs or miRNA mimics used in the methods described herein for generating enhanced placental stem cells target the placental stem cell survival-associated gene CCNF. In another specific embodiment, the miRNAs or miRNA mimics used in the methods described herein for generating enhanced placental stem cells target the placental stem cell survival-associated gene CDK6. In another specific embodiment, the miRNAs or miRNA mimics used in the methods described herein for generating enhanced placental stem cells target the placental stem cell survival-associated gene PPP2R5C. In another specific embodiment, the miRNAs or miRNA mimics used in the methods described herein for generating enhanced placental stem cells target the placental stem cell survival-associated gene CDC25A. In another specific embodiment, the miRNAs or miRNA mimics used in the methods described herein for generating enhanced placental stem cells target the placental stem cell survival-associated gene WEE1. In another specific embodiment, the miRNAs or miRNA mimics used in the methods described herein for generating enhanced placental stem cells target the placental stem cell survival-associated gene CHEK1. In another specific embodiment, the miRNAs or miRNA mimics used in the methods described herein for generating enhanced placental stem cells target the placental stem cell survival-associated gene MCL1. In another specific embodiment, the miRNAs or miRNA mimics used in the methods described herein for

TABLE 2

| microRNA | | | | | |
|---|---|---|---|---|---|
| hsa-miR-424 | hsa-miR-141 | hsa-miR-3142 | hsa-miR-4310 | hsa-miR-1826 | hsa-miR-1308 |
| hsa-miR-143 | hsa-miR-581 | hsa-miR-1201 | hsa-miR-1203 | hsa-miR-3158 | hsa-miR-1227 |
| hsa-miR-136 | hsa-miR-362-5p | hsa-miR-4305 | hsa-miR-1271 | hsa-miR-1236 | hsa-miR-369-5p |
| hsa-miR-662 | hsa-miR-613 | hsa-miR-126* | hsa-miR-3123 | hsa-miR-432 | hsa-miR-450b-5p |
| hsa-miR-432* | hsa-miR-611 | hsa-miR-591 | hsa-miR-631 | hsa-miR-3170 | hsa-miR-548k |
| hsa-miR-16 | hsa-miR-199a-5p | hsa-miR-521 | hsa-miR-301a | hsa-miR-514b-5p | hsa-miR-29a |

In another embodiment, the modulatory RNA molecules used in the methods described herein for generating enhanced placental stem cells are microRNA mimics (miRNA mimics). In a specific embodiment, said miRNA mimics target one or more (e.g., a combination) of the genes listed in Table 1, above. In another specific embodiment, said miRNA mimics are based on one or more of the microRNAs listed in Table 2, above.

In another specific embodiment, the miRNAs or miRNA mimics used in the methods described herein for generating generating enhanced placental stem cells target the placental stem cell survival-associated gene BCL2. In another specific embodiment, the miRNAs or miRNA mimics used in the methods described herein for generating enhanced placental stem cells target the placental stem cell survival-associated gene PPMID. In another specific embodiment, the miRNAs or miRNA mimics used in the methods described herein for generating enhanced placental stem cells target the placental stem cell survival-associated gene HMGA1. In another specific embodiment, the miRNAs or miRNA mimics used in the methods described herein for generating enhanced placental stem cells target the placental stem cell survival-associated gene AKT3. In another specific embodiment, the miRNAs or miRNA mimics used in the methods described herein for generating enhanced placental stem cells target the placental stem cell survival-associated gene VEGFA. In another specific embodiment, the miRNAs or miRNA mimics used in the methods described herein for generating enhanced placental stem cells target the placental stem cell survival-associated gene MYB. In another specific embodiment, the miRNAs or miRNA mimics used in the methods described herein for generating enhanced placental stem cells target the placental stem cell survival-associated gene ITGA2.

In another specific embodiment, the miRNAs or miRNA mimics used in the methods described herein for generating enhanced placental stem cells target two, three, or more (i.e., a combination) of the following placental stem cell survival-associated genes: CCND1, CCND3, CCNE1, CCNF, CDK6, PPP2R5C, CDC25A, WEE1, CHEK1, MCL1, BCL2, PPMID, HMGA1, AKT3, VEGFA, MYB, and/or ITGA2. In another specific embodiment, the miRNAs or miRNA mimics used in the methods described herein for generating enhanced placental stem cells target two, three, or more (i.e., a combination) of the following placental stem cell survival-associated genes: CCND1, CCND3, CCNE1, CCNF, CDK6, CDC25A, WEE1, CHEK1, and/or MYB. In another specific embodiment, the miRNAs or miRNA mimics used in the methods described herein for generating enhanced placental stem cells target two, three, or more (i.e., a combination) of the following placental stem cell survival-associated genes: MCL1, PPMID, HMGA1, AKT3, VEGFA, and/or ITGA2.

In another embodiment, the modulatory RNA molecules used in the methods described herein for generating enhanced placental stem cells are small interfering RNAs (siRNAs). In a specific embodiment, said siRNAs target one or more of the genes listed in Table 1, above. In another specific embodiment, said siRNAs target at least two, at least 3, at least 4, or at least 5 of the genes listed in Table 1, above. In another specific embodiment, said siRNAs are double-stranded, wherein one strand of said siRNAs have a sequence at least about 70%, 80%, 90%, 95%, 98% or 100% complementary to the sequence of one of the genes identified in Table 1, above (as identified based on the Gene ID of the gene provided in the table).

In another specific embodiment, the siRNAs used in the methods described herein for generating enhanced placental stem cells target the placental stem cell survival-associated gene CCND1. In another specific embodiment, the siRNAs used in the methods described herein for generating enhanced placental stem cells target the placental stem cell survival-associated gene CCND3. In another specific embodiment, the siRNAs used in the methods described herein for generating enhanced placental stem cells target the placental stem cell survival-associated gene CCNE1. In another specific embodiment, the siRNAs used in the methods described herein for generating enhanced placental stem cells target the placental stem cell survival-associated gene CCNF. In another specific embodiment, the siRNAs used in the methods described herein for generating enhanced placental stem cells target the placental stem cell survival-associated gene CDK6. In another specific embodiment, the siRNAs used in the methods described herein for generating enhanced placental stem cells target the placental stem cell survival-associated gene PPP2R5C. In another specific embodiment, the siRNAs used in the methods described herein for generating enhanced placental stem cells target the placental stem cell survival-associated gene CDC25A. In another specific embodiment, the siRNAs used in the methods described herein for generating enhanced placental stem cells target the placental stem cell survival-associated gene WEE1. In another specific embodiment, the siRNAs used in the methods described herein for generating enhanced placental stem cells target the placental stem cell survival-associated gene CHEK1. In another specific embodiment, the siRNAs used in the methods described herein for generating enhanced placental stem cells target the placental stem cell survival-associated gene MCL1. In another specific embodiment, the siRNAs used in the methods described herein for generating enhanced placental stem cells target the placental stem cell survival-associated gene BCL2. In another specific embodiment, the siRNAs used in the methods described herein for generating enhanced placental stem cells target the placental stem cell survival-associated gene PPMID. In another specific embodiment, the siRNAs used in the methods described herein for generating enhanced placental stem cells target the placental stem cell survival-associated gene HMGA1. In another specific embodiment, the siRNAs used in the methods described herein for generating enhanced placental stem cells target the placental stem cell survival-associated gene AKT3. In another specific embodiment, the siRNAs used in the methods described herein for generating enhanced placental stem cells target the placental stem cell survival-associated gene VEGFA. In another specific embodiment, the siRNAs used in the methods described herein for generating enhanced placental stem cells target the placental stem cell survival-associated gene MYB. In another specific embodiment, the siRNAs used in the methods described herein for generating enhanced placental stem cells target the placental stem cell survival-associated gene ITGA2.

In another specific embodiment, the siRNAs used in the methods described herein for generating enhanced placental stem cells target two, three, or more (i.e., a combination) of the following placental stem cell survival-associated genes: CCND1, CCND3, CCNE1, CCNF, CDK6, PPP2R5C, CDC25A, WEE1, CHEK1, MCL1, BCL2, PPMID, HMGA1, AKT3, VEGFA, MYB, and/or ITGA2. In another specific embodiment, the siRNAs used in the methods described herein for generating enhanced placental stem cells target two, three, or more (i.e., a combination) of the following placental stem cell survival-associated genes: CCND1, CCND3, CCNE1, CCNF, CDK6, CDC25A, WEE1, CHEK1, and/or MYB. In another specific embodiment, the siRNAs used in the methods described herein for generating enhanced placental stem cells target two, three, or more (i.e., a combination) of the following placental stem cell survival-associated genes: MCL1, PPMID, HMGA1, AKT3, VEGFA, and/or ITGA2.

In another embodiment, the modulatory RNA molecules used in the methods described herein for generating enhanced placental stem cells are small hairpin RNAs (shRNAs). In a specific embodiment, said shRNAs target one or more of the survival-associated genes listed in Table 1, above. In another specific embodiment, said shRNAs target at least two, at least 3, at least 4, or at least 5 of the genes listed in Table 1, above. In another specific embodiment, said shRNAs have a sequence at least about 70%, 80%, 90%, 95%, 98% or 100% complementary to the sequence of one of the genes identified in Table 1, above (as identified based on the Gene ID of the gene provided in the table).

In another specific embodiment, the shRNAs used in the methods described herein for generating enhanced placental stem cells target the placental stem cell survival-associated gene CCND1. In another specific embodiment, the shRNAs used in the methods described herein for generating enhanced placental stem cells target the placental stem cell survival-associated gene CCND3. In another specific embodiment, the shRNAs used in the methods described herein for generating enhanced placental stem cells target the placental stem cell survival-associated gene CCNE1. In another specific embodiment, the shRNAs used in the methods described herein for generating enhanced placental stem cells target the placental stem cell survival-associated gene CCNF. In another specific embodiment, the shRNAs used in the methods described herein for generating enhanced placental stem cells target the placental stem cell survival-associated gene CDK6. In another specific embodiment, the shRNAs used in the methods described herein for generating enhanced placental stem cells target the placental stem cell survival-associated gene PPP2R5C. In another specific embodiment, the shRNAs used in the methods described herein for generating enhanced placental stem cells target the placental stem cell survival-associated gene CDC25A. In another specific embodiment, the shRNAs used in the methods described herein for generating enhanced placental stem cells target the placental stem cell survival-associated gene WEE1. In another specific embodiment, the shRNAs used in the methods described herein for generating enhanced placental stem cells target the placental stem cell survival-associated gene CHEK1. In another specific embodiment, the shRNAs used in the methods described herein for generating enhanced placental stem cells target the placental stem cell survival-associated gene MCL1. In another specific embodiment, the shRNAs used in the methods described herein for generating enhanced placental stem cells target the placental stem cell survival-associated gene BCL2. In another specific embodiment, the shRNAs used in the methods described herein for generating enhanced placental stem cells target the placental stem cell survival-associated gene PPMID. In another specific embodiment, the shRNAs used in the methods described herein for generating enhanced placental stem cells target the placental stem cell survival-associated gene HMGA1. In another specific embodiment, the shRNAs used in the methods described herein for generating enhanced placental stem cells target the placental stem cell survival-associated gene AKT3. In another specific embodiment, the shRNAs used in the methods described herein for generating enhanced placental stem cells target the placental stem cell survival-associated gene VEGFA. In another specific embodiment, the shRNAs used in the methods described herein for generating enhanced placental stem cells target the placental stem cell survival-associated gene MYB. In another specific embodiment, the shRNAs used in the methods described herein for generating enhanced placental stem cells target the placental stem cell survival-associated gene ITGA2.

In another specific embodiment, the shRNAs used in the methods described herein for generating enhanced placental stem cells target two, three, or more (i.e., a combination) of the following placental stem cell survival-associated genes: CCND1, CCND3, CCNE1, CCNF, CDK6, PPP2R5C, CDC25A, WEE1, CHEK1, MCL1, BCL2, PPMID, HMGA1, AKT3, VEGFA, MYB, and/or ITGA2. In another specific embodiment, the shRNAs used in the methods described herein for generating enhanced placental stem cells target two, three, or more (i.e., a combination) of the following placental stem cell survival-associated genes: CCND1, CCND3, CCNE1, CCNF, CDK6, CDC25A, WEE1, CHEK1, and/or MYB. In another specific embodiment, the shRNAs used in the methods described herein for generating enhanced placental stem cells target two, three, or more (i.e., a combination) of the following placental stem cell survival-associated genes: MCL1, PPMID, HMGA1, AKT3, VEGFA, and/or ITGA2.

In another embodiment, the modulatory RNA molecules used in the methods described herein for generating enhanced placental stem cells are antisense RNAs. In a specific embodiment, said antisense RNAs target one or more of the survival-associated genes listed in Table 1, above. In another specific embodiment, said antisense RNAs target at least two, at least 3, at least 4, or at least 5 of the genes listed in Table 1, above. In another specific embodiment, said antisense RNAs have a sequence at least about 70%, 80%, 90%, 95%, 98% or 100% complementary to the sequence of one of the genes identified in Table 1, above (as identified based on the Gene ID of the gene provided in the table).

In another specific embodiment, the antisense RNAs used in the methods described herein for generating enhanced placental stem cells target the placental stem cell survival-associated gene CCND1. In another specific embodiment, the antisense RNAs used in the methods described herein for generating enhanced placental stem cells target the placental stem cell survival-associated gene CCND3. In another specific embodiment, the antisense RNAs used in the methods described herein for generating enhanced placental stem cells target the placental stem cell survival-associated gene CCNE1. In another specific embodiment, the antisense RNAs used in the methods described herein for generating enhanced placental stem cells target the placental stem cell survival-associated gene CCNF. In another specific embodiment, the antisense RNAs used in the methods described herein for generating enhanced placental stem cells target the placental stem cell survival-associated gene CDK6. In another specific embodiment, the antisense RNAs used in the methods described herein for generating enhanced placental stem cells target the placental stem cell survival-associated gene PPP2R5C. In another specific embodiment, the antisense RNAs used in the methods described herein for generating enhanced placental stem cells target the placental stem cell survival-associated gene CDC25A. In another specific embodiment, the antisense RNAs used in the methods described herein for generating enhanced placental stem cells target the placental stem cell survival-associated gene WEE1. In another specific embodiment, the antisense RNAs used in the methods described herein for generating enhanced placental stem cells target the placental stem cell survival-associated gene CHEK1. In another specific embodiment, the antisense RNAs used in the methods described herein for generating enhanced placental stem cells target the placental stem cell survival-associated gene MCL1. In another specific embodiment, the antisense RNAs used in the methods described herein for generating enhanced placental stem cells target the placental stem cell survival-associated gene BCL2. In another specific embodiment, the antisense RNAs used in the methods described herein for generating enhanced placental stem cells target the placental stem cell survival-associated gene PPMID. In another specific embodiment, the antisense RNAs used in the methods described herein for generating enhanced placental stem cells target the placental stem cell survival-associated gene HMGA1. In another specific embodiment, the antisense RNAs used in the methods described herein for generating enhanced placental stem cells target the placental stem cell survival-associated gene AKT3. In another specific embodiment, the antisense RNAs used in the methods described herein for generating enhanced placental stem cells target the placental stem cell survival-associated gene VEGFA. In another specific embodiment, the antisense RNAs used in the methods described herein for generating enhanced placental stem cells target the placental stem cell survival-associated gene MYB. In another specific embodiment, the antisense RNAs used in the methods described herein for generating enhanced placental stem cells target the placental stem cell survival-associated gene ITGA2.

In another specific embodiment, the antisense RNAs used in the methods described herein for generating enhanced placental stem cells target two, three, or more (i.e., a combination) of the following placental stem cell survival-associated genes: CCND1, CCND3, CCNE1, CCNF, CDK6, PPP2R5C, CDC25A, WEE1, CHEK1, MCL1, BCL2, PPMID, HMGA1, AKT3, VEGFA, MYB, and/or ITGA2. In another specific embodiment, the antisense RNAs used in the methods described herein for generating enhanced placental stem cells target two, three, or more (i.e., a combination) of the following placental stem cell survival-associated genes: CCND1, CCND3, CCNE1, CCNF, CDK6, CDC25A, WEE1, CHEK1, and/or MYB. In another specific embodiment, the antisense RNAs used in the methods described herein for generating enhanced placental stem cells target two, three, or more (i.e., a combination) of the following placental stem cell survival-associated genes: MCL1, PPMID, HMGA1, AKT3, VEGFA, and/or ITGA2.

In another embodiment, the oligomeric or polymeric molecules used in the methods described herein for generating enhanced placental stem cells are antisense DNAs. In a specific embodiment, said antisense DNAs target one or more of the survival-associated genes listed in Table 1, above. In another specific embodiment, said antisense DNAs target at least two, at least 3, at least 4, or at least 5 of the genes listed in Table 1, above. In another specific embodiment, said antisense DNAs have a sequence at least about 70%, 80%, 90%, 95%, 98% or 100% complementary to the sequence of one of the genes identified in Table 1, above (as identified based on the Gene ID of the gene provided in the table).

In another specific embodiment, the antisense DNAs used in the methods described herein for generating enhanced placental stem cells target the placental stem cell survival-associated gene CCND1. In another specific embodiment, the antisense DNAs in the methods described herein for generating enhanced placental stem cells target the placental stem cell survival-associated gene CCND3. In another specific embodiment, the antisense DNAs used in the methods described herein for generating enhanced placental stem cells target the placental stem cell survival-associated gene CCNE1. In another specific embodiment, the antisense DNAs used in the methods described herein for generating enhanced placental stem cells target the placental stem cell survival-associated gene CCNF. In another specific embodiment, the antisense DNAs used in the methods described herein for generating enhanced placental stem cells target the placental stem cell survival-associated gene CDK6. In another specific embodiment, the antisense DNAs used in the methods described herein for generating enhanced placental stem cells target the placental stem cell survival-associated gene PPP2R5C. In another specific embodiment, the antisense DNAs used in the methods described herein for generating enhanced placental stem cells target the placental stem cell survival-associated gene CDC25A. In another specific embodiment, the antisense DNAs used in the methods described herein for generating enhanced placental stem cells target the placental stem cell survival-associated gene WEE1. In another specific embodiment, the antisense DNAs used in the methods described herein for generating enhanced placental stem cells target the placental stem cell survival-associated gene CHEK1. In another specific embodiment, the antisense DNAs used in the methods described herein for generating enhanced placental stem cells target the placental stem cell survival-associated gene MCL1. In another specific embodiment, the antisense DNAs used in the methods described herein for generating enhanced placental stem cells target the placental stem cell survival-associated gene BCL2. In another specific embodiment, the antisense DNAs used in the methods described herein for generating enhanced placental stem cells target the placental stem cell survival-associated gene PPMID. In another specific embodiment, the antisense DNAs used in the methods described herein for generating enhanced placental stem cells target the placental stem cell survival-associated gene HMGA1. In another specific embodiment, the antisense DNAs used in the methods described herein for generating enhanced placental stem cells target the placental stem cell survival-associated gene AKT3. In another specific embodiment, the antisense DNAs used in the methods described herein for generating enhanced placental stem cells target the placental stem cell survival-associated gene VEGFA. In another specific embodiment, the antisense DNAs used in the methods described herein for generating enhanced placental stem cells target the placental stem cell survival-associated gene MYB. In another specific embodiment, the antisense DNAs used in the methods described herein for generating enhanced placental stem cells target the placental stem cell survival-associated gene ITGA2.

In another specific embodiment, the antisense DNAs used in the methods described herein for generating enhanced placental stem cells target two, three, or more (i.e., a combination) of the following placental stem cell survival-associated genes: CCND1, CCND3, CCNE1, CCNF, CDK6, PPP2R5C, CDC25A, WEE1, CHEK1, MCL1, BCL2, PPMID, HMGA1, AKT3, VEGFA, MYB, and/or ITGA2. In another specific embodiment, the antisense DNAs used in the methods described herein for generating enhanced placental stem cells target two, three, or more (i.e., a combination) of the following placental stem cell survival-associated genes: CCND1, CCND3, CCNE1, CCNF, CDK6, CDC25A, WEE1, CHEK1, and/or MYB. In another specific embodiment, the antisense DNAs used in the methods described herein for generating enhanced placental stem cells target two, three, or more (i.e., a combination) of the following placental stem cell survival-associated genes: MCL1, PPMID, HMGA1, AKT3, VEGFA, and/or ITGA2.

In another aspect, provided herein are isolated enhanced placental stem cells, and compositions thereof, produced according to the methods described herein, e.g., placental stem cells that have been modified by contacting said placental stem cells with an effective amount of one or more oligomeric or polymeric molecules (e.g., modulatory RNA molecules), such that the placental stem cells survive for longer durations of time under certain conditions as compared to corresponding unmodified placental stem cells. Such enhanced placental stem cells demonstrate increased survival under conditions that lead to cell death (e.g., in environments where components in the environment can harm the cells, e.g., in vivo) as compared to, e.g., corresponding unmodified placental stem cells (e.g., corresponding placental stem cells that have not been contacted with an effective amount of oligomeric or polymeric molecules (e.g., modulatory RNA molecules)). In certain embodiments, the enhanced placental stem cells provided herein demonstrate increased survival in the presence of serum (e.g., human or rat serum), complement, antibody(ies), other cells (e.g., cells of the immune system), or conditions that can lead to anoikis (e.g., low-attachment conditions) as compared to corresponding unmodified placental stem cells.

In certain embodiments, the enhanced placental stem cells provided herein demonstrate one or more of (i) decreased caspase 3/7 activity, (ii) increased mitochondrial membrane potential, and/or (iii) increased metabolic activity when exposed to a given condition as compared to corresponding unmodified placental stem cells exposed to the same condition. In a specific embodiment, the enhanced placental stem cells provided herein demonstrate decreased caspase 3/7 activity and increased mitochondrial membrane potential, and increased metabolic activity when exposed to a given condition as compared to corresponding unmodified placental stem cells exposed to the same condition.

In certain embodiments, the enhanced placental stem cells provided herein enter a quiescent state when exposed to a condition known to cause cell death of the placental stem cell, e.g., culturing of the placental stem cells in serum (e.g., rat serum).

In one embodiment, the isolated enhanced placental stem cells provided herein express at least one survival-associated gene at a decreased level as compared to the expression of the same survival-associated gene in a corresponding unmodified placental stem cell. In a specific embodiment, provided herein is an isolated enhanced placental stem cell, or population thereof, wherein said isolated enhanced placental stem cell expresses at least one survival-associated gene from those listed in Table 1 at a decreased level as compared to the expression of the same survival-associated gene in a corresponding unmodified placental stem cell. In another specific embodiment, provided herein is an isolated enhanced placental stem cell, or population thereof, wherein said isolated enhanced placental stem cell expresses more than one survival-associated gene (e.g., a combination) from those listed in Table 1 at a decreased level as compared to the expression of the same survival-associated gene in a corresponding unmodified placental stem cell, e.g., the isolated enhanced placental stem cell expresses, two, three, four, five, six, seven, eight, nine, ten, or greater than ten genes from those listed in Table 1 at a decreased level as compared to the expression of the same survival-associated gene(s) in a corresponding unmodified placental stem cell.

In another embodiment, the isolated enhanced placental stem cells provided herein express at least one survival-associated gene at an increased level as compared to the expression of the same survival-associated gene in a corresponding unmodified placental stem cell. In a specific embodiment, provided herein is an isolated enhanced placental stem cell, or population thereof, wherein said isolated enhanced placental stem cell expresses at least one survival-associated gene from those listed in Table 1 at an increased level as compared to the expression of the same survival-associated gene in a corresponding unmodified placental stem cell. In another specific embodiment, provided herein is an isolated enhanced placental stem cell, or population thereof, wherein said isolated enhanced placental stem cell expresses more than one survival-associated gene (e.g., a combination) from those listed in Table 1 at an increased level as compared to the expression of the same survival-associated gene in a corresponding unmodified placental stem cell, e.g., the isolated enhanced placental stem cell expresses, two, three, four, five, six, seven, eight, nine, ten, or greater than ten genes from those listed in Table 1 at an increased level as compared to the expression of the same survival-associated gene(s) in a corresponding unmodified placental stem cell.

In another specific embodiment, provided herein is an isolated enhanced placental stem cell, wherein said enhanced placental stem cell expresses the survival-associated gene CCND1 at a decreased level as compared to the expression of the survival-associated gene CCND1 in a corresponding unmodified placental stem cell. In another specific embodiment, provided herein is an isolated enhanced placental stem cell, wherein said enhanced placental stem cell expresses the survival-associated gene CCND3 at a decreased level as compared to the expression of the survival-associated gene CCND3 in a corresponding unmodified placental stem cell. In another specific embodiment, provided herein is an isolated enhanced placental stem cell, wherein said enhanced placental stem cell expresses the survival-associated gene CCNE1 at a decreased level as compared to the expression of the survival-associated gene CCNE1 in a corresponding unmodified placental stem cell. In another specific embodiment, provided herein is an isolated enhanced placental stem cell, wherein said enhanced placental stem cell expresses the survival-associated gene CCNF at a decreased level as compared to the expression of the survival-associated gene CCNF in a corresponding unmodified placental stem cell. In another specific embodiment, provided herein is an isolated enhanced placental stem cell, wherein said enhanced placental stem cell expresses the survival-associated gene CDK6 at a decreased level as compared to the expression of the survival-associated gene CDK6 in a corresponding unmodified placental stem cell. In another specific embodiment, provided herein is an isolated enhanced placental stem cell, wherein said enhanced placental stem cell expresses the survival-associated gene PPP2R5C at a decreased level as compared to the expression of the survival-associated gene PPP2R5C in a corresponding unmodified placental stem cell. In another specific embodiment, provided herein is an isolated enhanced placental stem cell, wherein said enhanced placental stem cell expresses the survival-associated gene CDC25A at a decreased level as compared to the expression of the survival-associated gene CDC25A in a corresponding unmodified placental stem cell.

In another specific embodiment, provided herein is an isolated enhanced placental stem cell, wherein said enhanced placental stem cell expresses the survival-associated gene WEE1 at a decreased level as compared to the expression of the survival-associated gene WEE1 in a corresponding unmodified placental stem cell. In another specific embodiment, provided herein is an isolated enhanced placental stem cell, wherein said enhanced placental stem cell expresses the survival-associated gene CHEK1 at a decreased level as compared to the expression of the survival-associated gene CHEK1 in a corresponding unmodified placental stem cell. In another specific embodiment, provided herein is an isolated enhanced placental stem cell, wherein said enhanced placental stem cell expresses the survival-associated gene MCL1 at a decreased level as compared to the expression of the survival-associated gene MCL1 in a corresponding unmodified placental stem cell. In another specific embodiment, provided herein is an isolated enhanced placental stem cell, wherein said enhanced placental stem cell expresses the survival-associated gene BCL2 at a decreased level as compared to the expression of the survival-associated gene BCL2 in a corresponding unmodified placental stem cell. In another specific embodiment, provided herein is an isolated enhanced placental stem cell, wherein said enhanced placental stem cell expresses the survival-associated gene PPMID at a decreased level as compared to the expression of the survival-associated gene PPMID in a corresponding unmodified placental stem cell. In another specific embodiment, provided herein is an isolated enhanced placental stem cell, wherein said enhanced placental stem cell expresses the survival-associated gene HMGA1 at a decreased level as compared to the expression of the survival-associated gene HMGA1 in a corresponding unmodified placental stem cell. In another specific embodiment, provided herein is an isolated enhanced placental stem cell, wherein said enhanced placental stem cell expresses the survival-associated gene AKT3 at a decreased level as compared to the expression of the survival-associated gene AKT3 in a corresponding unmodified placental stem cell. In another specific embodiment, provided herein is an isolated enhanced placental stem cell, wherein said enhanced placental stem cell expresses the survival-associated gene VEGFA at a decreased level as compared to the expression of the survival-associated gene VEGFA in a corresponding unmodified placental stem cell. In another specific embodiment, provided herein is an isolated enhanced placental stem cell, wherein said enhanced placental stem cell expresses the survival-associated gene MYB at a decreased level as compared to the expression of the survival-associated gene MYB in a corresponding unmodified placental stem cell. In another specific embodiment, provided herein is an isolated enhanced placental stem cell, wherein said enhanced placental stem cell expresses the survival-associated gene ITGA2 at a decreased level as compared to the expression of the survival-associated gene ITGA2 in a corresponding unmodified placental stem cell.

In another specific embodiment, provided herein is an isolated enhanced placental stem cell, wherein said enhanced placental stem cell expresses the survival-associated gene PPP2R5C at an increased level as compared to the expression of the survival-associated gene PPP2R5C in a corresponding unmodified placental stem cell. In another specific embodiment, provided herein is an isolated enhanced placental stem cell, wherein said enhanced placental stem cell expresses the survival-associated gene MCL1 at an increased level as compared to the expression of the survival-associated gene MCL1 in a corresponding unmodified placental stem cell. In another specific embodiment, provided herein is an isolated enhanced placental stem cell, wherein said enhanced placental stem cell expresses the survival-associated gene PPMID at an increased level as compared to the expression of the survival-associated gene PPMID in a corresponding unmodified placental stem cell. In another specific embodiment, provided herein is an isolated enhanced placental stem cell, wherein said enhanced placental stem cell expresses the survival-associated gene HMGA1 at an increased level as compared to the expression of the survival-associated gene HMGA1 in a corresponding unmodified placental stem cell. In another specific embodiment, provided herein is an isolated enhanced placental stem cell, wherein said enhanced placental stem cell expresses the survival-associated gene AKT3 at an increased level as compared to the expression of the survival-associated gene AKT3 in a corresponding unmodified placental stem cell. In another specific embodiment, provided herein is an isolated enhanced placental stem cell, wherein said enhanced placental stem cell expresses the survival-associated gene VEGFA at an increased level as compared to the expression of the survival-associated gene VEGFA in a corresponding unmodified placental stem cell. In another specific embodiment, provided herein is an isolated enhanced placental stem cell, wherein said enhanced placental stem cell expresses the survival-associated gene ITGA2 at an increased level as compared to the expression of the survival-associated gene ITGA2 in a corresponding unmodified placental stem cell. In another specific embodiment, provided herein is an isolated enhanced placental stem cell, wherein said enhanced placental stem cell expresses the survival-associated gene CCND1 at an increased level as compared to the expression of the survival-associated gene CCND1 in a corresponding unmodified placental stem cell. In another specific embodiment, provided herein is an isolated enhanced placental stem cell, wherein said enhanced placental stem cell expresses the survival-associated gene CCND3 at an increased level as compared to the expression of the survival-associated gene CCND3 in a corresponding unmodified placental stem cell. In another specific embodiment, provided herein is an isolated enhanced placental stem cell, wherein said enhanced placental stem cell expresses the survival-associated gene CCNE1 at an increased level as compared to the expression of the survival-associated gene CCNE1 in a corresponding unmodified placental stem cell. In another specific embodiment, provided herein is an isolated enhanced placental stem cell, wherein said enhanced placental stem cell expresses the survival-associated gene CDC25A at an increased level as compared to the expression of the survival-associated gene CDC25A in a corresponding unmodified placental stem cell. In another specific embodiment, provided herein is an isolated enhanced placental stem cell, wherein said enhanced placental stem cell expresses the survival-associated gene WEE1 at an increased level as compared to the expression of the survival-associated gene WEE1 in a corresponding unmodified placental stem cell.

In another specific embodiment, provided herein is an isolated enhanced placental stem cell, wherein said enhanced placental stem cell expresses one, two, three, or more (i.e., a combination) of the following placental stem cell survival-associated genes at a decreased level as compared to the expression of the same survival-associated gene(s) in a corresponding unmodified placental stem cell: CCND1, CCND3, CCNE1, CCNF, CDK6, PPP2R5C, CDC25A, WEE1, CHEK1, MCL1, BCL2, PPMID, HMGA1, AKT3, VEGFA, MYB, and/or ITGA2. In another specific embodiment, provided herein is an isolated enhanced placental stem cell, wherein said enhanced placental stem cell (i) expresses one, two, three, or more of the following placental stem cell survival-associated genes at a decreased level as compared to the expression of the same survival-associated gene(s) in a corresponding unmodified placental stem cell: CCND1, CCND3, CCNE1, CCNF, CDK6, PPP2R5C, CDC25A, WEE1, CHEK1, MCL1, BCL2, PPMID, HMGA1, AKT3, VEGFA, MYB, and/or ITGA2; and (ii) expresses at least one additional survival-associated gene recited in Table 1 at an increased or a decreased level as compared to the expression of the same survival-associated gene (s) in a corresponding unmodified placental stem cell. Further provided herein are populations of cells comprising such enhanced placental stem cells and compositions comprising such enhanced placental stem cells.

In another specific embodiment, provided herein is an isolated enhanced placental stem cell, wherein said enhanced placental stem cell expresses one, two, three, or more (i.e., a combination) of the following placental stem cell survival-associated genes at an increased level as compared to the expression of the same survival-associated gene(s) in a corresponding unmodified placental stem cell: CCND1, CCND3, CCNE1, PPP2R5C, CDC25A, WEE1, MCL1, PPMID, HMGA1, AKT3, VEGFA, PPP2R5C, and/ or ITGA2. In another specific embodiment, provided herein is an isolated enhanced placental stem cell, wherein said enhanced placental stem cell (i) expresses one, two, three, or more of the following placental stem cell survival-associated genes at an increased level as compared to the expression of the same survival-associated gene(s) in a corresponding unmodified placental stem cell: CCND1, CCND3, CCNE1, PPP2R5C, CDC25A, WEE1, MCL1, PPMID, HMGA1, AKT3, VEGFA, PPP2R5C, and/or ITGA2; and (ii) expresses at least one additional survival-associated gene recited in Table 1 at an increased or a decreased level as compared to the expression of the same survival-associated gene (s) in a corresponding unmodified placental stem cell. Further provided herein are populations of cells comprising such enhanced placental stem cells and compositions comprising such enhanced placental stem cells.

In a specific embodiment, the enhanced placental stem cells described herein are $CD10^+$, $CD34^-$, $CD105^+$, and $CD200^+$. In another specific embodiment, the enhanced placental stem cells described herein express CD200 and do not express HLA-G; or express CD73, CD105, and CD200; or express CD200 and OCT-4; or express CD73 and CD105 and do not express HLA-G; or express CD73 and CD105 and facilitate the formation of one or more embryoid-like bodies in a population of placental cells comprising said stem cell when said population is cultured under conditions that allow for the formation of an embryoid-like body; or express OCT-4 and facilitate the formation of one or more embryoid-like bodies in a population of placental cells comprising said stem cell when said population is cultured under conditions that allow for the formation of an embryoid-like body. In another specific embodiment, the enhanced placental stem cells described herein are additionally $CD90^+$ and $CD45^-$. In another specific embodiment, the enhanced placental stem cells described herein are additionally CD80 and $CD86^-$. In yet other embodiments, the enhanced placental stem cells described herein express one or more of CD44, CD90, HLA-A,B,C or ABC-p, and/or do not express one or more of CD45, CD117, CD133, KDR, CD80, CD86, HLA-DR, SSEA3, SSEA4, or CD38. In certain embodiments, the enhanced placental stem cells described herein suppress the activity of an immune cell, e.g., suppress proliferation of a T cell to a detectably greater degree than corresponding unmodified placental stem cells (e.g., placental cells that have not been contacted with an effective amount of oligomeric or polymeric molecules (e.g., modulatory RNA molecules)), as determinable by, e.g., a mixed leukocyte reaction assay, regression assay, or bead T cell assay.

In another aspect, provided herein is a method for modulating an immune response, e.g., modulating the immune response of a subject, e.g., a human subject, or modulating an immune response in vitro, comprising contacting immune cells with the enhanced placental stem cells described herein, or a composition thereof. In a specific embodiment, the enhanced placental stem cells provided herein are capable of modulating an immune response to the same degree as an equivalent amount of corresponding unmodified placental stem cells. In another specific embodiment, the enhanced placental stem cells used in a method for modulating an immune response have been modified by contacting said placental stem cells with an effective amount of one or more oligomeric or polymeric molecules (e.g., modulatory RNA molecules) as described herein. Assays for measuring the ability of cells (e.g., placental stem cells, including enhanced placental stem cells) to modulate an immune response are known in the art (see, e.g., U.S. Pat. No. 7,682,803, the disclosure of which is herein incorporated by reference in its entirety) and described herein, e.g., mixed lymphocyte reaction, regression assay.

In another aspect, provided herein is a method for promoting angiogenesis, e.g., promoting angiogenesis in a subject, e.g., a human subject, comprising administering to said subject the enhanced placental stem cells described herein, or a composition thereof. In a specific embodiment, the enhanced placental stem cells provided herein are capable of promoting angiogenesis to the same degree as an equivalent amount of corresponding unmodified placental stem cells. In another specific embodiment, the enhanced placental stem cells used in a method for promoting angiogenesis have been modified by contacting said placental stem cells with an effective amount of one or more oligomeric or polymeric molecules (e.g., modulatory RNA molecules) as described herein. Assays for measuring the ability of cells (e.g., placental stem cells, including enhanced placental stem cells) to promote angiogenesis are known in the art (see, e.g., U.S. Patent Application Publication No. 2011/0250182, the disclosure of which is herein incorporated by reference in its entirety), e.g., assaying the ability of cells to promote tube formation by endothelial cells, assaying the ability of cells to promote endothelial cell migration and/or proliferation, and assaying the ability of cells to secrete factors that promote angiogenesis.

3.1 Definitions

As used herein, the term "amount," when referring to placental stem cells, e.g., enhanced placental stem cells described herein, means a particular number of placental stem cells (e.g., enhanced placental stem cells).

As used herein, the term "derived" means isolated from or otherwise purified. For example, placental derived adherent cells are isolated from placenta. The term "derived" encompasses cells that are cultured from cells isolated directly from a tissue, e.g., the placenta, and cells cultured or expanded from primary isolates.

As used herein, "immunolocalization" means the detection of a compound, e.g., a cellular marker, using an immune protein, e.g., an antibody or fragment thereof in, for example, flow cytometry, fluorescence-activated cell sorting, magnetic cell sorting, in situ hybridization, immunohistochemistry, or the like.

As used herein, the term "SH2" refers to an antibody that binds an epitope on the marker CD105. Thus, cells that are referred to as $SH2^+$ are $CD105^+$.

As used herein, the terms "SH3" and SH4" refer to antibodies that bind epitopes present on the marker CD73. Thus, cells that are referred to as $SH3^+$ and/or $SH4^+$ are $CD73^+$.

As used herein, a stem cell is "isolated" if at least 50%, 60%, 70%, 80%, 90%, 95%, or at least 99% of the other cells with which the stem cell is naturally associated are removed from the stem cell, e.g., during collection and/or culture of the stem cell. A population of "isolated" cells means a population of cells that is substantially separated from other cells of the tissue, e.g., placenta, from which the population of cells is derived. In some embodiments, a population of, e.g., stem cells is "isolated" if at least 50%, 60%, 70%, 80%, 90%, 95%, or at least 99% of the cells with which the population of stem cells are naturally associated are removed from the population of stem cells, e.g., during collection and/or culture of the population of stem cells.

As used herein, the term "placental stem cell" refers to a stem cell or progenitor cell that is derived from, e.g., isolated from, a mammalian placenta, regardless of the number of passages after a primary culture, which adheres to a tissue culture substrate (e.g., tissue culture plastic or a fibronectin-coated tissue culture plate). The term "placental stem cell" as used herein does not, however, refer to a trophoblast, a cytotrophoblast, embryonic germ cell, or embryonic stem cell, as those cells are understood by persons of skill in the art. The terms "placental stem cell" and "placenta-derived stem cell" may be used interchangeably. Unless otherwise noted herein, the term "placental" includes the umbilical cord. The placental stem cells disclosed herein are, in certain embodiments, multipotent in vitro (that is, the cells differentiate in vitro under differentiating conditions), multipotent in vivo (that is, the cells differentiate in vivo), or both.

As used herein, a cell is "positive" for a particular marker when that marker is detectable. For example, a placental stem cell is positive for, e.g., CD73 because CD73 is detectable on placental stem cells in an amount detectably greater than background (in comparison to, e.g., an isotype control or an experimental negative control for any given assay). A cell is also positive for a marker when that marker can be used to distinguish the cell from at least one other cell type, or can be used to select or isolate the cell when present or expressed by the cell.

As used herein, the term "stem cell" refers to a cell that retains at least one attribute of a stem cell, e.g., a marker or gene expression profile associated with one or more types of stem cells; the ability to replicate at least 10-40 times in culture; multipotency, e.g., the ability to differentiate, either in vitro, in vivo or both, into cells of one or more of the three germ layers; the lack of adult (i.e., differentiated) cell characteristics, or the like.

As used herein, "immunomodulation" and "immunomodulatory" mean causing, or having the capacity to cause, a detectable change in an immune response, and the ability to cause a detectable change in an immune response.

As used herein, "immunosuppression" and "immunosuppressive" mean causing, or having the capacity to cause, a detectable reduction in an immune response, and the ability to cause a detectable suppression of an immune response.

As used herein, the term "oligomeric or polymeric molecule" refers to a biomolecule that is capable of targeting a gene, RNA, or protein of interest (e.g., by binding or hybridizing to a region of a gene, RNA, or protein of interest). A gene, RNA, or protein of interest is "targeted" by an oligomeric or polymeric molecule by virtue of the fact that the oligomeric or polymeric molecule is complementary to the nucleic acid or amino acid sequence of the gene, RNA, or protein of interest (thus, the gene, RNA, or protein of interest is a "target" of the oligomeric or polymeric molecule). Oligomeric and polymeric molecules include, for example, oligonucleotides, oligonucleosides, oligonucleotide analogs, oligonucleotide mimetics, oligopeptides or polypeptides, and any combinations (e.g., chimeric combinations) thereof. As such, these compounds may be single-stranded, double-stranded, circular, branched or have hairpins and can comprise structural elements such as internal or terminal bulges or loops. Oligomeric or polymeric double-stranded molecules can be two strands hybridized to form double-stranded compounds or a single strand with sufficient self complementarity to allow for hybridization and formation of a fully or partially double-stranded molecule.

As used herein, the term "modulatory RNA molecule" refers to an RNA molecule that modulates, (e.g., up-regulates or down-regulates) directly or indirectly, the expression or activity of the selectable target(s) (e.g., a target gene, RNA, or protein). In certain embodiments, a "modulatory RNA molecule" is a siRNA, microRNA (miRNA), microRNA mimic (miRNA mimic), antisense RNA, shRNA, shRNAmir, or a hybrid or a combination thereof that modulates the expression of the selectable target in a host cell. In certain embodiments, the modulatory RNA molecules provided herein comprise about 1 to about 100, from about 8 to about 80, 10 to 50, 13 to 80, 13 to 50, 13 to 30, 13 to 24, 18 to 22, 18-24, 19 to 23, 20 to 80, 20 to 50, 20 to 30, or 20 to 24 nucleobases (i.e. from about 1 to about 100 linked nucleosides).

As used herein, the phrase "increased survival," when describing the survival of enhanced placental stem cells as compared to corresponding unmodified placental stem cells refers to the ability of the enhanced placental stem cells to remain viable under conditions that cause the death (e.g., by apoptosis) of unmodified placental stem cells. In certain embodiments, increased survival of the enhanced placental stem cells described herein relative to corresponding unmodified placental stem cells refers to the ability of the enhanced placental stem cells to exhibit at least a 1.5-fold, 2-fold, 2.5-fold, 3-fold, 3.5-fold, 4-fold, 4.5-fold, 5-fold, 6-fold, 7-fold, 8-fold, 9-fold, or 10-fold increase in survival time when cultured under a given condition(s) relative to an equivalent amount of corresponding unmodified placental stem cells cultured under the same condition(s). In certain embodiments, increased survival of the enhanced placental stem cells described herein relative to corresponding unmodified placental stem cells refers to the ability of the enhanced placental stem cells to exhibit at least a 1.5-fold to 2.5-fold, a 2-fold to 3-fold, a 2.5-fold to 3.5-fold, a 3-fold to 4-fold, a 3.5-fold to 4.5-fold, a 4-fold to 5-fold, a 5-fold to 6-fold, a 6-fold to 7-fold, a 7-fold to 8-fold, an 8-fold to 9-fold, or a 9-fold to 10-fold increase in survival time when cultured under a given condition(s) relative to an equivalent amount of corresponding unmodified placental stem cells cultured under the same condition(s). Survival of enhanced placental stem cells and unmodified placental stem cells can be assessed using methods known in the art, e.g., trypan blue exclusion assay, fluorescein diacetate uptake assay, propidium iodide uptake assay; thymidine uptake assay, and MTT (3-(4,5-Dimethylthiazol-2-yl)-2,5-diphenyltetrazolium bromide) assay. In certain embodiments, increased survival of the enhanced placental stem cells described herein relative to corresponding unmodified placental stem cells refers to one or more of (i) decreased caspase 3/7 activity, (ii) increased mitochondrial membrane potential, and/or (iii) increased metabolic activity in the placental stem cells when cultured under a given condition(s) (e.g., a condition that that causes cell death) as compared to corresponding unmodified placental stem cells cultured under the same condition(s). In certain embodiments, enhanced placental stem cells exhibit (i) at least a 1.5-fold, 2-fold, 2.5-fold, 3-fold, 3.5-fold, 4-fold, 4.5-fold, 5-fold, 6-fold, 7-fold, 8-fold, 9-fold, or 10-fold decrease in caspase 3/7 activity; (ii) at least a 1.5-fold, 2-fold, 2.5-fold, 3-fold, 3.5-fold, 4-fold, 4.5-fold, 5-fold, 6-fold, 7-fold, 8-fold, 9-fold, or 10-fold increase in mitochondrial membrane potential; and/or (iii) at least a 1.5-fold, 2-fold, 2.5-fold, 3-fold, 3.5-fold, 4-fold, 4.5-fold, 5-fold, 6-fold, 7-fold, 8-fold, 9-fold, or 10-fold increase in metabolic activity when cultured under a given condition(s) (e.g., a condition that that causes cell death) as compared to corresponding unmodified placental stem cells cultured under the same condition(s). In certain embodiments, enhanced placental stem cells exhibit (i) at least a 1.5-fold to 2.5-fold, a 2-fold to 3-fold, a 2.5-fold to 3.5-fold, a 3-fold to 4-fold, a 3.5-fold to 4.5-fold, a 4-fold to 5-fold, a 5-fold to 6-fold, a 6-fold to 7-fold, a 7-fold to 8-fold, an 8-fold to 9-fold, or a 9-fold to 10-fold decrease in caspase 3/7 activity; (ii) at least a 1.5-fold to 2.5-fold, a 2-fold to 3-fold, a 2.5-fold to 3.5-fold, a 3-fold to 4-fold, a 3.5-fold to 4.5-fold, a 4-fold to 5-fold, a 5-fold to 6-fold, a 6-fold to 7-fold, a 7-fold to 8-fold, an 8-fold to 9-fold, or a 9-fold to 10-fold increase in mitochondrial membrane potential; and/or (iii) at least a 1.5-fold to 2.5-fold, a 2-fold to 3-fold, a 2.5-fold to 3.5-fold, a 3-fold to 4-fold, a 3.5-fold to 4.5-fold, a 4-fold to 5-fold, a 5-fold to 6-fold, a 6-fold to 7-fold, a 7-fold to 8-fold, an 8-fold to 9-fold, or a 9-fold to 10-fold increase in metabolic activity when cultured under a given condition(s) (e.g., a condition that that causes cell death) as compared to corresponding unmodified placental stem cells cultured under the same condition(s). Caspase 3/7 activity, mitochondrial membrane potential, and metabolic activity can be assessed using methods known in the art, e.g., as described in Sections 6.1.1.1.3 and 6.1.1.2, below.

As used herein, the phrase "decreased level," when referring to the level of expression of a given gene in an enhanced placental stem cell as compared to the expression of the same gene in a corresponding unmodified placental stem cell means that the expression of the gene in the enhanced placental stem cell is downregulated or inhibited, resulting in, e.g., a reduction in the mRNA transcript produced by the gene and/or the protein resulting from the expression of the gene. As used herein, the phrase "increased level," when referring to the level of expression of a given gene in an enhanced placental stem cell as compared to the expression of the same gene in a corresponding unmodified placental stem cell means that the expression of the gene in the enhanced placental stem cell is upregulated, resulting in, e.g., an increase in the amount of mRNA transcripts produced by the gene and/or an increase in the amount of protein resulting from the expression of the gene. Determination of whether or not a given gene is expressed at a decreased level or an increased level can be accomplished by any art-recognized method for detection of protein production or nucleic acid production by cells, e.g. nucleic acid-based methods, e.g., northern blot analysis, reverse transcriptase polymerase chain reaction (RT-PCR), real-time PCR, quantitative PCR, and the like. Expression of proteins can be assessed using antibodies that bind to the protein of interest, e.g., in an ELISA, Western blot, sandwich assay, or the like. In certain embodiments, a gene in an enhanced placental stem cell (e.g., a survival-associated gene) is expressed at a decreased level if its expression is decreased by at least a 1.5-fold, 2-fold, 2.5-fold, 3-fold, 3.5-fold, 4-fold, 4.5-fold, 5-fold, 6-fold, 7-fold, 8-fold, 9-fold, or 10-fold as compared to the expression of the gene in a corresponding unmodified placental stem cell. In certain embodiments, a gene in an enhanced placental stem cell (e.g., a survival-associated gene) is expressed at a decreased level if its expression is decreased by at least 1.5-fold to 2.5-fold, 2-fold to 3-fold, 2.5-fold to 3.5-fold, 3-fold to 4-fold, 3.5-fold to 4.5-fold, 4-fold to 5-fold, 5-fold to 6-fold, 6-fold to 7-fold, 7-fold to 8-fold, 8-fold to 9-fold, or 9-fold to 10-fold as compared to the expression of the gene in a corresponding unmodified placental stem cell. In certain embodiments, a gene in an enhanced placental stem cell (e.g., a survival-associated gene) is expressed at an increased level if its expression is increased by at least a 1.5-fold, 2-fold, 2.5-fold, 3-fold, 3.5-fold, 4-fold, 4.5-fold, 5-fold, 6-fold, 7-fold, 8-fold, 9-fold, or 10-fold as compared to the expression of the gene in a corresponding unmodified placental stem cell. In certain embodiments, a gene in an enhanced placental stem cell (e.g., a survival-associated gene) is expressed at an increased level if its expression is increased by at least 1.5-fold to 2.5-fold, 2-fold to 3-fold, 2.5-fold to 3.5-fold, 3-fold to 4-fold, 3.5-fold to 4.5-fold, 4-fold to 5-fold, 5-fold to 6-fold, 6-fold to 7-fold, 7-fold to 8-fold, 8-fold to 9-fold, or 9-fold to 10-fold as compared to the expression of the gene in a corresponding unmodified placental stem cell.

As used herein, the term "effective amount" in the context contacting placental stem cells with oligomeric or polymeric molecules refers to the amount of oligomeric or polymeric molecules sufficient to produce an enhanced placental stem cell, as described herein.

4. BRIEF DESCRIPTION OF THE FIGURES

(FIG. 5A) Change in G0/G1 Phase; (FIG. 5B) Change in S Phase; (FIG. 5C) Change in G2/M Phase.

5. DETAILED DESCRIPTION

Figure 1:
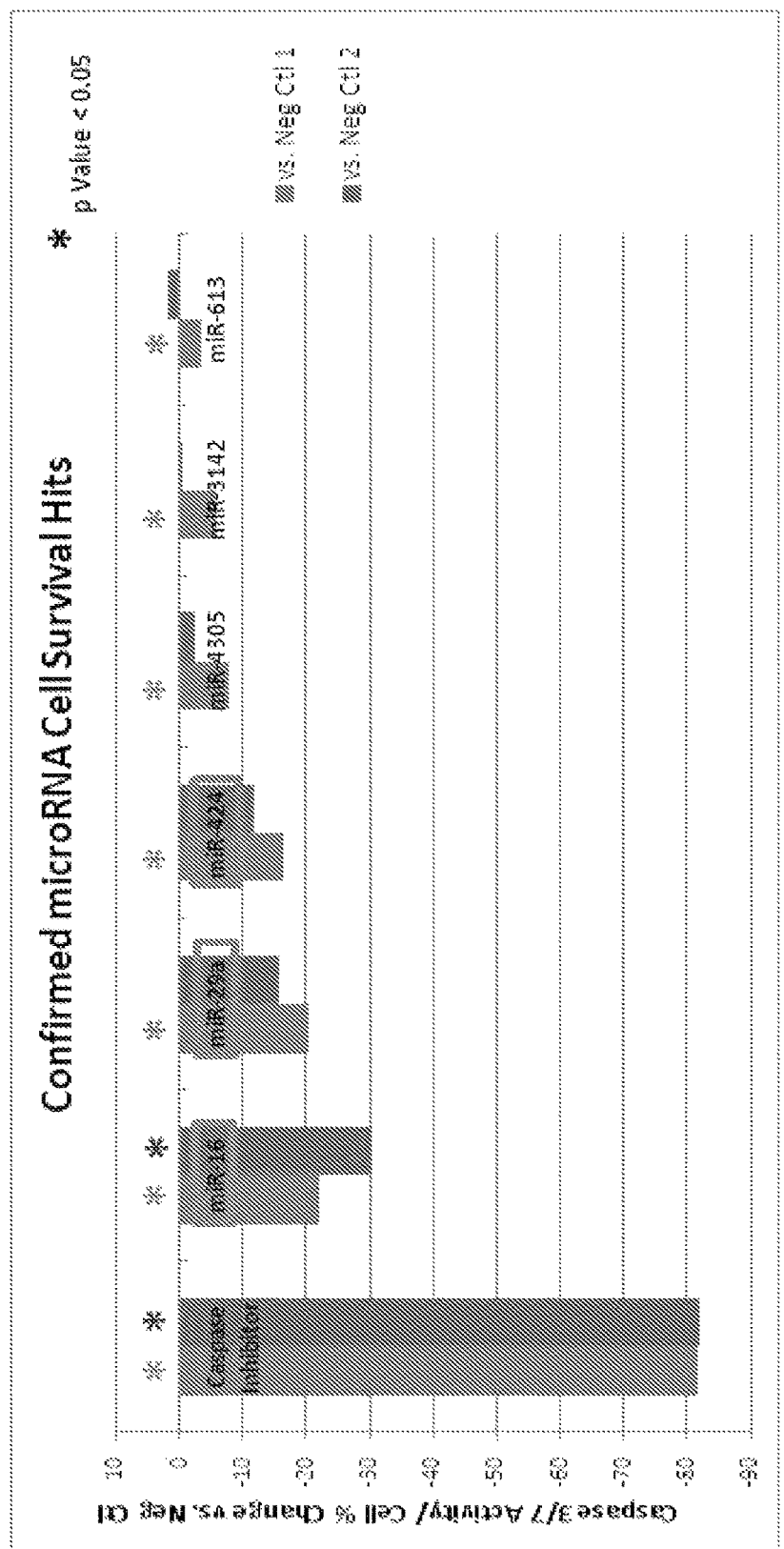
FIG. 1 depicts caspase 3/7 activity in placental stem cells transfected with different microRNAs as compared to caspase 3/7 activity in placental stem cells transfected with negative controls or cultured in the presence of a caspase inhibitor.

5.1 Production of Enhanced Placental Stem Cells

In one aspect, provided herein are methods of modifying placental stem cells such that the placental stem cells survive for longer durations of time under certain conditions as compared to corresponding unmodified placental stem cells, e.g., to make the placental stem cells resistant to conditions that lead to cell death (i.e., to make enhanced placental stem cells). Such methods comprise contacting the placental stem cells with an effective amount of one or more oligomeric or polymeric molecules, such that one or more genes identified herein as being associated with survival ("survival-associated genes") in the placental stem cells is inhibited, i.e., the expression of the gene in the placental stem cells contacted with the oligomeric or polymeric molecules is lessened as compared to the expression of the gene in corresponding unmodified placental stem cells. In certain embodiments, the oligomeric or polymeric molecules used in the methods described herein comprise nucleotides (e.g., DNA or RNA molecules), nucleosides, nucleotide analogs, nucleotide mimetics, polypeptides, nucleotide analogs, nucleotide mimetics, and any combinations (e.g., chimeric combinations) thereof. In a specific embodiment, the methods described herein for generating enhanced placental stem cells comprise contacting said placental stem cells with a combination of two or more nucleotides (e.g., DNA or RNA molecules), nucleosides, nucleotide analogs, nucleotide mimetics, polypeptides, nucleotide analogs, and/or nucleotide mimetics.

In one embodiment, the nucleotide analog is an RNA analog, for example, an RNA analog that has been modified in the 2'-OH group, e.g. by substitution with a group, for example —O—CH$_3$, —O—CH$_2$—CH$_2$—O—CH$_3$, —O—CH$_2$—CH$_2$—CH$_2$—NH$_2$, —O—CH$_2$—CH$_2$—CH$_2$—OH or —F.

In certain embodiments, the oligomeric or polymeric molecules used in the methods described herein comprise one or more modifications (e.g., chemical modifications) in the sugars, bases, or internucleoside linkages. As used herein, the term "internucleoside linkage group" refers to a group capable of covalently coupling together two nucleotides, such as between RNA units. Examples include phosphate, phosphodiester groups and phosphorothioate groups. In one embodiment, the oligomeric or polymeric molecules used in the methods described herein comprise at least one phosphate internucleoside linkage group. In one embodiment, the oligomeric or polymeric molecules used in the methods described herein comprise at least one phosphodiester internucleoside linkage group.

In certain embodiments, the oligomeric or polymeric molecules used in the methods described herein are single-stranded oligonucleotides or polynucleotides. In certain embodiments, the oligomeric or polymeric molecules used in the methods described herein are double-stranded oligonucleotides or polynucleotides. In certain embodiments, the oligonucleotides or polynucleotides used in the methods described herein comprise one or more modifications (e.g., chemical modifications) in the sugars, bases, or internucleoside linkages.

In a specific embodiment, the oligomeric molecules used in the methods described herein are modulatory RNA molecules. In certain embodiments, the modulatory RNA molecules are microRNAs, small interfering RNAs (siRNAs), antisense RNAs, miR mimics, small hairpin RNAs (shRNAs), microRNA-adapted shRNA (shRNAmirs), or any combination thereof.

In another specific embodiment, the oligomeric molecules used in the methods described herein are antisense DNA molecules.

In another specific embodiment, the methods described herein comprise contacting placental stem cells with a combination of microRNAs, small interfering RNAs (siRNAs), antisense RNAs, antisense DNAs, miR mimics, small hairpin RNAs (shRNAs), and/or microRNA-adapted shRNA (shRNAmirs).

5.1.1 microRNA

In certain embodiments, the methods provided herein for the production of enhanced placental stem cells comprise contacting placental stem cells with an effective amount of microRNAs or microRNA mimics, such that an ability to exhibit increased survival in conditions that normally cause cell death in said placental stem cells is conferred, e.g., as compared to placental stem cells that have not been modified, e.g., that have not been contacted with the microRNAs or microRNA mimics. As used herein, the term "microRNA," "miRNA," or "miR" refers to short ribonucleic acid (RNA) molecules, including, but not limited to, mature single stranded miRNAs, precursor miRNAs (pre-miR), and variants thereof. In some embodiments, the miR inhibitors downregulate (e.g., inhibit) a target gene by inhibition of one or more endogenous miRs. In one embodiment, the microRNAs are naturally occurring. In certain embodiments, the microRNAs are post-transcriptional regulators that bind to complementary sequences on target messenger RNA transcripts (mRNAs) and result in translational repression and gene silencing. In certain embodiments, a single precursor miRNA contains more than one mature miRNA sequence. In other embodiments, multiple precursor miRNAs contain the same mature sequence. Generally, precursor miRNA exists as a hairpin loop structure, with each hairpin flanked by sequences necessary for efficient processing. The precursor thus possesses one strand ("arm") that results in expressed miRNA and an opposite strand ("arm"). In some embodiments, when the relative abundances clearly indicate which is the predominantly expressed miRNA, the term "microRNA," "miRNA," or "miR" refers to the predominant product, and the term "microRNA*," "miRNA*," or "miR*" refers to the opposite arm of the precursor. In one embodiment, miRNA is the "guide" strand that eventually enters RNA-Induced Silencing Complex (RISC), and miRNA* is the other "passenger" strand. In another embodiment, the level of miRNA* present in the cell at a lower level (e.g., <15%) relative to the corresponding miRNA. In some embodiments where there is a higher proportion of passenger strand present in the cell, the nomenclature miRNA-3p (i.e., miRNA derived from the 3' arm of the precursor miRNA) and miRNA-5p (i.e., miRNA-5p is the miRNA derived from the 5' arm of the precursor miRNA) is used instead of miRNA/miRNA*.

As used herein, the term "microRNA mimic(s)" or "miR mimic(s)" refers to molecules that can be used to imitate or mimic the gene silencing ability of one or more miRNAs. In one embodiment, the miR mimics down-regulate (e.g., inhibit) a target gene by imitating one or more endogenous miRs. In certain embodiments, miRNA mimics are synthetic non-coding RNAs (i.e., the miRNA is not obtained by purification from a source of the endogenous miRNA). In certain embodiments, the miRNA mimics are capable of entering the RNAi pathway and regulating gene expression. In certain embodiments, miRNA mimics can be designed as mature molecules (e.g. single stranded) or mimic precursors (e.g., pri- or pre-miRNAs).

In some embodiments, the microRNAs or miRNA mimics provided herein comprise nucleic acid (modified or modified nucleic acids) including oligonucleotides comprising, e.g., RNA, DNA, modified RNA, modified DNA, locked nucleic acids, or 2'-O,4'-C-ethylene-bridged nucleic acids (ENA), or any combination of thereof.

The microRNAs or miR mimics can be single-stranded or double-stranded, and can be modified or unmodified. In certain embodiments, the microRNAs or miR mimics have a length of about 2 to about 30 nucleobases. In certain embodiments, the microRNAs or miR mimics are single-stranded, and have a length of about 15 to about 30 nucleobases. In some embodiments, the microRNAs are single-stranded, and are about 15, 16, 17, 18, 19, 20, 21, 22, 23, 24, 25, 26, 27, 28, 29 or 30 nucleobases in length.

In a specific embodiment, microRNA that can be used to generate enhanced placental stem cells in accordance with the methods described herein is a microRNA listed in Table 2, above (or a microRNA mimic thereof). In another specific embodiment, more than one of the microRNAs listed in Table 2, above, can be used to generate enhanced placental stem cells in accordance with the methods described herein. In another specific embodiment, the microRNA used to generate enhanced placental stem cells in accordance with the methods described herein is miR-16, miR-29a, miR-424, miR-4305, miR-3142, and/or miR-613. In another specific embodiment, the microRNA used to generate enhanced placental stem cells in accordance with the methods described herein is miR-16. In another specific embodiment, the microRNA used to generate enhanced placental stem cells in accordance with the methods described herein is miR-29a. In another specific embodiment, the microRNA used to generate enhanced placental stem cells in accordance with the methods described herein is miR-424.

In a specific embodiment, provided herein is a method of producing enhanced placental stem cells, comprising contacting a placental stem cell, or population thereof, with one or more microRNAs or miR mimics that target one or more genes identified herein as being associated with survival in placental stem cells (e.g., one or more of the genes identified in Table 1, above).

In another specific embodiment, the miRNAs or miRNA mimics used in the methods described herein for generating enhanced placental stem cells target the placental stem cell survival-associated gene CCND1. In another specific embodiment, the miRNAs or miRNA mimics used in the methods described herein for generating enhanced placental stem cells target the placental stem cell survival-associated gene CCND3. In another specific embodiment, the miRNAs or miRNA mimics used in the methods described herein for generating enhanced placental stem cells target the placental stem cell survival-associated gene CCNE1. In another specific embodiment, the miRNAs or miRNA mimics used in the methods described herein for generating enhanced placental stem cells target the placental stem cell survival-associated gene CCNF. In another specific embodiment, the miRNAs or miRNA mimics used in the methods described herein for generating enhanced placental stem cells target the placental stem cell survival-associated gene CDK6. In another specific embodiment, the miRNAs or miRNA mimics used in the methods described herein for generating enhanced placental stem cells target the placental stem cell survival-associated gene PPP2R5C. In another specific embodiment, the miRNAs or miRNA mimics used in the methods described herein for generating enhanced placental stem cells target the placental stem cell survival-associated gene CDC25A. In another specific embodiment, the miRNAs or miRNA mimics used in the methods described herein for generating enhanced placental stem cells target the placental stem cell survival-associated gene WEE1. In another specific embodiment, the miRNAs or miRNA mimics used in the methods described herein for generating enhanced placental stem cells target the placental stem cell survival-associated gene CHEK1. In another specific embodiment, the miRNAs or miRNA mimics used in the methods described herein for generating enhanced placental stem cells target the placental stem cell survival-associated gene MCL1. In another specific embodiment, the miRNAs or miRNA mimics used in the methods described herein for generating enhanced placental stem cells target the placental stem cell survival-associated gene BCL2. In another specific embodiment, the miRNAs or miRNA mimics used in the methods described herein for generating enhanced placental stem cells target the placental stem cell survival-associated gene PPMID. In another specific embodiment, the miRNAs or miRNA mimics used in the methods described herein for generating enhanced placental stem cells target the placental stem cell survival-associated gene HMGA1. In another specific embodiment, the miRNAs or miRNA mimics used in the methods described herein for generating enhanced placental stem cells target the placental stem cell survival-associated gene AKT3. In another specific embodiment, the miRNAs or miRNA mimics used in the methods described herein for generating enhanced placental stem cells target the placental stem cell survival-associated gene VEGFA. In another specific embodiment, the miRNAs or miRNA mimics used in the methods described herein for generating enhanced placental stem cells target the placental stem cell survival-associated gene MYB. In another specific embodiment, the miRNAs or miRNA mimics used in the methods described herein for generating enhanced placental stem cells target the placental stem cell survival-associated gene ITGA2.

In another specific embodiment, the miRNAs or miRNA mimics used in the methods described herein for generating enhanced placental stem cells target two, three, or more (i.e., a combination) of the following placental stem cell survival-associated genes: CCND1, CCND3, CCNE1, CCNF, CDK6, PPP2R5C, CDC25A, WEE1, CHEK1, MCL1, BCL2, PPMID, HMGA1, AKT3, VEGFA, MYB, and/or ITGA2.

In another specific embodiment, contacting of a survival-associated gene of a placental stem cell (e.g., a gene listed in Table 1, above) with miRNAs or miRNA mimics results in a decrease in the mRNA level of said gene in said placental stem cell, e.g., the mRNA level of the survival-associated gene in the resulting enhanced placental stem cells is decreased relative to the mRNA level of the same gene in unmodified placental stem cells (i.e., placental stem cells not contacted with a miRNA or miRNA mimic). In certain embodiments, the mRNA level of a survival-associated gene in an enhanced placental stem cell produced according to the methods described herein is decreased about, up to, or no more than, 5%, 10%, 15%, 20%, 25%, 30%, 35%, 40%, 45%, 50%, 55%, 60%, 65%, 70%, 75%, 80%, 85%, 90%, 95%, 98% or 99%, e.g., as compared to the expression of said gene (mRNA level) in unmodified placental stem cells.

In another specific embodiment, contacting of a survival-associated gene of a placental stem cell (e.g., a gene listed in Table 1, above) with miRNAs or miRNA mimics results in an increase in the mRNA level of said gene in said placental stem cell, e.g., the mRNA level of the survival-associated gene in the resulting enhanced placental stem cells is increased relative to the mRNA level of the same gene in unmodified placental stem cells (i.e., placental stem cells not contacted with a miRNA or miRNA mimic). In certain embodiments, the mRNA level of a survival-associated gene in an enhanced placental stem cell produced according to the methods described herein is increased about, up to, or no more than, 5%, 10%, 15%, 20%, 25%, 30%, 35%, 40%, 45%, 50%, 55%, 60%, 65%, 70%, 75%, 80%, 85%, 90%, 95%, 98% or 99%, e.g., as compared to the expression of said gene (mRNA level) in unmodified placental stem cells.

The miRNAs or miRNA mimics used in the methods described herein can be supplied by a commercial vendor (e.g., Ambion; Dharmafect), or can be synthesized by, e.g., solid phase synthesis, or according to the procedures as described in, e.g., Protocols for Oligonucleotides and Analogs, Ed. Agrawal (1993), Humana Press; Scaringe, Methods (2001), 23, 206-217. Gait et al., Applications of Chemically synthesized RNA in RNA: Protein Interactions, Ed. Smith (1998), 1-36. Gallo et al., Tetrahedron (2001), 57, 5707-5713).

The miRNAs or miRNA mimics used in the methods described herein can be identified by a variety of methods known in the art. In certain embodiments, such miRNAs or miRNA mimics are identified and obtained from one or more miRNA or miRNA mimic libraries, e.g., a commercially available library (e.g., Ambion, Anti-miR miRNA Precursor Library Human V13), optionally by a screening method, e.g., medium or high-throughput screening. In one embodiment, such a library can encompass a wide range of target genes or gene families. The screening method can be carried out, for example, using automated robotics, liquid handling equipments, data processing software, and/or sensitive detectors, e.g., Precision XS Automated Pipettor System, EL406 liquid handling system, or synergy plate reader.

5.1.2 siRNAs

In certain embodiments, the methods provided herein for the production of enhanced placental stem cells comprise contacting placental stem cells with an effective amount of small interfering RNAs (siRNAs), such that an ability to exhibit increased survival in conditions that normally cause cell death in said placental stem cells is conferred, e.g., as compared to placental stem cells that have not been modified, e.g., that have not been contacted with siRNAs. As used herein, the term "small interfering RNA" or "siRNA" is well known in the art and refers to an RNA molecule that interferes with the expression of a specific gene.

The siRNAs used in the methods described herein can be single-stranded or double-stranded, and can be modified or unmodified. In one embodiment, the siRNAs used in the methods described herein have one or more 2'-deoxy or 2'-O-modified bases. In some embodiments, the siRNAs used in the methods described herein have one or more base substitutions and inversions (e.g., 3-4 nucleobases inversions).

In some embodiments, the siRNAs used in the methods described herein are double-stranded. In one embodiment, one strand of the siRNA is antisense to the target nucleic acid, while the other strand is complementary to the first strand. In certain embodiments, said siRNAs comprise a central complementary region between the first and second strands and terminal regions that are optionally complementary between said first and second strands or with the target RNA.

In certain embodiments, the siRNAs used in the methods described herein have a length of about 2 to about 50 nucleobases. In some embodiments, the siRNAs used in the methods described herein are double-stranded, and have a length of about 5 to 45, about 7 to 40, or about 10 to about 35 nucleobases. In some embodiments, the siRNAs used in the methods described herein are double-stranded, and are about 10, 11, 12, 13, 14, 15, 16, 17, 18, 19, 20, 21, 22, 23, 24, 25, 26, 27, 28, 29, 30, 31, 32, 33, 34, or 35 nucleobases in length.

In certain embodiments, one or both ends of the first and/or second strands of the siRNAs used in the methods described herein are modified by adding one or more natural or modified nucleobases to form an overhang. In certain embodiments, one or both ends of the first and/or second strands of the siRNAs used in the methods described herein are blunt. It is possible for one end of the first and/or second strands of the siRNAs used in the methods described herein to be blunt and the other to have overhanging nucleobases. In one embodiment, said overhangs are about 1 to about 10, about 2 to about 8, about 3 to about 7, about 4 to about 6 nucleobase(s) in length. In another embodiment, said overhangs are about 1, 2, 3, 4, 5, 6, 7, 8, 9, or 10 nucleobase(s) in length. In a specific embodiment, the siRNAs used in the methods described herein are double-stranded, and have a length of about 21 nucleobases. In another specific embodiment, the siRNAs are double-stranded, and have a length of about 21 nucleobases comprising dinucleotide 3' overhangs (e.g., dinucleotide 3' DNA overhangs such as UU or TT 3'-overhangs) such that there is a 19 nt complementary region between the sense and anti-sense strands.

In a specific embodiment, provided herein is a method of producing enhanced placental stem cells, comprising contacting a placental stem cell, or population thereof, with one or more siRNAs that target one or more genes identified herein as being associated with survival in placental stem cells (e.g., one or more of the genes identified in Table 1, above). In one embodiment, said siRNAs are double-stranded. In a specific embodiment, one strand (e.g., sense strand) of said double-stranded siRNAs has a sequence at least about 70%, 80%, 90%, 95%, 98% or 100% complementary to the sequence of one of the genes identified in Table 1, above (as identified based on the Gene ID of the gene provided in the table).

In another specific embodiment, the siRNAs used in the methods described herein for generating enhanced placental stem cells target the placental stem cell survival-associated gene CCND1. In another specific embodiment, the siRNAs used in the methods described herein for generating enhanced placental stem cells target the placental stem cell survival-associated gene CCND3. In another specific embodiment, the siRNAs used in the methods described herein for generating enhanced placental stem cells target the placental stem cell survival-associated gene CCNE1. In another specific embodiment, the siRNAs used in the methods described herein for generating enhanced placental stem cells target the placental stem cell survival-associated gene CCNF. In another specific embodiment, the siRNAs used in the methods described herein for generating enhanced placental stem cells target the placental stem cell survival-associated gene CDK6. In another specific embodiment, the siRNAs used in the methods described herein for generating enhanced placental stem cells target the placental stem cell survival-associated gene PPP2R5C. In another specific embodiment, the siRNAs used in the methods described herein for generating enhanced placental stem cells target the placental stem cell survival-associated gene CDC25A. In another specific embodiment, the siRNAs used in the methods described herein for generating enhanced placental stem cells target the placental stem cell survival-associated gene WEE1. In another specific embodiment, the siRNAs used in the methods described herein for generating enhanced placental stem cells target the placental stem cell survival-associated gene CHEK1. In another specific embodiment, the siRNAs used in the methods described herein for generating enhanced placental stem cells target the placental stem cell survival-associated gene MCL1. In another specific embodiment, the siRNAs used in the methods described herein for generating enhanced placental stem cells target the placental stem cell survival-associated gene BCL2. In another specific embodiment, the siRNAs used in the methods described herein for generating enhanced placental stem cells target the placental stem cell survival-associated gene PPMID. In another specific embodiment, the siRNAs used in the methods described herein for generating enhanced placental stem cells target the placental stem cell survival-associated gene HMGA1. In another specific embodiment, the siRNAs used in the methods described herein for generating enhanced placental stem cells target the placental stem cell survival-associated gene AKT3. In another specific embodiment, the siRNAs used in the methods described herein for generating enhanced placental stem cells target the placental stem cell survival-associated gene VEGFA. In another specific embodiment, the siRNAs used in the methods described herein for generating enhanced placental stem cells target the placental stem cell survival-associated gene MYB. In another specific embodiment, the siRNAs used in the methods described herein for generating enhanced placental stem cells target the placental stem cell survival-associated gene ITGA2.

In another specific embodiment, the siRNAs used in the methods described herein for generating enhanced placental stem cells target two, three, or more (i.e., a combination) of the following placental stem cell survival-associated genes: CCND1, CCND3, CCNE1, CCNF, CDK6, PPP2R5C, CDC25A, WEE1, CHEK1, MCL1, BCL2, PPMID, HMGA1, AKT3, VEGFA, MYB, and/or ITGA2.

In another specific embodiment, contacting of a survival-associated gene of a placental stem cell with siRNAs results in a decrease in the mRNA level of said gene in said placental stem cell, e.g., the mRNA level of the survival-associated gene in the resulting enhanced placental stem cells is decreased relative to the mRNA level of the same gene in unmodified placental stem cells (i.e., placental stem cells not contacted with an siRNA). In certain embodiments, the mRNA level of a survival-associated gene in an enhanced placental stem cell produced according to the methods described herein is decreased about, up to, or no more than, 5%, 10%, 15%, 20%, 25%, 30%, 35%, 40%, 45%, 50%, 55%, 60%, 65%, 70%, 75%, 80%, 85%, 90%, 95%, 98% or 99%, e.g., as compared to the expression of said gene (mRNA level) in unmodified placental stem cells.

The siRNAs used in the methods described herein can be supplied by a commercial vendor (e.g., Ambion; Dharmacon), or be synthesized by, e.g., solid phase synthesis, or according to the procedures as described in, e.g., Protocols for Oligonucleotides and Analogs, Ed. Agrawal (1993), Humana Press; Scaringe, Methods (2001), 23, 206-217. Gait et al., Applications of Chemically synthesized RNA in RNA: Protein Interactions, Ed. Smith (1998), 1-36. Gallo et al., Tetrahedron (2001), 57, 5707-5713).

siRNAs useful for the production of enhanced placental stem cells can be identified by a variety of methods known in the art. In certain embodiments, such siRNAs are identified and obtained from one or more siRNA libraries, e.g., a commercially available library (e.g., Ambion, Silencer® Select Human Nuclear Hormone Receptor (HNR) siRNA Library V4; Dharmacon, siRNA library Human ON-TARGETplus siRNA Nuclear Receptors Sub-Library), optionally by a screening method, e.g., medium or high-throughput screening. In one embodiment, such a library can encompass a wide range of genes (e.g., human genome-wide siRNA library), or pre-defined to encompass specific target genes or gene families (e.g., human nuclear receptor siRNA library, phosphatase siRNA library, etc.). The screening method can be carried out, for example, using automated robotics, liquid handling equipments, data processing software, and/or sensitive detectors, e.g., Precision XS Automated Pipettor System, EL406 liquid handling system, or synergy plate reader.

5.1.3 Other Molecules

Other oligomeric or polymeric molecules useful for the production of enhanced placental stem cells include, for example, antisense RNAs, antisense DNAs, shRNAs, and shRNAmirs. In certain embodiments, these molecules can be used in any combination with one another and also can be used in combination with siRNAs, miR mimics and/or miR inhibitors to produce the enhanced placental stem cells as described herein.

As used herein, the term "antisense RNA" is an antisense ribonucleic acid molecule. By illustration only and without limitation, antisense RNAs hybridize to a target nucleic acid (e.g., a gene or mRNA) and modulate expression activities of the target nucleic acid, such as transcription or translation.

As used herein, the term "antisense DNA" is an antisense deoxyribonucleic acid molecule. Antisense DNA refers to a DNA sequence that has a nucleotide sequence complementary to the "sense strand" of a gene when read in reverse orientation. By illustration only and without limitation, antisense DNAs hybridize to a target nucleic acid (e.g., a gene or mRNA) and modulate expression activities of the target nucleic acid, such as transcription or translation.

As used herein, the term "small hairpin RNA" or "shRNA" refers to an RNA molecule comprising a stem-loop structure; the term "shRNAmir" refers to "microRNA-adapted shRNA." In certain embodiments, said shRNA comprises a first and second region of complementary sequence, the degree of complementarity and orientation of the regions being sufficient such that base pairing occurs between the regions, the first and second regions being joined by a loop region, the loop resulting from a lack of base pairing between nucleotides (or nucleotide analogs) within the loop region. The shRNA hairpin structure can be, for example, cleaved by the cellular machinery into siRNA, which is then bound to the RNA-induced silencing complex (RISC). This complex binds to and cleaves mRNAs which match the siRNA that is bound to it.

In some embodiments, shRNAmirs provided herein are shRNA constructs that mimic naturally occurring primary transcript miRNA with the addition of an miRNA loop and a miRNA flanking sequence to a shRNA. Without wishing to be bound by any theory, the shRNAmir is first cleaved to produce shRNA by Drosha, and then cleaved again by Dicer to produce siRNA. The siRNA is then incorporated into the RISC for target mRNA degradation. This allows the shRNAmir to be cleaved by Drosha thereby allowing for a greater increase in knockdown efficiency. The addition of a miR30 loop and 125 nt of miR30 flanking sequence on either side of the shRNA hairpin has been reported to result in greater than 10-fold increase in Drosha and Dicer processing of the expressed hairpins when compared with conventional shRNA constructs without microRNA.

In a specific embodiment, provided herein is a method of producing enhanced placental stem cells, comprising contacting a placental stem cell, or population thereof, with one or more antisense RNAs, antisense DNAs, shRNAs, and shRNAmirs that target one or more genes survival-associated genes, e.g., one or more genes listed in Table 1, above.

In another specific embodiment, the modulatory RNA molecules used in the methods described herein for generating enhanced placental stem cells are small hairpin RNAs or shRNAs. In a specific embodiment, said shRNAs target one or more of the survival-associated genes listed in Table 1, above. In another specific embodiment, said shRNAs target at least two, at least 3, at least 4, or at least 5 of the genes listed in Table 1, above. In another specific embodiment, said shRNAs have a sequence at least about 70%, 80%, 90%, 95%, 98% or 100% complementary to the sequence of one of the genes identified in Table 1, above (as identified based on the Gene ID of the gene provided in the table).

In another specific embodiment, the modulatory RNA molecules used in the methods described herein for generating enhanced placental stem cells are antisense RNAs. In a specific embodiment, said antisense RNAs target one or more of the survival-associated genes listed in Table 1, above. In another specific embodiment, said antisense RNAs target at least two, at least 3, at least 4, or at least 5 of the genes listed in Table 1, above. In another specific embodiment, said antisense RNAs have a sequence at least about 70%, 80%, 90%, 95%, 98% or 100% complementary to the sequence of one of the genes identified in Table 1, above (as identified based on the Gene ID of the gene provided in the table).

In another specific embodiment, the molecules used in the methods described herein for generating enhanced placental stem cells are antisense DNAs. In a specific embodiment, said antisense DNAs target one or more of the survival-associated genes listed in Table 1, above. In another specific embodiment, said antisense DNAs target at least two, at least 3, at least 4, or at least 5 of the genes listed in Table 1, above. In another specific embodiment, said antisense DNAs have a sequence at least about 70%, 80%, 90%, 95%, 98% or 100% complementary to the sequence of one of the genes identified in Table 1, above (as identified based on the Gene ID of the gene provided in the table).

In another specific embodiment, the shRNAs used in the methods described herein for generating enhanced placental stem cells target the placental stem cell survival-associated gene CCND1. In another specific embodiment, the shRNAs used in the methods described herein for generating enhanced placental stem cells target the placental stem cell survival-associated gene CCND3. In another specific embodiment, the shRNAs used in the methods described herein for generating enhanced placental stem cells target the placental stem cell survival-associated gene CCNE1. In another specific embodiment, the shRNAs used in the methods described herein for generating enhanced placental stem cells target the placental stem cell survival-associated gene CCNF. In another specific embodiment, the shRNAs used in the methods described herein for generating enhanced placental stem cells target the placental stem cell survival-associated gene CDK6. In another specific embodiment, the shRNAs used in the methods described herein for generating enhanced placental stem cell survival-associated gene PPP2R5C. In another specific embodiment, the shRNAs used in the methods described herein for generating enhanced placental stem cells target the placental stem cell survival-associated gene CDC25A. In another specific embodiment, the shRNAs used in the methods described herein for generating enhanced placental stem cells target the placental stem cell survival-associated gene WEE1. In another specific embodiment, the shRNAs used in the methods described herein for generating enhanced placental stem cells target the placental stem cell survival-associated gene CHEK1. In another specific embodiment, the shRNAs used in the methods described herein for generating enhanced placental stem cell survival-associated gene MCL1. In another specific embodiment, the shRNAs used in the methods described herein for generating enhanced placental stem cells target the placental stem cell survival-associated gene BCL2. In another specific embodiment, the shRNAs used in the methods described herein for generating enhanced placental stem cells target the placental stem cell survival-associated gene PPMID. In another specific embodiment, the shRNAs used in the methods described herein for generating enhanced placental stem cells target the placental stem cell survival-associated gene HMGA1. In another specific embodiment, the shRNAs used in the methods described herein for generating enhanced placental stem cells target the placental stem cell survival-associated gene AKT3. In another specific embodiment, the shRNAs used in the methods described herein for generating enhanced placental stem cells target the placental stem cell survival-associated gene VEGFA. In another specific embodiment, the shRNAs used in the methods described herein for generating enhanced placental stem cells target the placental stem cell survival-associated gene MYB. In another specific embodiment, the shRNAs used in the methods described herein for generating enhanced placental stem cells target the placental stem cell survival-associated gene ITGA2.

In another specific embodiment, the shRNAs used in the methods described herein for generating enhanced placental stem cells target two, three, or more (i.e., a combination) of the following placental stem cell survival-associated genes: CCND1, CCND3, CCNE1, CCNF, CDK6, PPP2R5C, CDC25A, WEE1, CHEK1, MCL1, BCL2, PPMID, HMGA1, AKT3, VEGFA, MYB, and/or ITGA2.

In another specific embodiment, the antisense RNAs used in the methods described herein for generating enhanced placental stem cells target the placental stem cell survival-associated gene CCND1. In another specific embodiment, the antisense RNAs used in the methods described herein for generating enhanced placental stem cell survival-associated gene CCND3. In another specific embodiment, the antisense RNAs used in the methods described herein for generating enhanced placental stem cells target the placental stem cell survival-associated gene CCNE1. In another specific embodiment, the antisense RNAs used in the methods described herein for generating enhanced placental stem cells target the placental stem cell survival-associated gene CCNF. In another specific embodiment, the antisense RNAs used in the methods described herein for generating enhanced placental stem cells target the placental stem cell survival-associated gene CDK6. In another specific embodiment, the antisense RNAs used in the methods described herein for generating enhanced placental stem cells target the placental stem cell survival-associated gene PPP2R5C. In another specific embodiment, the antisense RNAs used in the methods described herein for generating enhanced placental stem cells target the placental stem cell survival-associated gene CDC25A. In another specific embodiment, the antisense RNAs used in the methods described herein for generating enhanced placental stem cells target the placental stem cell survival-associated gene WEE1. In another specific embodiment, the antisense RNAs used in the methods described herein for generating enhanced placental stem cells target the placental stem cell survival-associated gene CHEK1. In another specific embodiment, the antisense RNAs used in the methods described herein for generating enhanced placental stem cells target the placental stem cell survival-associated gene MCL1. In another specific embodiment, the antisense RNAs used in the methods described herein for generating enhanced placental stem cells target the placental stem cell survival-associated gene BCL2. In another specific embodiment, the antisense RNAs used in the methods described herein for generating enhanced placental stem cells target the placental stem cell survival-associated gene PPMID. In another specific embodiment, the antisense RNAs used in the methods described herein for generating enhanced placental stem cells target the placental stem cell survival-associated gene HMGA1. In another specific embodiment, the antisense RNAs used in the methods described herein for generating enhanced placental stem cells target the placental stem cell survival-associated gene AKT3. In another specific embodiment, the antisense RNAs used in the methods described herein for generating enhanced placental stem cells target the placental stem cell survival-associated gene VEGFA. In another specific embodiment, the antisense RNAs used in the methods described herein for generating enhanced placental stem cells target the placental stem cell survival-associated gene MYB. In another specific embodiment, the antisense RNAs used in the methods described herein for generating enhanced placental stem cells target the placental stem cell survival-associated gene ITGA2.

In another specific embodiment, the antisense RNAs used in the methods described herein for generating enhanced placental stem cells target two, three, or more (i.e., a combination) of the following placental stem cell survival-associated genes: CCND1, CCND3, CCNE1, CCNF, CDK6, PPP2R5C, CDC25A, WEE1, CHEK1, MCL1, BCL2, PPMID, HMGA1, AKT3, VEGFA, MYB, and/or ITGA2.

In another specific embodiment, the antisense DNAs used in the methods described herein for generating enhanced placental stem cells target the placental stem cell survival-associated gene CCND1. In another specific embodiment, the antisense DNAs used in the methods described herein for generating enhanced placental stem cells target the placental stem cell survival-associated gene CCND3. In another specific embodiment, the antisense DNAs used in the methods described herein for generating enhanced placental stem cells target the placental stem cell survival-associated gene CCNE1. In another specific embodiment, the antisense DNAs used in the methods described herein for generating enhanced placental stem cells target the placental stem cell survival-associated gene CCNF. In another specific embodiment, the antisense DNAs used in the methods described herein for generating enhanced placental stem cells target the placental stem cell survival-associated gene CDK6. In another specific embodiment, the antisense DNAs used in the methods described herein for generating enhanced placental stem cells target the placental stem cell survival-associated gene PPP2R5C. In another specific embodiment, the antisense DNAs used in the methods described herein for generating enhanced placental stem cells target the placental stem cell survival-associated gene CDC25A. In another specific embodiment, the antisense DNAs used in the methods described herein for generating enhanced placental stem cells target the placental stem cell survival-associated gene WEE1. In another specific embodiment, the antisense DNAs used in the methods described herein for generating enhanced placental stem cells target the placental stem cell survival-associated gene CHEK1. In another specific embodiment, the antisense DNAs used in the methods described herein for generating enhanced placental stem cells target the placental stem cell survival-associated gene MCL1. In another specific embodiment, the antisense DNAs used in the methods described herein for generating enhanced placental stem cells target the placental stem cell survival-associated gene BCL2. In another specific embodiment, the antisense DNAs used in the methods described herein for generating enhanced placental stem cells target the placental stem cell survival-associated gene PPMID. In another specific embodiment, the antisense DNAs used in the methods described herein for generating enhanced placental stem cells target the placental stem cell survival-associated gene HMGA1. In another specific embodiment, the antisense DNAs used in the methods described herein for generating enhanced placental stem cells target the placental stem cell survival-associated gene AKT3. In another specific embodiment, the antisense DNAs used in the methods described herein for generating enhanced placental stem cells target the placental stem cell survival-associated gene VEGFA. In another specific embodiment, the antisense DNAs used in the methods described herein for generating enhanced placental stem cells target the placental stem cell survival-associated gene MYB. In another specific embodiment, the antisense DNAs used in the methods described herein for generating enhanced placental stem cells target the placental stem cell survival-associated gene ITGA2.

In another specific embodiment, the antisense DNAs used in the methods described herein for generating enhanced placental stem cells target two, three, or more (i.e., a combination) of the following placental stem cell survival-associated genes: CCND1, CCND3, CCNE1, CCNF, CDK6, PPP2R5C, CDC25A, WEE1, CHEK1, MCL1, BCL2, PPMID, HMGA1, AKT3, VEGFA, MYB, and/or ITGA2.

In another specific embodiment, contacting of a survival-associated gene of a placental stem cell with an shRNA or antisense RNA results in a decrease in the mRNA level of said gene in said placental stem cell, e.g., the mRNA level of the survival-associated gene in the resulting enhanced placental stem cells is decreased relative to the mRNA level of the same gene in unmodified placental stem cells (i.e., placental stem cells not contacted with an shRNA or antisense RNA). In certain embodiments, the mRNA level of a survival-associated gene in an enhanced placental stem cell produced according to the methods described herein is decreased about, up to, or no more than, 5%, 10%, 15%, 20%, 25%, 30%, 35%, 40%, 45%, 50%, 55%, 60%, 65%, 70%, 75%, 80%, 85%, 90%, 95%, 98% or 99%, e.g., as compared to the expression of said gene (mRNA level) in unmodified placental stem cells.

The antisense RNAs, antisense DNAs, shRNAs and shRNAmirs used in the methods described herein can be supplied by a commercial vendor (e.g., Ambion; Dharmafect), or can be synthesized by, e.g., solid phase synthesis, or according to the procedures as described in, e.g., Protocols for Oligonucleotides and Analogs, Ed. Agrawal (1993), Humana Press; Scaringe, Methods (2001), 23, 206-217. Gait et al., Applications of Chemically synthesized RNA in RNA: Protein Interactions, Ed. Smith (1998), 1-36. Gallo et al., Tetrahedron (2001), 57, 5707-5713).

Antisense RNAs, antisense DNAs, shRNAs, shRNAmirs and other molecules useful for the production of enhanced placental stem cells can be identified by a variety of methods known in the art. In certain embodiments, such antisense RNAs, antisense DNAs, shRNAs, shRNAmirs and other modulatory molecules (e.g., modulatory RNA molecules) are identified and obtained from one or more libraries, e.g., a commercially available library (Thermo Scientific, shRNAmir libraries), optionally by a screening method, e.g., medium or high-throughput screening. In one embodiment, such a library can encompass a wide range of genes (e.g., human genome targeted library), or pre-defined to encompass specific target genes or gene families (e.g., human nuclear receptor targeted library, phosphatase targeted library, etc.). The screening method can be carried out, for example, using automated robotics, liquid handling equipments, data processing software, and/or sensitive detectors, e.g., Precision XS Automated Pipettor System, EL406 liquid handling system, or synergy plate reader.

In certain embodiments, the antisense RNAs, antisense DNAs, shRNAs and shRNAmirs used in the methods described herein comprise about 8 to about 100, from about 8 to about 80, 10 to 50, 13 to 80, 13 to 50, 13 to 30, 13 to 24, 18 to 22, 19 to 23, 20 to 80, 20 to 50, 20 to 30, or 20 to 24 nucleobases (nucleobases (i.e. from about 1 to about 100 linked nucleosides).

The antisense RNAs, antisense DNAs, shRNAs and shRNAmirs used in the methods described herein can be single-stranded or double-stranded, modified or unmodified. In certain embodiments, said antisense RNAs, antisense DNAs, miR mimics, shRNAs, shRNAmirs and other modulatory RNA molecules comprise about 1 to about 100, from about 8 to about 80, 10 to 50, 13 to 80, 13 to 50, 13 to 30, 13 to 24, 18 to 22, 19 to 23, 20 to 80, 20 to 50, 20 to 30, or 20 to 24 nucleobases (i.e. from about 1 to about 100 linked nucleosides). In certain embodiment, the antisense RNAs, antisense DNAs, shRNAs and shRNAmirs used in the methods described herein are single-stranded, comprising from about 12 to about 35 nucleobases (i.e. from about 12 to about 35 linked nucleosides). In one embodiment, the antisense RNAs, antisense DNAs, miR mimics, shRNAs and shRNAmirs used in the methods described herein are about 10, 11, 12, 13, 14, 15, 16, 17, 18, 19, 20, 21, 22, 23, 24, 25, 26, 27, 28, 29, 30, 31, 32, 33, 34, or 35 nucleobases in length.

The shRNAmirs used in the methods described herein can be delivered to the cells by any known method. In a specific embodiment, an shRNAmir used in the methods described herein is incorporated into a eukaryotic expression vector. In another specific embodiment, an shRNAmir used in the methods described herein is incorporated into a viral vector for gene expression. Such viral vectors include, but are not limited to, retroviral vectors, e.g., lentivirus, and adenoviruses. In a specific embodiment, an shRNAmir used in the methods described herein is incorporated into a lentiviral vector.

5.1.4 Delivery of Modulatory Molecules to Placental Stem Cells

The modulatory oligomeric or polymeric molecules used in the methods described herein can be delivered to placental stem cells by transfection (e.g., transient or stable transfection) or other means known in the art. In certain embodiments, said transfection can be carried out, e.g., using lipids (e.g., liposomes), calcium phosphate, cyclodextrin, dendrimers, or polymers (e.g., cationic polymers); by electroporation, optical transfection, gene electrotransfer, impalefection, gene gun, or magnetofection; via viruses (e.g., viral carriers); or a combination thereof. In one embodiment, said transfection is performed using commercially available transfection reagents or kits (e.g., Ambion, siPORT™ Amine, siPORT NeoFX's; Dharmafect, Dharmafect 3 Transfection Reagent or Dharmafect 1 Transfection Reagent; Invitrogen, Lipofectamine RNAiMAX; Integrated DNA Technologies, Transductin; Minis Bio LLC, TransIT-siQUEST, TransIT-TKO). In a specific embodiment, said transfection can be carried out using Dharmacon ON-TARGET plus SMARTpool® siRNA reagents with the Dharmafect 1 Transfection Reagent. In some embodiments, said transfection can be set up in a medium or high-throughput manner, including, but not limited to, use of microtiter plate (e.g., 96-well plate) and microplate reader (e.g., synergy plate reader), or automation system, for example, Precision XS Automated Pipettor System, EL406 liquid handling system. In other embodiments, said transfection is set up in a large scale, including, but not limited to, the use of tissue culture dishes or culture flasks (e.g., T25, T75, or T225 flasks). Placental stem cells can be plated and cultured in tissue culture containers, e.g., dishes, flasks, multiwell plates, or the like, for a sufficient time for the placental stem cells to proliferate to about 20-80% confluence, or about 30-70% confluence at the time of transfection. For example, there can be about 2000, 2500, 3000, 3500, or 4000 placental stem cells per well in a 96-well plate at the time of transfection. In one embodiment, placental stem cells are at about 50% confluence at the time of transfection. In another embodiment, there are about 3000 or 3500 placental stem cells per well in a 96-well plate at the time of transfection. In another embodiment, there are about 3500 placental stem cells per well in a 96-well plate at the time of transfection.

The modulatory oligomeric or polymeric molecules used in the methods described herein can, for example, be administered to the cells via transient or stable transfection. In one embodiment, stable transfection of modulatory oligomeric or polymeric molecules can be carried out, for example, by the use of plasmids or expression vectors that express functional modulatory oligomeric or polymeric molecules. In one embodiment, such plasmids or expression vectors comprise a selectable marker (e.g., an antibiotic selection marker). In another embodiment, such plasmids or expression vectors comprise a cytomegalovirus (CMV) promoter, an RNA polymerase III (RNA pol III) promoter (e.g., U6 or H1), or an RNA polymerase II (RNA pol II) promoter.

In certain embodiments, the plasmids or expression vectors used in accordance with the methods described herein are commercially available (e.g., Ambion, pSilencer™ 4.1-CMV vector). Other examples of mammalian expression vectors include pLOC (Open Biosystems), which contains a cytomegalovirus promoter; pCDM8 (Seed, Nature 329:840 (1987)) and pMT2PC (Kaufman et al., EMBO J. 6:187-195 (1987)). Other example expression vectors that may be used include pFN10A (ACT) FLEXI® Vector (Promega), pFN11A (BIND) FLEXI® Vector (Promega), pGL4.31 [luc2P/GAL4UAS/Hygro] (Promega), pFC14K (HALOTAG® 7) MCV FLEXI® Vector (Promega), pFC15A (HALOTAG® 7) MCV FLEXI® Vector (Promega), and the like.

When used in mammalian cells, an expression vector's control functions can be provided by viral regulatory elements. For example, commonly used promoters are derived from polyoma virus, adenovirus 2, cytomegalovirus, and simian virus 40. Additional suitable expression systems are described, e.g., in chapters 16 and 17 of Sambrook et al., eds., *Molecular Cloning: A Laboratory Manual,* 2nd, ed., Cold Spring Harbor Laboratory, Cold Spring Harbor Laboratory Press, Cold Spring Harbor, N.Y. (1989).

Recombinant expression vectors can include one or more control sequences that can be, for example, operably linked to the nucleic acid sequence encoding the gene to be expressed. Such control sequences are described, for example, in Goeddel, Gene Expression Technology: Methods in Enzymology 185, Academic Press, San Diego, Calif. (1990). In certain embodiments, the vector includes a control sequence that directs constitutive expression of the nucleotide sequence in the placental stem cells. In certain other embodiments, said vector comprises a control sequence that is inducible, e.g., by contact with a chemical agent, e.g., tetracycline.

The modulatory oligomeric or polymeric molecules can be administered to the cells by any technique known to those of skill in the art, e.g., by direct transfection. For example, said direct transfection can involve the step of pre-plating the cells prior to transfection, allowing them to reattach and resume growth for a period of time (e.g., 24 hours) before exposure to transfection complexes. The modulatory oligomeric or polymeric molecules can also be administered to the cells by reverse transfection. For example, said reverse transfection can involve the step of adding transfection complexes to the cells while they are in suspension, prior to plating.

In various embodiments, the effects of the modulatory oligomeric or polymeric molecules on placental stem cells, e.g., downregulation of one or more survival-associated genes in said placental stem cells so as to generate enhanced placental stem cells from said placental stem cells, can last for up to, about, or no more than, 1, 2, 3, 4, 5, 6, 7, 8, 9, 10, 11, 12, 13, 14, 15, 16, 17, 18, 19, 20, 21, 22 or 23 hours, or 1, 2, 3, 4, 5, 6, 7, 8, 9, 10, 11, 12, 13, 14, 15, 16, 17, 18, 19, 20, 21, 22, 23, 24, 25, 26, 27, or 28 days, or more. In certain embodiments, the enhanced placental stem cells generated using the methods described herein are used (e.g., administered to a subject) within no more than 1, 2, 3, 4, 5, 6, 7, 8, 9, 10, 11, 12, 13, 14, 15, 16, 17, 18, 19, 20, 21, 22 or 23 hours, or 1, 2, 3, 4, 5, 6, 7, 8, 9, 10, 11, 12, 13, 14, 15, 16, 17, 18, 19, 20, 21, 22, 23, 24, 25, 26, 27, or 28 days of the time the enhanced placental stem cells are produced. In certain embodiments, the enhanced placental stem cells generated using the methods described herein are preserved, e.g., cryopreserved, before use (e.g., before administration to a subject). In certain embodiments, the enhanced placental stem cells generated using the methods described herein are preserved, e.g., cryopreserved, then modified in accordance with the methods provided herein, then administered to a subject. In certain embodiments, the effects of the modulatory oligomeric or polymeric molecules on the enhanced placental stem cells are inducible. In certain other embodiments, no, or substantially no, cellular expansion (culturing of the enhanced placental stem cells, proliferation, etc.) is performed between the time the placental stem cells are modified to produce the enhanced placental stem cells and the time the enhanced placental stem cells are administered or cryopreserved.

Assessment of the function (e.g., silencing of survival-associated genes) of the modulatory oligomeric or polymeric molecules used in the methods described herein, e.g., the level or degree of gene silencing, can be accomplished by any art-recognized method for detection of protein production or nucleic acid production by cells. For example, assessment can be performed by determining the mRNA or protein level of a gene of interest in a sample of enhanced placental stem cells (e.g., a sample of $10 \times 10^5$ to $10 \times 10^7$ enhanced placental stem cells, or 1%, 2%, 3%, 4%, 5%, 6%, 7%, 8%, 9%, or 10% of said enhanced placental stem cells) as compared to equivalent placental stem cells that have not been transfected with such a nucleic acid sequence. Such assessment can be performed using, e.g. nucleic acid-based methods, e.g., northern blot analysis, reverse transcriptase polymerase chain reaction (RT-PCR), real-time PCR, quantitative PCR, and the like. In other embodiments, expression of protein can be assessed using antibodies that bind to the protein of interest, e.g., in an ELISA, sandwich assay, or the like. In a specific embodiment, the enhanced placental stem cells generated using the methods described herein produce 5%, 10%, 15%, 20%, 25%, 30%, 35%, 40%, 45%, 50%, 55%, 60%, 65%, 70%, 75%, 80%, 85%, 90%, 95%, or 100% less of the mRNA of a target gene (e.g., a survival-associated gene) as compared to corresponding unmodified placental stem cells (e.g., an equivalent amount of corresponding unmodified placental stem cells). In a specific embodiment, the enhanced placental stem cells generated using the methods described herein produce 5%, 10%, 15%, 20%, 25%, 30%, 35%, 40%, 45%, 50%, 55%, 60%, 65%, 70%, 75%, 80%, 85%, 90%, 95%, or 100% less of the protein of a target gene (e.g., a survival-associated gene) as compared to corresponding unmodified placental stem cells (e.g., an equivalent amount of corresponding unmodified placental stem cells).

5.2 Uses of Enhanced Placental Stem Cells

One advantage of the enhanced placental stem cells described herein is that they maintain functional characteristics of unmodified placental stem cells (e.g., the placental stem cells described in U.S. Pat. Nos. 7,311,904; 7,311,905; 7,468,276 and 8,057,788, the disclosures of which are hereby incorporated by reference in their entireties), yet demonstrate increased survival compared to, e.g., unmodified placental stem cells, when exposed to (or cultured in) conditions that cause cell death. Accordingly, the enhanced placental stem cells described herein can be advantageously used in methods that comprise the administration of placental stem cells to a subject, wherein the placental stem cells are exposed to environmental insults upon administration to the subject (e.g., the placental stem cells are exposed to other cells, antibodies, blood components (e.g., complement, serum), and other host cell components following administration).

In one embodiment, the enhanced placental stem cells described herein can be used in methods of treating an individual having or at risk of developing a disease, disorder or condition caused by, or relating to, an unwanted or harmful immune response, for instance, a disease, disorder or condition having an inflammatory component. In another embodiment, provided herein are methods for the modulation, e.g., suppression, of the activity, e.g., proliferation, of an immune cell, or plurality of immune cells, by contacting the immune cell(s) with a plurality of enhanced placental stem cells (e.g., a composition comprising enhanced placental stem cells). In accordance with such methods, a therapeutically effective amount of enhanced placental stem cells can be administered to the individual, wherein the administered enhanced placental stem cells can survive in said individual for greater periods of time than, e.g., unmodified placental stem cells administered in the same fashion.

In a specific embodiment, provided herein is a method of suppressing an immune response comprising contacting a plurality of immune cells with a plurality of enhanced placental stem cells for a time sufficient for said enhanced placental stem cells to detectably suppress an immune response, wherein said enhanced placental stem cells detectably suppress T cell proliferation in a mixed lymphocyte reaction (MLR) assay or a regression assay. An "immune cell" in the context of this method means any cell of the immune system, particularly T cells and NK (natural killer) cells. Thus, in various embodiments of the method, enhanced placental stem cells are contacted with a plurality of immune cells, wherein the plurality of immune cells are, or comprises, a plurality of T cells (e.g., a plurality of $CD3^+$ T cells, $CD4^+$ T cells and/or $CD8^+$ T cells) and/or natural killer cells. An "immune response" in the context of the method can be any response by an immune cell to a stimulus normally perceived by an immune cell, e.g., a response to the presence of an antigen. In various embodiments, an immune response can be the proliferation of T cells (e.g., $CD3^+$ T cells, $CD4^+$ T cells and/or $CD8^+$ T cells) in response to a foreign antigen, such as an antigen present in a transfusion or graft, or to a self-antigen, as in an autoimmune disease. The immune response can also be a proliferation of T cells contained within a graft. The immune response can also be any activity of a natural killer (NK) cell, the maturation of a dendritic cell, or the like. The immune response can also be a local, tissue- or organ-specific, or systemic effect of an activity of one or more classes of immune cells, e.g., the immune response can be graft versus host disease, inflammation, formation of inflammation-related scar tissue, an autoimmune condition (e.g., rheumatoid arthritis, Type I diabetes, lupus erythematosus, etc.). and the like.

"Contacting," as used herein in such a context, encompasses bringing the placental stem cells and immune cells together in a single container (e.g., culture dish, flask, vial, etc.) or in vivo, for example, in the same individual (e.g., mammal, for example, human). In one embodiment, the contacting is for a time sufficient, and with a sufficient number of enhanced placental stem cells and immune cells, that a change in an immune function of the immune cells is detectable. In certain embodiments, said contacting is sufficient to suppress immune function (e.g., T cell proliferation in response to an antigen) by at least 50%, 60%, 70%, 80%, 90% or 95%, compared to the immune function in the absence of the enhanced placental stem cells. Such suppression in an in vivo context can be determined in an in vitro assay (see below); that is, the degree of suppression in the in vitro assay can be extrapolated, for a particular number of enhanced placental stem cells and a number of immune cells in a recipient individual, to a degree of suppression in the individual.

The ability of enhanced placental stem cells to suppress an immune response can be, e.g., assessed in vitro. In certain embodiments, an enhanced placental stem cell provided herein suppresses an immune response at least 50%, 60%, 70%, 75%, 80%, 85%, 90%, 95%, or 99% as well as a corresponding unmodified placental stem cell. In certain embodiments, an enhanced placental stem cell provided herein suppresses an immune response to the same extent as a corresponding unmodified placental stem cell. For example, a plurality of enhanced placental stem cells can be tested in an MLR comprising combining $CD4^+$ or $CD8^+$ T cells, dendritic cells (DC) and enhanced placental stem cells in a ratio of about 10:1:2, wherein the T cells are stained with a dye such as, e.g., CFSE that partitions into daughter cells, and wherein the T cells are allowed to proliferate for about 6 days. The plurality of enhanced placental stem cells is immunosuppressive if the T cell proliferation at 6 days in the presence of enhanced placental stem cells is detectably reduced compared to T cell proliferation in the presence of DC and absence of placental stem cells. Additionally, a control using unmodified placental stem cells can be run in parallel to demonstrate that the enhanced placental stem cells are more immunosuppressive than unmodified or untreated placental stem cells. In such an MLR, for example, enhanced placental stem cells can be either thawed or harvested from culture. About 20,000 enhanced placental stem cells are resuspended in 100 µl of medium (RPMI 1640, 1 mM HEPES buffer, antibiotics, and 5% pooled human serum), and allowed to attach to the bottom of a well for 2 hours. $CD4^+$ and/or $CD8^+$ T cells are isolated from whole peripheral blood mononuclear cells Miltenyi magnetic beads. The cells are CFSE stained, and a total of 100,000 T cells ($CD4^+$ T cells alone, $CD8^+$ T cells alone, or equal amounts of $CD4^+$ and $CD8^+$ T cells) are added per well. The volume in the well is brought to 200 µl, and the MLR is allowed to proceed. A regression assay or BTR assay can be used in similar fashion.

In another aspect, provided herein is a method for promoting angiogenesis. In a specific embodiment, provided herein is a method for promoting angiogenesis in a subject, e.g., a human subject, comprising administering to said subject the enhanced placental stem cells described herein, or a composition thereof. In certain embodiments, an enhanced placental stem cell provided herein promotes angiogenesis at least 50%, 60%, 70%, 75%, 80%, 85%, 90%, 95%, or 99% as well as a corresponding unmodified placental stem cell. In certain embodiments, an enhanced placental stem cell provided herein promotes angiogenesis to the same extent as a corresponding unmodified placental stem cell. Assays for measuring the ability of cells (e.g., placental stem cells, including enhanced placental stem cells) to promote angiogenesis are known in the art (see, e.g., U.S. Patent Application Publication No. 2011/0250182, the disclosure of which is herein incorporated by reference in its entirety), e.g., assaying the ability of cells to promote tube formation by endothelial cells, assaying the ability of cells to promote endothelial cell migration and/or proliferation, and assaying the ability of cells to secrete factors that promote angiogenesis.

The enhanced placental stem cells described herein can be administered with one or more second types of stem cells, e.g., mesenchymal stem cells from bone marrow. Such second stem cells can be administered to an individual with said enhanced placental stem cells in a ratio of, e.g., about 1:10 to about 10:1.

The enhanced placental stem cells described herein can be administered to an individual in any manner known in the art, e.g., systemically, locally, intravenously, intramuscularly, intraperitoneally, intraocularly, parenterally, intrathecally, or directly into an organ, e.g., pancreas. For in vivo administration, the enhanced placental stem cells can be formulated as a pharmaceutical composition, as described below.

5.3 Enhanced Placental Stem Cells and Enhanced Placental Stem Cell Populations

The enhanced placental stem cells provided herein are produced from placental stem cells using the methods described herein. In accordance with the methods described herein for producing enhanced placental stem cells, the enhanced placental stem cells described herein express one or more survival-associated genes (as identified herein, e.g., one or more survival-associated genes identified in Table 1, above) at a decreased or increased level as compared to the expression of the same survival-associated gene in a corresponding unmodified placental stem cell (i.e., the expression of the one or more survival-associated genes is downregulated).

Placental stem cells can be either fetal or maternal in origin (that is, can have the genotype of either the mother or fetus). Populations of placental stem cells, or populations of cells comprising placental stem cells, can comprise placental stem cells that are solely fetal or maternal in origin, or can comprise a mixed population of placental stem cells of both fetal and maternal origin. The placental stem cells, and populations of cells comprising the placental stem cells, can be identified and selected by, e.g., the morphological, marker, and culture characteristics discussed below.

5.3.1 Physical and Morphological Characteristics

The placental stem cells used in the methods described herein for generating enhanced placental stem cells, when cultured in primary cultures or in cell culture, adhere to the tissue culture substrate, e.g., tissue culture container surface (e.g., tissue culture plastic). Placental stem cells in culture assume a generally fibroblastoid, stellate appearance, with a number of cytoplasmic processes extending from the central cell body. The placental stem cells used in the methods for generating enhanced placental stem cells described herein are, however, morphologically differentiable from fibroblasts cultured under the same conditions, as the placental stem cells exhibit a greater number of such processes than do fibroblasts. Morphologically, placental stem cells are also differentiable from hematopoietic stem cells, which generally assume a more rounded, or cobblestone, morphology in culture.

The enhanced placental stem cells described herein are thus distinct from, e.g., fibroblasts and hematopoietic stem cells. Further, the enhanced placental stem cells described herein are distinct from the placental stem cells used to generate the enhanced placental stem cells, particularly with respect to the ability of the cells to survive when exposed to and/or cultured under conditions that cause cell death of placental stem cells (i.e., unmodified placental stem cells).

5.3.2 Cell Surface, Molecular and Genetic Markers

As with unmodified placental stem cells, the enhanced placental stem cells described herein express a plurality of markers that can be used to identify and/or isolate the enhanced placental stem cells, or populations of cells that comprise the enhanced placental stem cells. Generally, the identifying markers associated with the enhanced placental stem cells described herein are the same as those that can be used to identify the placental stem cells from which the enhanced placental stem cells are derived (i.e., the placental stem cells used in the methods described herein for generating enhanced placental stem cells). Thus, the enhanced placental stem cells described herein are comparable to unmodified to placental stem cells in terms of cell surface, molecular, and genetic markers, with the difference between the cells being that the enhanced placental stem cells described herein express at least one of survival-associated gene (e.g., at least one of the genes identified in Table 1, above) at a lower level relative to the expression of said gene in an equivalent amount of corresponding unmodified placental stem cells, i.e., at least one survival-associated gene is downregulated/inhibited in the enhanced placental stem cells described herein, wherein said survival-associated gene is not downregulated/inhibited in unmodified placental stem cells.

The enhanced placental stem cells described herein, like the placental stem cells from which the enhanced placental stem cells are derived, are not bone marrow-derived mesenchymal cells, adipose-derived mesenchymal stem cells, or mesenchymal cells obtained from umbilical cord blood, placental blood, or peripheral blood.

In certain embodiments, the enhanced placental stem cells described herein (and/or the placental stem cells used in the methods described herein for producing enhanced placental stem cells) are CD34$^-$, CD10$^+$ and CD105$^+$ as detected by flow cytometry. In a specific embodiment, the isolated CD34$^-$, CD10$^+$, CD105$^+$ enhanced placental stem cells described herein (and/or the placental stem cells used in the methods described herein for producing enhanced placental stem cells) have the potential to differentiate into cells of a neural phenotype, cells of an osteogenic phenotype, and/or cells of a chondrogenic phenotype. In another specific embodiment, the isolated CD34$^-$, CD10$^+$, CD105$^+$ enhanced placental stem cells described herein (and/or the placental stem cells used in the methods described herein for producing enhanced placental stem cells) are additionally CD200$^+$. In another specific embodiment, the isolated CD34$^-$, CD10$^+$, CD105$^+$ enhanced placental stem cells described herein (and/or the placental stem cells used in the methods described herein for producing enhanced placental stem cells) are additionally CD45$^-$ or CD90$^+$. In another specific embodiment, the isolated CD34$^-$, CD10$^+$, CD105$^+$ enhanced placental stem cells described herein (and/or the placental stem cells used in the methods described herein for producing enhanced placental stem cells) are additionally CD45$^-$ and CD90$^+$, as detected by flow cytometry. In another specific embodiment, the isolated CD34$^-$, CD10$^+$, CD105$^+$, CD200$^+$ enhanced placental stem cells described herein (and/or the placental stem cells used in the methods described herein for producing enhanced placental stem cells) are additionally CD90$^+$ or CD45$^-$, as detected by flow cytometry. In another specific embodiment, the isolated CD34$^-$, CD10$^+$, CD105$^+$, CD200$^+$ enhanced placental stem cells described herein (and/or the placental stem cells used in the methods described herein for producing enhanced placental stem cells) are additionally CD90$^+$ and CD45$^-$, as detected by flow cytometry, i.e., the cells are CD34$^-$, CD10$^+$, CD45$^-$, CD90$^+$, CD105$^+$ and CD200$^+$. In another specific embodiment, said CD34$^-$, CD10$^+$, CD45$^-$, CD90$^+$, CD105$^+$, CD200$^+$ enhanced placental stem cells described herein (and/or the placental stem cells used in the methods described herein for producing enhanced placental stem cells) are additionally CD80$^-$ and CD86$^-$.

In certain embodiments, the enhanced placental stem cells described herein (and/or the placental stem cells used in the methods described herein for producing enhanced placental stem cells) are CD34$^-$, CD10$^+$, CD105$^+$ and CD200$^+$, and one or more of CD38$^-$, CD45$^-$, CD80$^-$, CD86$^-$, CD133$^-$, HLA-DR,DP,DQ$^-$, SSEA3$^-$, SSEA4$^-$, CD29$^+$, CD44$^+$, CD73$^+$, CD90$^+$, CD105$^+$, HLA-A,B,C$^+$, PDL1$^+$, ABC-p$^+$, and/or OCT-4$^+$, as detected by flow cytometry. In other embodiments, any of the CD34$^-$, CD10$^+$, CD105$^+$ enhanced placental stem cells described herein (and/or the placental stem cells used in the methods described herein for producing enhanced placental stem cells) are additionally one or more of CD29$^+$, CD38$^-$, CD44$^+$, CD54$^+$, SH3$^+$ or SH4$^+$. In another specific embodiment, the enhanced placental stem cells described herein (and/or the placental stem cells used in the methods described herein for producing enhanced placental stem cells) are additionally CD44$^+$. In another specific embodiment of any of the isolated CD34$^-$, CD10$^+$, CD105$^+$ enhanced placental stem cells described herein (and/or the placental stem cells used in the methods described herein for producing enhanced placental stem cells) are additionally one or more of CD117$^-$, CD133$^-$, KDR$^-$ (VEGFR2$^-$), HLA-A,B,C$^+$, HLA-DP,DQ,DR$^-$, or Programmed Death-1 Ligand (PDL1)$^+$, or any combination thereof.

In another embodiment, the CD34$^-$, CD10$^+$, CD105$^+$ enhanced placental stem cells described herein (and/or the placental stem cells used in the methods described herein for producing enhanced placental stem cells) are additionally one or more of CD13$^+$, CD29$^+$, CD33$^+$, CD38$^-$, CD44$^+$, CD45$^-$, CD54$^+$, CD62E$^-$, CD62L$^-$, CD62P$^-$, SH3$^+$ (CD73$^+$), SH4$^+$ (CD73$^+$), CD80$^-$, CD86$^-$, CD90$^+$, SH2$^+$ (CD105$^+$), CD106/VCAM$^+$, CD117$^-$, CD144/VE-cadherin$^{low}$, CD184/CXCR4$^-$, CD200$^+$, CD133$^-$, OCT-4$^+$, SSEA3$^-$, SSEA4$^-$, ABC-p$^+$, KDR$^-$ (VEGFR2$^-$), HLA-A,B,C$^+$, HLA-DP,DQ,DR$^-$, HLA-G$^-$, or Programmed Death-1 Ligand (PDL1)$^+$, or any combination thereof. In another embodiment, the CD34$^-$, CD10$^+$, CD105$^+$ enhanced placental stem cells described herein (and/or the placental stem cells used in the methods described herein for producing enhanced placental stem cells) are additionally CD13$^+$, CD29$^+$, CD33$^+$, CD38$^-$, CD44$^+$, CD45$^-$, CD54/ICAM$^+$, CD62E$^-$, CD62L$^-$, CD62P$^-$, SH3$^+$ (CD73$^+$), SH4$^+$ (CD73$^+$), CD80$^-$, CD86$^-$, CD90$^+$, SH2$^+$ (CD105$^+$), CD106/VCAM$^+$, CD117$^-$, CD144/VE-cadherin$^{low}$, CD184/CXCR4$^-$, CD200$^+$, CD133$^-$, OCT-4$^+$, SSEA3$^-$, SSEA4$^-$, ABC-p$^+$, KDR$^-$ (VEGFR2$^-$), HLA-A,B,C$^+$, HLA-DP,DQ, DR$^-$, HLA-G$^-$, and Programmed Death-1 Ligand (PDL1)$^+$.

In another specific embodiment, any of the enhanced placental stem cells described herein (and/or the placental stem cells used in the methods described herein for producing enhanced placental stem cells) are additionally ABC-p$^+$, as detected by flow cytometry, or OCT-4$^+$ (POU5F1$^+$), as determined by reverse-transcriptase polymerase chain reaction (RT-PCR), wherein ABC-p is a placenta-specific ABC transporter protein (also known as breast cancer resistance protein (BCRP) or as mitoxantrone resistance protein (MXR)), and OCT-4 is the Octamer-4 protein (POU5F1). In another specific embodiment, any of the enhanced placental stem cells described herein (and/or the placental stem cells used in the methods described herein for producing enhanced placental stem cells) are additionally SSEA3⁻ or SSEA4⁻, as determined by flow cytometry, wherein SSEA3 is Stage Specific Embryonic Antigen 3, and SSEA4 is Stage Specific Embryonic Antigen 4. In another specific embodiment, any of the enhanced placental stem cells described herein (and/or the placental stem cells used in the methods described herein for producing enhanced placental stem cells) are additionally SSEA3⁻ and SSEA4⁻.

In another specific embodiment, any of the enhanced placental stem cells described herein (and/or the placental stem cells used in the methods described herein for producing enhanced placental stem cells) are, or are additionally, one or more of MHC-I⁺ (e.g., HLA-A,B,C⁺), MHC-II⁻ (e.g., HLA-DP,DQ,DR⁻) or HLA-G⁻. In another specific embodiment, any of the enhanced placental stem cells described herein (and/or the placental stem cells used in the methods described herein for producing enhanced placental stem cells) are additionally MHC-I⁺ (e.g., HLA-A,B,C⁺), MHC-II⁻ (e.g., HLA-DP,DQ,DR⁻) and HLA-G⁻.

Also provided herein are populations of the enhanced placental stem cells described herein. In certain embodiments, described herein are populations of enhanced placental stem cells comprising the isolated enhanced placental stem cells described herein, wherein the populations of cells comprise, e.g., at least 10%, 15%, 20%, 25%, 30%, 35%, 40%, 45%, 50%, 55%, 60%, 65%, 70%, 75%, 80%, 85%, 90%, 95% or 98% isolated CD10⁺, CD105⁺ and CD34⁻ enhanced placental stem cells; that is, at least 10%, 15%, 20%, 25%, 30%, 35%, 40%, 45%, 50%, 55%, 60%, 65%, 70%, 75%, 80%, 85%, 90%, 95% or 98% of cells in said population are isolated CD10⁺, CD105⁺ and CD34⁻ enhanced placental stem cells. In a specific embodiment, the isolated CD34⁻, CD10⁺, CD105⁺ enhanced placental stem cells are additionally CD200⁺. In another specific embodiment, the isolated CD34⁻, CD10⁺, CD105⁺, CD200⁺ enhanced placental stem cells are additionally CD90⁺ or CD45⁻, as detected by flow cytometry. In another specific embodiment, the isolated CD34⁻, CD10⁺, CD105⁺, CD200⁺ enhanced placental stem cells are additionally CD90⁺ and CD45⁻, as detected by flow cytometry. In another specific embodiment, any of the isolated CD34⁻, CD10⁺, CD105⁺ enhanced placental stem cells described above are additionally one or more of CD29⁺, CD38⁻, CD44⁺, CD54⁺, SH3⁺ or SH4⁺. In another specific embodiment, the isolated CD34⁻, CD10⁺, CD105⁺ enhanced placental stem cells, or isolated CD34⁻, CD10⁺, CD105⁺, CD200⁺ placental stem cells, are additionally CD44⁺. In a specific embodiment of any of the populations of cells comprising isolated CD34⁻, CD10⁺, CD105⁺ enhanced placental stem cells above, the isolated enhanced placental stem cells are additionally one or more of CD13⁺, CD29⁺, CD33⁺, CD38⁻, CD44⁺, CD45⁻, CD54⁺, CD62E⁻, CD62L⁻, CD62P⁻, SH3⁺ (CD73⁺), SH4⁺ (CD73⁺), CD80⁻, CD86⁻, CD90⁺, SH2⁺ (CD1051, CD106/VCAM⁺, CD117⁻, CD144/VE-cadherin$^{low}$, CD184/CXCR4⁻, CD200⁺, CD133⁻, OCT-4⁺, SSEA3⁻, SSEA4⁻, ABC-p⁺, KDR⁻ (VEGFR2⁻), HLA-A,B,C⁺, HLA-DP,DQ,DR⁻, HLA-G⁻, or Programmed Death-1 Ligand (PDL1)⁺, or any combination thereof. In another specific embodiment, the CD34⁻, CD10⁺, CD105⁺ enhanced placental stem cells are additionally CD13⁺, CD29⁺, CD33⁺, CD38⁻, CD44⁺, CD45⁻, CD54/ICAM⁺, CD62E⁻, CD62L⁻, CD62P⁻, SH3⁺ (CD73⁺), SH4⁺ (CD73⁺), CD80⁻, CD86⁻, CD90⁺, SH2⁺ (CD105⁺), CD106/VCAM⁺, CD117⁻, CD144/VE-cadherin$^{low}$, CD184/CXCR4⁻, CD200⁺, CD133⁻, OCT-4⁺, SSEA3⁻, SSEA4⁻, ABC-p⁺, KDR⁻ (VEGFR2⁻), HLA-A,B,C⁺, HLA-DP,DQ,DR⁻, HLA-G⁻, and Programmed Death-1 Ligand (PDL1)⁺.

In certain embodiments, the isolated enhanced placental stem cells in said population of cells are one or more, or all, of CD10⁺, CD29⁺, CD34⁻, CD38⁻, CD44⁺, CD45⁻, CD54⁺, CD90⁺, SH2⁺, SH3⁺, SH4⁺, SSEA3⁻, SSEA4⁻, OCT-4⁺, and ABC-p⁺, wherein said the placental stem cells used in the method of generating said isolated enhanced placental stem cells were obtained by physical and/or enzymatic disruption of placental tissue. In a specific embodiment, the isolated enhanced placental stem cells are OCT-4⁺ and ABC-p⁺. In another specific embodiment, the isolated enhanced placental stem cells are OCT-4⁺ and CD34⁻, wherein said isolated enhanced placental stem cells have at least one of the following characteristics: CD10⁺, CD29⁺, CD44⁺, CD45⁻, CD54⁺, CD90⁺, SH3⁺, SH4⁺, SSEA3⁻, and SSEA4⁻. In another specific embodiment, the isolated enhanced placental stem cells are OCT-4⁺, CD34⁻, CD10⁺, CD29⁺, CD44⁺, CD45⁻, CD54⁺, CD90⁺, SH3⁺, SH4⁺, SSEA3⁻, and SSEA4⁻. In another embodiment, the isolated enhanced placental stem cells are OCT-4⁺, CD34⁻, SSEA3⁻, and SSEA4⁻. In another specific embodiment, the isolated enhanced placental stem cells are OCT-4⁺ and CD34⁻, and is either SH2⁺ or SH3⁺. In another specific embodiment, the isolated enhanced placental stem cells are OCT-4⁺, CD34⁻, SH2⁺, and SH3⁺. In another specific embodiment, the isolated enhanced placental stem cells are OCT-4⁺, CD34⁻, SSEA3⁻, and SSEA4⁻, and are either SH2⁺ or SH3⁺. In another specific embodiment, the isolated enhanced placental stem cells are OCT-4⁺ and CD34⁻, and either SH2⁺ or SH3⁺, and at least one of CD10⁺, CD29⁺, CD44⁺, CD45⁻, CD54⁺, CD90⁺, SSEA3⁻, or SSEA4⁻. In another specific embodiment, the isolated enhanced placental stem cells are OCT-4⁺, CD34⁻, CD10⁺, CD29⁺, CD44⁺, CD45⁻, CD54⁺, CD90⁺, SSEA3⁻, and SSEA4⁻, and either SH2⁺ or SH3⁺.

In another embodiment, the isolated enhanced placental stem cells are SH2⁺, SH3⁺, SH4⁺ and OCT-4⁺. In another specific embodiment, the isolated enhanced placental stem cells are CD10⁺, CD29⁺, CD44⁺, CD54⁺, CD90⁺, CD34⁻, CD45⁻, SSEA3⁻, or SSEA4⁻. In another embodiment, the isolated enhanced placental stem cells are SH2⁺, SH3⁺, SH4⁺, SSEA3⁻ and SSEA4⁻. In another specific embodiment, the isolated enhanced placental stem cells are SH2⁺, SH3⁺, SH4⁺, SSEA3⁻ and SSEA4⁻, CD10⁺, CD29⁺, CD44⁺, CD54⁺, CD90⁺, OCT-4⁺, CD34⁻ or CD45⁻.

In another embodiment, the isolated enhanced placental stem cells described herein are CD10⁺, CD29⁺, CD34⁻, CD44⁺, CD45⁻, CD54⁺, CD90⁺, SH2⁺, SH3⁺, and SH4⁺; wherein said isolated enhanced placental stem cells are additionally one or more of OCT-4⁺, SSEA3⁻ or SSEA4⁻.

In certain embodiments, isolated enhanced placental stem cells are CD200⁺ or HLA-G⁻. In a specific embodiment, the isolated enhanced placental stem cells are CD200⁺ and HLA-G⁻. In another specific embodiment, the isolated enhanced placental stem cells are additionally CD73⁺ and CD105⁺. In another specific embodiment, the isolated enhanced placental stem cells are additionally CD34⁻, CD38⁻ or CD45⁻. In another specific embodiment, the isolated enhanced placental stem cells are additionally CD34⁻, CD38⁻ and CD45⁻. In another specific embodiment, said enhanced placental stem cells are CD34⁻, CD38⁻, CD45⁻, CD73⁺ and CD105⁺. In another specific embodiment, said isolated CD200⁺ or HLA-G⁻ enhanced placental stem cells facilitate the formation of embryoid-like bodies in a population of placental cells comprising the isolated placental stem cells, under conditions that allow the formation of embryoid-like bodies. In another specific embodiment, the isolated enhanced placental stem cells are isolated away from placental cells that are not said enhanced placental stem cells. In another specific embodiment, said isolated enhanced placental stem cells are isolated away from placental cells that do not display this combination of markers.

In another embodiment, a cell population useful in the methods and compositions described herein is a population of cells comprising, e.g., that is enriched for, CD200$^+$, HLA-G$^-$ enhanced placental stem cells. In a specific embodiment, said population is a population of placental cells. In various embodiments, at least about 10%, at least about 20%, at least about 30%, at least about 40%, at least about 50%, or at least about 60% of cells in said cell population are isolated CD200$^+$, HLA-G$^-$ enhanced placental stem cells. Preferably, at least about 70% of cells in said cell population are isolated CD200$^+$, HLA-G$^-$ enhanced placental stem cells. More preferably, at least about 90%, 95%, or 99% of said cells are isolated CD200$^+$, HLA-G$^-$ enhanced placental stem cells. In a specific embodiment of the cell populations, said isolated CD200$^+$, HLA-G$^-$ enhanced placental stem cells are also CD73$^+$ and CD105$^+$. In another specific embodiment, said isolated CD200$^+$, HLA-G$^-$ enhanced placental stem cells are also CD34$^-$, CD38$^-$ or CD45$^-$. In another specific embodiment, said isolated CD200$^+$, HLA-G$^-$ enhanced placental stem cells are also CD34$^-$, CD38$^-$, CD45$^-$, CD73$^+$ and CD105$^+$. In another embodiment, said cell population produces one or more embryoid-like bodies when cultured under conditions that allow the formation of embryoid-like bodies. In another specific embodiment, said cell population is isolated away from placental cells that are not enhanced placental stem cells. In another specific embodiment, said isolated CD200$^+$, HLA-G$^-$ enhanced placental stem cells are isolated away from placental cells that do not display these markers.

In another embodiment, the isolated enhanced placental stem cells described herein are CD73$^+$, CD105$^+$, and CD200$^+$. In another specific embodiment, the isolated enhanced placental stem cells are HLA-G$^-$. In another specific embodiment, the isolated enhanced placental stem cells are CD34$^-$, CD38$^-$ or CD45$^-$. In another specific embodiment, the isolated enhanced placental stem cells are CD34$^-$, CD38$^-$ and CD45$^-$. In another specific embodiment, the isolated enhanced placental stem cells are CD34$^-$, CD38$^-$, CD45$^-$, and HLA-G$^-$. In another specific embodiment, the isolated CD73$^+$, CD105$^+$, and CD200$^+$ enhanced placental stem cells facilitate the formation of one or more embryoid-like bodies in a population of placental cells comprising the isolated enhanced placental stem cells, when the population is cultured under conditions that allow the formation of embryoid-like bodies. In another specific embodiment, the isolated enhanced placental stem cells are isolated away from placental cells that are not the isolated enhanced placental stem cells. In another specific embodiment, the isolated enhanced placental stem cells are isolated away from placental cells that do not display these markers.

In another embodiment, a cell population useful in the methods and compositions described herein is a population of cells comprising, e.g., that is enriched for, isolated CD73$^+$, CD105$^+$, CD200$^+$ enhanced placental stem cells. In various embodiments, at least about 10%, at least about 20%, at least about 30%, at least about 40%, at least about 50%, or at least about 60% of cells in said cell population are isolated CD73$^+$, CD105$^+$, CD200$^+$ enhanced placental stem cells. In another embodiment, at least about 70% of said cells in said population of cells are isolated CD73$^+$, CD105$^+$, CD200$^+$ enhanced placental stem cells. In another embodiment, at least about 90%, 95% or 99% of cells in said population of cells are isolated CD73$^+$, CD105$^+$, CD200$^+$ enhanced placental stem cells. In a specific embodiment of said populations, the isolated enhanced placental stem cells are HLA-G$^-$. In another specific embodiment, the isolated enhanced placental stem cells are additionally CD34$^-$, CD38$^-$ or CD45$^-$. In another specific embodiment, the isolated enhanced placental stem cells are additionally CD34$^-$, CD38$^-$ and CD45$^-$. In another specific embodiment, the isolated enhanced placental stem cells are additionally CD34$^-$, CD38$^-$, CD45$^-$, and HLA-G$^-$. In another specific embodiment, said population of cells produces one or more embryoid-like bodies when cultured under conditions that allow the formation of embryoid-like bodies. In another specific embodiment, said population of enhanced placental stem cells is isolated away from placental cells that are not enhanced placental stem cells. In another specific embodiment, said population of enhanced placental stem cells is isolated away from placental cells that do not display these characteristics.

In certain other embodiments, the isolated enhanced placental stem cells are one or more of CD10$^+$, CD29$^+$, CD34$^-$, CD38$^-$, CD44$^+$, CD45$^-$, CD54$^+$, CD90$^+$, SH2$^+$, SH3$^+$, SH4$^+$, SSEA3-, SSEA4$^-$, OCT-4$^+$, HLA-G$^-$ or ABC-p$^+$. In a specific embodiment, the isolated enhanced placental stem cells are CD10$^+$, CD29$^+$, CD34$^-$, CD38$^-$, CD44$^+$, CD45$^-$, CD54$^+$, CD90$^+$, SH2$^+$, SH3$^+$, SH4$^+$, SSEA3-, SSEA4$^-$, and OCT-4$^+$. In another specific embodiment, the isolated enhanced placental stem cells are CD10$^+$, CD29$^+$, CD34$^-$, CD38$^-$, CD45$^-$, CD54$^+$, SH2$^+$, SH3$^+$, and SH4$^+$. In another specific embodiment, the isolated enhanced placental stem cells CD10$^+$, CD29$^+$, CD34$^-$, CD38$^-$, CD45$^-$, CD54$^+$, SH2$^+$, SH3$^+$, SH4$^+$ and OCT-4$^+$. In another specific embodiment, the isolated enhanced placental stem cells are CD10$^+$, CD29$^+$, CD34$^-$, CD38$^-$, CD44$^+$, CD45$^-$, CD54$^+$, CD90$^+$, HLA-G$^-$, SH2$^+$, SH3$^+$, SH4$^+$. In another specific embodiment, the isolated enhanced placental stem cells are OCT-4$^+$ and ABC-p$^+$. In another specific embodiment, the isolated enhanced placental stem cells are SH2$^+$, SH3$^+$, SH4$^+$ and OCT-4$^+$. In another embodiment, the isolated enhanced placental stem cells are OCT-4$^+$, CD34$^-$, SSEA3$^-$, and SSEA4$^-$. In a specific embodiment, said isolated OCT-4$^+$, CD34$^-$, SSEA3$^-$, and SSEA4$^-$ enhanced placental stem cells are additionally CD10$^+$, CD29$^+$, CD34$^-$, CD44$^+$, CD45$^-$, CD54$^+$, CD90$^+$, SH2$^+$, SH3$^+$, and SH4$^+$. In another embodiment, the isolated enhanced placental stem cells are OCT-4$^+$ and CD34$^-$, and either SH3$^+$ or SH4$^+$. In another embodiment, the isolated enhanced placental stem cells are CD34$^-$ and either CD10$^+$, CD29$^+$, CD44$^+$, CD54$^+$, CD90$^+$, or OCT-4$^+$.

In another embodiment, isolated enhanced placental stem cells are CD200$^+$ and OCT-4$^+$. In a specific embodiment, the isolated enhanced placental stem cells are CD73$^+$ and CD105$^+$. In another specific embodiment, said isolated enhanced placental stem cells are HLA-G$^-$. In another specific embodiment, said isolated CD200$^+$, OCT-4$^+$ enhanced placental stem cells are CD34$^-$, CD38$^-$ or CD45$^-$. In another specific embodiment, said isolated CD200$^+$, OCT-4$^+$ enhanced placental stem cells are CD34$^-$, CD38$^-$ and CD45$^-$. In another specific embodiment, said isolated CD200$^+$, OCT-4$^+$ enhanced placental stem cells are CD34$^-$, CD38$^-$, CD45$^-$, CD73$^+$, CD105$^+$ and HLA-G$^-$. In another specific embodiment, the isolated CD200$^+$, OCT-4$^+$ enhanced placental stem cells facilitate the production of one or more embryoid-like bodies by a population of placental cells that comprises the enhanced placental stem cells, when the population is cultured under conditions that allow the formation of embryoid-like bodies. In another specific embodiment, said isolated CD200$^+$, OCT-4$^+$ enhanced placental stem cells are isolated away from placental cells that are not said enhanced placental stem cells. In another specific embodiment, said isolated CD200$^+$, OCT-4$^+$ enhanced placental stem cells are isolated away from placental cells that do not display these characteristics.

In another embodiment, a cell population useful in the methods and compositions described herein is a population of cells comprising, e.g., that is enriched for, CD200$^+$, OCT-4+ enhanced placental stem cells. In various embodiments, at least about 10%, at least about 20%, at least about 30%, at least about 40%, at least about 50%, or at least about 60% of cells in said cell population are isolated CD200$^+$, OCT-4$^+$ enhanced placental stem cells. In another embodiment, at least about 70% of said cells are said isolated CD200$^+$, OCT-4$^+$ enhanced placental stem cells. In another embodiment, at least about 80%, 90%, 95%, or 99% of cells in said cell population are said isolated CD200$^+$, OCT-4$^+$ enhanced placental stem cells. In a specific embodiment of the isolated populations, said isolated CD200$^+$, OCT-4$^+$ enhanced placental stem cells are additionally CD73$^+$ and CD105$^+$. In another specific embodiment, said isolated CD200$^+$, OCT-4$^+$ enhanced placental stem cells are additionally HLA-G$^-$. In another specific embodiment, said isolated CD200$^+$, OCT-4$^+$ enhanced placental stem cells are additionally CD34$^-$, CD38$^-$ and CD45$^-$. In another specific embodiment, said isolated CD200$^+$, OCT-4$^+$ enhanced placental stem cells are additionally CD34$^-$, CD38$^-$, CD45$^-$, CD73$^+$, CD105$^+$ and HLA-G$^-$. In another specific embodiment, the cell population produces one or more embryoid-like bodies when cultured under conditions that allow the formation of embryoid-like bodies. In another specific embodiment, said cell population is isolated away from placental cells that are not isolated CD200$^+$, OCT-4$^+$ enhanced placental stem cells. In another specific embodiment, said cell population is isolated away from placental cells that do not display these markers.

In another embodiment, the isolated enhanced placental stem cells useful in the methods and compositions described herein are CD73$^+$, CD105$^+$ and HLA-G$^-$. In another specific embodiment, the isolated CD73$^+$, CD105$^+$ and HLA-G$^-$ enhanced placental stem cells are additionally CD34$^-$, CD38$^-$ or CD45$^-$. In another specific embodiment, the isolated CD73$^+$, CD105$^+$, HLA-G$^-$ enhanced placental stem cells are additionally CD34$^-$, CD38$^-$ and CD45$^-$. In another specific embodiment, the isolated CD73$^+$, CD105$^+$, HLA-G$^-$ enhanced placental stem cells are additionally OCT-4$^+$. In another specific embodiment, the isolated CD73$^+$, CD105$^+$, HLA-G$^-$ enhanced placental stem cells are additionally CD200$^+$. In another specific embodiment, the isolated CD73$^+$, CD105$^+$, HLA-G$^-$ enhanced placental stem cells are additionally CD34$^-$, CD38$^-$, CD45$^-$, OCT-4$^+$ and CD200$^+$. In another specific embodiment, the isolated CD73$^+$, CD105$^+$, HLA-G$^-$ enhanced placental stem cells facilitate the formation of embryoid-like bodies in a population of placental cells comprising said enhanced placental stem cells, when the population is cultured under conditions that allow the formation of embryoid-like bodies. In another specific embodiment, the isolated CD73$^+$, CD105$^+$, HLA-G$^-$ enhanced placental stem cells are isolated away from placental cells that are not the isolated CD73$^+$, CD105$^+$, HLA-G$^-$ enhanced placental stem cells. In another specific embodiment, said the isolated CD73$^+$, CD105$^+$, HLA-G$^-$ enhanced placental stem cells are isolated away from placental cells that do not display these markers.

In another embodiment, a cell population useful in the methods and compositions described herein is a population of cells comprising, e.g., that is enriched for, isolated CD73$^+$, CD105$^+$ and HLA-G$^-$ enhanced placental stem cells. In various embodiments, at least about 10%, at least about 20%, at least about 30%, at least about 40%, at least about 50%, or at least about 60% of cells in said population of cells are isolated CD73$^+$, CD105$^+$, HLA-G$^-$ enhanced placental stem cells. In another embodiment, at least about 70% of cells in said population of cells are isolated CD73$^+$, CD105$^+$, HLA-G$^-$ enhanced placental stem cells. In another embodiment, at least about 90%, 95% or 99% of cells in said population of cells are isolated CD73$^+$, CD105$^+$, HLA-G$^-$ enhanced placental stem cells. In a specific embodiment of the above populations, said isolated CD73$^+$, CD105$^+$, HLA-G$^-$ enhanced placental stem cells are additionally CD34$^-$, CD38$^-$ or CD45$^-$. In another specific embodiment, said isolated CD73$^+$, CD105$^+$, HLA-G$^-$ enhanced placental stem cells are additionally CD34$^-$, CD38$^-$ and CD45$^-$. In another specific embodiment, said isolated CD73$^+$, CD105$^+$, HLA-G$^-$ enhanced placental stem cells are additionally OCT-4$^+$. In another specific embodiment, said isolated CD73$^+$, CD105$^+$, HLA-G$^-$ enhanced placental stem cells are additionally CD200$^+$. In another specific embodiment, said isolated CD73$^+$, CD105$^+$, HLA-G$^-$ enhanced placental stem cells are additionally CD34$^-$, CD38$^-$, CD45$^-$, OCT-4$^+$ and CD200$^+$. In another specific embodiment, said cell population is isolated away from placental cells that are not CD73$^+$, CD105$^+$, HLA-G$^-$ enhanced placental stem cells. In another specific embodiment, said cell population is isolated away from placental cells that do not display these markers.

In another embodiment, the isolated enhanced placental stem cells are CD73$^+$ and CD105$^+$ and facilitate the formation of one or more embryoid-like bodies in a population of isolated placental cells comprising said CD73$^+$, CD105$^+$ cells when said population is cultured under conditions that allow formation of embryoid-like bodies. In another specific embodiment, said isolated CD73$^+$, CD105$^+$ enhanced placental stem cells are additionally CD34$^-$, CD38$^-$ or CD45$^-$. In another specific embodiment, said isolated CD73$^+$, CD105$^+$ enhanced placental stem cells are additionally CD34$^-$, CD38$^-$ and CD45$^-$. In another specific embodiment, said isolated CD73$^+$, CD105$^+$ enhanced placental stem cells are additionally OCT-4$^+$. In another specific embodiment, said isolated CD73$^+$, CD105$^+$ enhanced placental stem cells are additionally OCT-4$^+$, CD34$^-$, CD38$^-$ and CD45$^-$. In another specific embodiment, said isolated CD73$^+$, CD105+ enhanced placental stem cells are isolated away from placental cells that are not said cells. In another specific embodiment, said isolated CD73$^+$, CD105$^+$ enhanced placental stem cells are isolated away from placental cells that do not display these characteristics.

In another embodiment, a cell population useful in the methods and compositions described herein is a population of cells comprising, e.g., that is enriched for, isolated enhanced placental stem cells that are CD73$^+$, CD105$^+$ and facilitate the formation of one or more embryoid-like bodies in a population of isolated placental cells comprising said cells when said population is cultured under conditions that allow formation of embryoid-like bodies. In various embodiments, at least about 10%, at least about 20%, at least about 30%, at least about 40%, at least about 50%, or at least about 60% of cells in said population of cells are said isolated CD73$^+$, CD105$^+$ enhanced placental stem cells. In another embodiment, at least about 70% of cells in said population of cells are said isolated CD73$^+$, CD105$^+$ enhanced placental stem cells. In another embodiment, at least about 90%, 95% or 99% of cells in said population of cells are said isolated CD73$^+$, CD105$^+$ enhanced placental stem cells. In a specific embodiment of the above populations, said isolated CD73$^+$, CD105$^+$ enhanced placental stem cells are additionally CD34$^-$, CD38$^-$ or CD45$^-$. In another specific embodiment, said isolated CD73$^+$, CD105$^+$ enhanced placental stem cells are additionally CD34$^-$, CD38$^-$ and CD45$^-$. In another specific embodiment, said isolated CD73$^+$, CD105$^+$ enhanced placental stem cells are additionally OCT-4$^+$. In another specific embodiment, said isolated CD73$^+$, CD105$^+$ enhanced placental stem cells are additionally CD200$^+$. In another specific embodiment, said isolated CD73$^+$, CD105$^+$ enhanced placental stem cells are additionally CD34$^-$, CD38$^-$, CD45$^-$, OCT-4$^+$ and CD200$^+$. In another specific embodiment, said cell population is isolated away from placental cells that are not said isolated CD73$^+$, CD105$^+$ enhanced placental stem cells. In another specific embodiment, said cell population is isolated away from placental cells that do not display these markers.

In another embodiment, the isolated enhanced placental stem cells are OCT-4$^+$ and facilitate formation of one or more embryoid-like bodies in a population of isolated placental cells comprising said enhanced placental stem cells when said population of cells is cultured under conditions that allow formation of embryoid-like bodies. In a specific embodiment, said isolated OCT-4$^+$ enhanced placental stem cells are additionally CD73$^+$ and CD105$^+$. In another specific embodiment, said isolated OCT-4$^+$ enhanced placental stem cells are additionally CD34$^-$, CD38$^-$, or CD45$^-$. In another specific embodiment, said isolated OCT-4$^+$ enhanced placental stem cells are additionally CD200$^+$. In another specific embodiment, said isolated OCT-4$^+$ enhanced placental stem cells are additionally CD73$^+$, CD105$^+$, CD200$^+$, CD34$^-$, CD38$^-$, and CD45$^-$. In another specific embodiment, said isolated OCT-4$^+$ enhanced placental stem cells are isolated away from placental cells that are not OCT-4$^+$ enhanced placental stem cells. In another specific embodiment, said isolated OCT-4$^+$ enhanced placental stem cells are isolated away from placental cells that do not display these characteristics.

In another embodiment, a cell population useful in the methods and compositions described herein is a population of cells comprising, e.g., that is enriched for, isolated enhanced placental stem cells that are OCT-4$^+$ and facilitate the formation of one or more embryoid-like bodies in a population of isolated placental cells comprising said cells when said population is cultured under conditions that allow formation of embryoid-like bodies. In various embodiments, at least about 10%, at least about 20%, at least about 30%, at least about 40%, at least about 50%, or at least about 60% of cells in said population of cells are said isolated OCT-4$^+$ enhanced placental stem cells. In another embodiment, at least about 70% of cells in said population of cells are said isolated OCT-4$^+$ enhanced placental stem cells. In another embodiment, at least about 80%, 90%, 95% or 99% of cells in said population of cells are said isolated OCT-4$^+$ enhanced placental stem cells. In a specific embodiment of the above populations, said isolated OCT-4$^+$ enhanced placental stem cells are additionally CD34$^-$, CD38$^-$ or CD45$^-$. In another specific embodiment, said isolated OCT-4$^+$ enhanced placental stem cells are additionally CD34$^-$, CD38$^-$ and CD45$^-$. In another specific embodiment, said isolated OCT-4$^+$ enhanced placental stem cells are additionally CD73$^+$ and CD105$^+$. In another specific embodiment, said isolated OCT-4$^+$ enhanced placental stem cells are additionally CD200$^+$. In another specific embodiment, said isolated OCT-4$^+$ enhanced placental stem cells are additionally CD73$^+$, CD105$^+$, CD200$^+$, CD34$^-$, CD38$^-$, and CD45$^-$. In another specific embodiment, said cell population is isolated away from placental cells that are not said enhanced placental stem cells. In another specific embodiment, said cell population is isolated away from placental cells that do not display these markers.

In another embodiment, the isolated placental stem cells useful in the methods and compositions described herein are isolated HLA-A,B,C$^+$, CD45$^-$, CD133$^-$ and CD34$^-$ enhanced placental stem cells. In another embodiment, a cell population useful in the methods and compositions described herein is a population of cells comprising isolated enhanced placental stem cells, wherein at least about 70%, at least about 80%, at least about 90%, at least about 95% or at least about 99% of cells in said population of cells are isolated HLA-A,B,C$^+$, CD45$^-$, CD133$^-$ and CD34$^-$ enhanced placental stem cells. In a specific embodiment, said isolated enhanced placental stem cells or population of isolated enhanced placental stem cells is isolated away from placental cells that are not HLA-A,B,C$^+$, CD45$^-$, CD133$^-$ and CD34$^-$ enhanced placental stem cells. In another specific embodiment, said isolated enhanced placental stem cells are non-maternal in origin. In another specific embodiment, said population of isolated enhanced placental stem cells are substantially free of maternal components; e.g., at least about 40%, 45%, 5-0%, 55%, 60%, 65%, 70%, 75%, 90%, 85%, 90%, 95%, 98% or 99% of said cells in said population of isolated enhanced placental stem cells are non-maternal in origin.

In another embodiment, the isolated enhanced placental stem cells useful in the methods and compositions described herein are isolated CD10$^+$, CD13$^+$, CD33$^+$, CD45$^-$, CD117$^-$ and CD133$^-$ enhanced placental stem cells. In another embodiment, a cell population useful in the methods and compositions described herein is a population of cells comprising isolated enhanced placental stem cells, wherein at least about 70%, at least about 80%, at least about 90%, at least about 95% or at least about 99% of cells in said population of cells are isolated CD10$^+$, CD13$^+$, CD33$^+$, CD45$^-$, CD117$^-$ and CD133$^-$ enhanced placental stem cells. In a specific embodiment, said isolated enhanced placental stem cells or population of isolated enhanced placental stem cells is isolated away from placental cells that are not said isolated enhanced placental stem cells. In another specific embodiment, said isolated CD10$^+$, CD13$^+$, CD33$^+$, CD45$^-$, CD117$^-$ and CD133$^-$ enhanced placental stem cells are non-maternal in origin, i.e., have the fetal genotype. In another specific embodiment, at least about 40%, 45%, 50%, 55%, 60%, 65%, 70%, 75%, 90%, 85%, 90%, 95%, 98% or 99% of said cells in said population of isolated enhanced placental stem cells, are non-maternal in origin. In another specific embodiment, said isolated enhanced placental stem cells or population of isolated enhanced placental stem cells are isolated away from placental cells that do not display these characteristics.

In another embodiment, the isolated enhanced placental stem cells are isolated CD10$^+$ CD33$^-$, CD44$^+$, CD45$^-$, and CD117$^-$ enhanced placental stem cells. In another embodiment, a cell population useful for the in the methods and compositions described herein is a population of cells comprising, e.g., enriched for, isolated enhanced placental stem cells, wherein at least about 70%, at least about 80%, at least about 90%, at least about 95% or at least about 99% of cells in said population of cells are isolated CD10$^+$ CD33$^-$, CD44$^+$, CD45$^-$, and CD117$^-$ enhanced placental stem cells. In a specific embodiment, said isolated enhanced placental stem cells or population of isolated enhanced placental stem cells is isolated away from placental cells that are not said cells. In another specific embodiment, said isolated enhanced placental stem cells are non-maternal in origin. In another specific embodiment, at least about 40%, 45%, 50%, 55%, 60%, 65%, 70%, 75%, 90%, 85%, 90%, 95%, 98% or 99% of said enhanced placental stem cells in said cell population are non-maternal in origin. In another specific embodiment, said isolated enhanced placental stem cells or population of isolated enhanced placental stem cells is isolated away from placental cells that do not display these markers.

In another embodiment, the isolated enhanced placental stem cells useful in the methods and compositions described herein are isolated $CD10^+$ $CD13^-$, $CD33^-$, $CD45^-$, and $CD117^-$ enhanced placental stem cells. In another embodiment, a cell population useful in the methods and compositions described herein is a population of cells comprising, e.g., enriched for, isolated $CD10^+$, $CD13^-$, $CD33^-$, $CD45^-$, and $CD117^-$ enhanced placental stem cells, wherein at least about 70%, at least about 80%, at least about 90%, at least about 95% or at least about 99% of cells in said population are $CD10^+$ $CD13^-$, $CD33^-$, $CD45^-$, and $CD117^-$ enhanced placental stem cells. In a specific embodiment, said isolated enhanced placental stem cells or population of isolated enhanced placental stem cells are isolated away from placental cells that are not said enhanced placental stem cells. In another specific embodiment, said isolated placental cells are non-maternal in origin. In another specific embodiment, at least about 40%, 45%, 50%, 55%, 60%, 65%, 70%, 75%, 90%, 85%, 90%, 95%, 98% or 99% of said cells in said cell population are non-maternal in origin. In another specific embodiment, said isolated enhanced placental stem cells or population of isolated enhanced placental stem cells is isolated away from placental cells that do not display these characteristics.

In another embodiment, the isolated enhanced placental stem cells useful in the methods and compositions described herein are HLA $CD45^-$, $CD34^-$, and $CD133^-$, and are additionally $CD10^+$, $CD13^+$, $CD38^+$, $CD44^+$, $CD90^+$, $CD105^+$, $CD200^+$ and/or HLA-$G^-$, and/or negative for CD117. In another embodiment, a cell population useful in the methods described herein is a population of cells comprising isolated enhanced placental stem cells, wherein at least about 20%, 25%, 30%, 35%, 40%, 45%, 50%, 55%, 60%, 65%, 70%, 75%, 80%, 85%, 90%, 95%, 98% or about 99% of the cells in said population are isolated enhanced placental stem cells that are HLA A,B,$C^-$, $CD45^-$, $CD34^-$, $CD133^-$, and that are additionally positive for CD10, CD13, CD38, CD44, CD90, CD105, CD200, and/or negative for CD117 and/or HLA-$G^-$. In a specific embodiment, said isolated enhanced placental stem cells or population of isolated enhanced placental stem cells are isolated away from placental cells that are not said enhanced placental stem cells. In another specific embodiment, said isolated enhanced placental stem cells are non-maternal in origin. In another specific embodiment, at least about 40%, 45%, 50%, 55%, 60%, 65%, 70%, 75%, 90%, 85%, 90%, 95%, 98% or 99% of said enhanced placental stem cells in said cell population are non-maternal in origin. In another specific embodiment, said isolated enhanced placental stem cells or population of isolated enhanced placental stem cells are isolated away from placental cells that do not display these characteristics.

In another embodiment, the isolated enhanced placental stem cells are isolated enhanced placental stem cells that are $CD200^+$ and $CD10^+$, as determined by antibody binding, and $CD117^-$, as determined by both antibody binding and RT-PCR. In another embodiment, the isolated enhanced placental stem cells are isolated placental stem cells that are $CD10^+$, $CD29^-$, $CD54^+$, $CD200^+$, HLA-$G^-$, MEW class $I^+$ and β-2-microglobulin$^+$. In another embodiment, isolated enhanced placental stem cells useful in the methods and compositions described herein are enhanced placental stem cells wherein the expression of at least one cellular marker is at least two-fold higher than in an equivalent number of mesenchymal stem cells, e.g., bone marrow-derived mesenchymal stem cells. In another specific embodiment, said isolated enhanced placental stem cells are non-maternal in origin. In another specific embodiment, at least about 40%, 45%, 50%, 55%, 60%, 65%, 70%, 75%, 90%, 85%, 90%, 95%, 98% or 99% of said cells in said cell population are non-maternal in origin.

In another embodiment, the isolated enhanced placental stem cells are isolated enhanced placental stem cells that are one or more of $CD10^+$, $CD29^+$, $CD44^+$, $CD45^-$, CD54/ ICAM$^+$, $CD62E^-$, $CD62L^-$, $CD62P^-$, $CD80^-$, $CD86^-$, $CD103^-$, $CD104^-$, $CD105^+$, CD106/VCAM$^+$, CD144/VE-cadherin$^{low}$, $CD184/CXCR4^-$, β2-microglobulin$^{low}$, MHC-$II^-$, HLA-$G^{low}$, and/or PDL1$^{low}$. In a specific embodiment, the isolated enhanced placental stem cells are at least $CD29^+$ and $CD54^+$. In another specific embodiment, the isolated enhanced placental stem cells are at least $CD44^+$ and $CD106^+$. In another specific embodiment, the isolated enhanced placental stem cells are at least $CD29^+$.

In another embodiment, a cell population useful in the methods and compositions described herein comprises isolated enhanced placental stem cells, and at least 50%, 60%, 70%, 80%, 90%, 95%, 98% or 99% of the cells in said cell population are isolated enhanced placental stem cells that are one or more of $CD10^+$, $CD29^+$, $CD44^+$, $CD45^-$, CD54/ ICAM$^+$, CD62-$E^-$, CD62-$L^-$, CD62-$P^-$, $CD80^-$, $CD86^-$, $CD103^-$, $CD104^-$, $CD105^+$, CD106/VCAM$^+$, CD144/VE-cadherin$^{dim}$, $CD184/CXCR4^-$, β2-microglobulin$^{dim}$, HLA-$I^{dim}$, HLA-$II^-$, HLA-$G^{dim}$, and/or PDL1$^{dim}$ enhanced placental stem cells. In another specific embodiment, at least 50%, 60%, 70%, 80%, 90%, 95%, 98% or 99% of cells in said cell population are $CD10^+$, $CD29^+$, $CD44^+$, $CD45^-$, CD54/ICAM$^+$, CD62-$E^-$, CD62-$L^-$, CD62-$P^-$, $CD80^-$, $CD86^-$, $CD103^-$, $CD104^-$, $CD105^+$, CD106/VCAM$^+$, CD144/VE-cadherin$^{dim}$, $CD184/CXCR4^-$, β2-microglobulin$^{dim}$, MHC-$I^{dim}$, MHC-$II^-$, HLA-$G^{dim}$, and PDL1$^{dim}$ enhanced placental stem cells. In certain embodiments, the enhanced placental stem cells express HLA-II markers when induced by interferon gamma (IFN-γ).

In another embodiment, the isolated enhanced placental stem cells useful in the methods and compositions described herein are isolated enhanced placental stem cells that are one or more, or all, of $CD10^+$, $CD29^+$, $CD34^-$, $CD38^-$, $CD44^+$, $CD45^-$, $CD54^+$, $CD90^+$, $SH2^+$, $SH3^+$, $SH4^+$, $SSEA3^-$, $SSEA4^-$, OCT-$4^+$, and ABC-$p^+$, where ABC-p is a placenta-specific ABC transporter protein (also known as breast cancer resistance protein (BCRP) or as mitoxantrone resistance protein (MXR)), wherein said isolated enhanced placental stem cells are derived from placental stem cells obtained by perfusion of a mammalian, e.g., human, placenta that has been drained of cord blood and perfused to remove residual blood.

In another specific embodiment of any of the above embodiments, expression of the recited cellular marker(s) (e.g., cluster of differentiation or immunogenic marker(s)) is determined by flow cytometry. In another specific embodiment, expression of the marker(s) is determined by RT-PCR.

Gene profiling confirms that isolated enhanced placental stem cells, and populations of isolated enhanced placental stem cells, are distinguishable from other cells, e.g., mesenchymal stem cells, e.g., bone marrow-derived mesenchymal stem cells. The isolated enhanced placental stem cells described herein can be distinguished from, e.g., bone marrow-derived mesenchymal stem cells on the basis of the expression of one or more genes, the expression of which is significantly higher in the isolated enhanced placental stem cells in comparison to bone marrow-derived mesenchymal stem cells. In particular, the isolated enhanced placental stem cells, useful in the methods of treatment provided herein, can be distinguished from bone marrow-derived mesenchymal stem cells on the basis of the expression of one or more genes, the expression of which is significantly higher (that is, at least twofold higher) in the isolated enhanced placental stem cells than in an equivalent number of bone marrow-derived mesenchymal stem cells, wherein the one or more gene comprise ACTG2, ADARB1, AMIGO2, ARTS-1, B4GALT6, BCHE, C11orf9, CD200, COL4A1, COL4A2, CPA4, DMD, DSC3, DSG2, ELOVL2, F2RL1, FLJ10781, GATA6, GPR126, GPRC5B, ICAM1, IER3, IGFBP7, IL1A, IL6, IL18, KRT18, KRT8, LIPG, LRAP, MATN2, MEST, NFE2L3, NUAK1, PCDH7, PDLIM3, PKP2, RTN1, SERPINB9, ST3GAL6, ST6GALNAC5, SLC12A8, TCF21, TGFB2, VTN, ZC3H12A, or a combination of any of the foregoing, when the cells are grown under equivalent conditions. See, e.g., U.S. Patent Application Publication No. 2007/0275362, the disclosure of which is incorporated herein by reference in its entirety. In certain specific embodiments, said expression of said one or more genes is determined, e.g., by RT-PCR or microarray analysis, e.g., using a U133-A microarray (Affymetrix).

In another specific embodiment, said isolated enhanced placental stem cells express said one or more genes when cultured for a number of population doublings, e.g., anywhere from about 3 to about 35 population doublings, in a medium comprising DMEM-LG (e.g., from Gibco); 2% fetal calf serum (e.g., from Hyclone Labs.); 1× insulin-transferrin-selenium (ITS); 1× linoleic acid-bovine serum albumin (LA-BSA); $10^{-9}$M dexamethasone (e.g., from Sigma); $10^{-4}$ M ascorbic acid 2-phosphate (e.g., from Sigma); epidermal growth factor 10 ng/mL (e.g., from R&D Systems); and platelet-derived growth factor (PDGF-BB) 10 ng/mL (e.g., from R&D Systems). In another specific embodiment, the placental cell-specific gene is CD200.

Specific sequences for these genes can be found in GenBank at accession nos. NM_001615 (ACTG2), BC065545 (ADARB1), (NM_181847 (AMIGO2), AY358590 (ARTS-1), BC074884 (B4GALT6), BC008396 (BCHE), BC020196 (C11orf9), BC031103 (CD200), NM_001845 (COL4A1), NM_001846 (COL4A2), BC052289 (CPA4), BC094758 (DMD), AF293359 (DSC3), NM_001943 (DSG2), AF338241 (ELOVL2), AY336105 (F2RL1), NM_018215 (FLJ10781), AY416799 (GATA6), BC075798 (GPR126), NM_016235 (GPRC5B), AF340038 (ICAM1), BC000844 (IER3), BC066339 (IGFBP7), BC013142 (IL1A), BT019749 (IL6), BC007461 (IL18), (BC072017) KRT18, BC075839 (KRT8), BC060825 (LIPG), BC065240 (LRAP), BC010444 (MATN2), BC011908 (MEST), BC068455 (NFE2L3), NM_014840 (NUAK1), AB006755 (PCDH7), NM_014476 (PDLIM3), BC126199 (PKP-2), BC090862 (RTN1), BC002538 (SERPINB9), BC023312 (ST3GAL6), BC001201 (ST6GALNAC5), BC126160 or BC065328 (SLC12A8), BC025697 (TCF21), BC096235 (TGFB2), BC005046 (VTN), and BC005001 (ZC3H12A) as of March 2008.

In certain specific embodiments, said isolated enhanced placental stem cells express each of ACTG2, ADARB1, AMIGO2, ARTS-1, B4GALT6, BCHE, C11orf9, CD200, COL4A1, COL4A2, CPA4, DMD, DSC3, DSG2, ELOVL2, F2RL1, F1110781, GATA6, GPR126, GPRC5B, ICAM1, IER3, IGFBP7, IL1A, IL6, IL18, KRT18, KRT8, LIPG, LRAP, MATN2, MEST, NFE2L3, NUAK1, PCDH7, PDLIM3, PKP2, RTN1, SERPINB9, ST3GAL6, ST6GALNAC5, SLC12A8, TCF21, TGFB2, VTN, and ZC3H12A at a detectably higher level than an equivalent number of bone marrow-derived mesenchymal stem cells, when the cells are grown under equivalent conditions.

In specific embodiments, the enhanced placental stem cells express CD200 and ARTS1 (aminopeptidase regulator of type 1 tumor necrosis factor); ARTS-1 and LRAP (leukocyte-derived arginine aminopeptidase); IL6 (interleukin-6) and TGFB2 (transforming growth factor, beta 2); IL6 and KRT18 (keratin 18); IER3 (immediate early response 3), MEST (mesoderm specific transcript homolog) and TGFB2; CD200 and IER3; CD200 and IL6; CD200 and KRT18; CD200 and LRAP; CD200 and MEST; CD200 and NFE2L3 (nuclear factor (erythroid-derived 2)-like 3); or CD200 and TGFB2 at a detectably higher level than an equivalent number of bone marrow-derived mesenchymal stem cells wherein said bone marrow-derived mesenchymal stem cells have undergone a number of passages in culture equivalent to the number of passages said isolated placental stem cells have undergone. In other specific embodiments, the enhanced placental stem cells express ARTS-1, CD200, IL6 and LRAP; ARTS-1, IL6, TGFB2, IER3, KRT18 and MEST; CD200, IER3, IL6, KRT18, LRAP, MEST, NFE2L3, and TGFB2; ARTS-1, CD200, IER3, IL6, KRT18, LRAP, MEST, NFE2L3, and TGFB2; or IER3, MEST and TGFB2 at a detectably higher level than an equivalent number of bone marrow-derived mesenchymal stem cells, wherein said bone marrow-derived mesenchymal stem cells have undergone a number of passages in culture equivalent to the number of passages said isolated enhanced placental stem cells have undergone.

Expression of the above-referenced genes can be assessed by standard techniques. For example, probes based on the sequence of the gene(s) can be individually selected and constructed by conventional techniques. Expression of the genes can be assessed, e.g., on a microarray comprising probes to one or more of the genes, e.g., an Affymetrix GENECHIP® Human Genome U133A 2.0 array, or an Affymetrix GENECHIP® Human Genome U133 Plus 2.0 (Santa Clara, Calif.). Expression of these genes can be assessed even if the sequence for a particular GenBank accession number is amended because probes specific for the amended sequence can readily be generated using well-known standard techniques.

The level of expression of these genes can be used to confirm the identity of a population of isolated enhanced placental stem cells, to identify a population of cells as comprising at least a plurality of isolated enhanced placental stem cells, or the like. Populations of isolated enhanced placental stem cells, the identity of which is confirmed, can be clonal, e.g., populations of isolated enhanced placental stem cells expanded from a single isolated enhanced placental stem cell, or a mixed population of enhanced placental stem cells, e.g., a population of cells comprising isolated enhanced placental stem cells that are expanded from multiple isolated enhanced placental stem cells, or a population of cells comprising isolated enhanced placental stem cells, as described herein, and at least one other type of cell.

The level of expression of these genes can be used to select populations of isolated enhanced placental stem cells. For example, a population of cells, e.g., clonally-expanded enhanced placental stem cells, may be selected if the expression of one or more of the genes listed above is significantly higher in a sample from the population of cells than in an equivalent population of bone marrow-derived mesenchymal stem cells. Such selecting can be of a population from a plurality of isolated enhanced placental stem cell populations, from a plurality of cell populations, the identity of which is not known, etc.

Isolated enhanced placental stem cells can be selected on the basis of the level of expression of one or more such genes as compared to the level of expression in said one or more genes in, e.g., a bone marrow-derived mesenchymal stem cell control. In one embodiment, the level of expression of said one or more genes in a sample comprising an equivalent number of bone marrow-derived mesenchymal stem cells is used as a control. In another embodiment, the control, for isolated enhanced placental stem cells tested under certain conditions, is a numeric value representing the level of expression of said one or more genes in bone marrow-derived mesenchymal stem cells under said conditions.

Similarly, the expression of survival-associated genes can be used to select populations of isolated enhanced placental stem cells. For example, a population of cells, e.g., clonally-expanded enhanced placental stem cells, may be selected if the expression of one or more survival-associated genes (e.g., one or more of the survival-associated genes described herein) is increased or decreased in a sample from the population of cells relative an equivalent population of unmodified placental stem cells.

The isolated enhanced placental stem cells described herein display the above characteristics (e.g., combinations of cell surface markers and/or gene expression profiles) in primary culture, or during proliferation in medium comprising, e.g., DMEM-LG (Gibco), 2% fetal calf serum (FCS) (Hyclone Laboratories), 1× insulin-transferrin-selenium (ITS), 1× linoleic-acid-bovine-serum-albumin (LA-BSA), $10^{-9}$M dexamethasone (Sigma), $10^{-4}$M ascorbic acid 2-phosphate (Sigma), epidermal growth factor (EGF) 10 ng/ml (R&D Systems), platelet derived-growth factor (PDGF-BB) 10 ng/ml (R&D Systems), and 100 U penicillin/ 1000 U streptomycin.

In certain embodiments of any of the enhanced placental stem cells disclosed herein, the cells are human. In certain embodiments of any of the enhanced placental stem cells disclosed herein, the cellular marker characteristics or gene expression characteristics are human markers or human genes.

In another specific embodiment of the isolated enhanced placental stem cells or populations of cells comprising the isolated enhanced placental stem cells, said cells or population have been expanded, for example, passaged at least, about, or no more than, 1, 2, 3, 4, 5, 6, 7, 8, 9, 10, 11, 12, 13, 14, 15, 16, 17, 18, 19, or 20 times, or proliferated for at least, about, or no more than, 1, 2, 3, 4, 5, 6, 7, 8, 9, 10, 12, 14, 16, 18, 20, 22, 24, 26, 28, 30, 32, 34, 36, 38 or 40 population doublings. In another specific embodiment of said isolated enhanced placental stem cells or populations of cells comprising the isolated enhanced placental stem cells, said cells or population are primary isolates. In another specific embodiment of the isolated enhanced placental stem cells, or populations of cells comprising isolated enhanced placental stem cells, that are disclosed herein, said isolated enhanced placental stem cells are fetal in origin (that is, have the fetal genotype).

In certain embodiments, said isolated enhanced placental stem cells do not differentiate during culturing in growth medium, i.e., medium formulated to promote proliferation, e.g., during proliferation in growth medium. In another specific embodiment, said isolated enhanced placental stem cells do not require a feeder layer in order to proliferate. In another specific embodiment, said isolated enhanced placental stem cells do not differentiate in culture in the absence of a feeder layer, solely because of the lack of a feeder cell layer.

In another embodiment, the isolated enhanced placental stem cells are positive for aldehyde dehydrogenase (ALDH), as assessed by an aldehyde dehydrogenase activity assay. Such assays are known in the art (see, e.g., Bostian and Betts, *Biochem. J.*, 173, 787, (1978)). In a specific embodiment, said ALDH assay uses ALDEFLUOR® (Aldagen, Inc., Ashland, Oreg.) as a marker of aldehyde dehydrogenase activity. In a specific embodiment, between about 3% and about 25% of enhanced placental stem cells are positive for ALDH. In another embodiment, said isolated enhanced placental stem cells show at least three-fold, or at least five-fold, higher ALDH activity than a population of bone marrow-derived mesenchymal stem cells having about the same number of cells and cultured under the same conditions.

In certain embodiments of any of the populations of cells comprising the isolated enhanced placental stem cells described herein, the enhanced placental stem cells in said populations of cells are substantially free of cells having a maternal genotype; e.g., at least 40%, 45%, 50%, 55%, 60%, 65%, 70%, 75%, 80%, 85%, 90%, 95%, 98% or 99% of the enhanced placental stem cells in said population have a fetal genotype. In certain other embodiments of any of the populations of cells comprising the isolated enhanced placental stem cells described herein, the populations of cells comprising said enhanced placental stem cells are substantially free of cells having a maternal genotype; e.g., at least 40%, 45%, 50%, 55%, 60%, 65%, 70%, 75%, 80%, 85%, 90%, 95%, 98% or 99% of the cells in said population have a fetal genotype.

In a specific embodiment of any of the above isolated enhanced placental stem cells or cell populations comprising isolated enhanced placental stem cells, the karyotype of the cells, e.g., all of the cells, or at least about 95% or about 99% of the cells in said population, is normal. In another specific embodiment of any of the above enhanced placental stem cells or populations or enhanced placental stem cells, the enhanced placental stem cells are non-maternal in origin.

In a specific embodiment of any of the embodiments of placental cells disclosed herein, the placental cells are genetically stable, displaying a normal diploid chromosome count and a normal karyotype.

Isolated enhanced placental stem cells, or populations of isolated enhanced placental stem cells, bearing any of the above combinations of markers, can be combined in any ratio. Any two or more of the above isolated enhanced placental stem cells populations can be combined to form an isolated enhanced placental stem cell population. For example, a population of isolated enhanced placental stem cells can comprise a first population of isolated enhanced placental stem cells defined by one of the marker combinations described above, and a second population of isolated enhanced placental stem cells defined by another of the marker combinations described above, wherein said first and second populations are combined in a ratio of about 1:99, 2:98, 3:97, 4:96, 5:95, 10:90, 20:80, 30:70, 40:60, 50:50, 60:40, 70:30, 80:20, 90:10, 95:5, 96:4, 97:3, 98:2, or about 99:1. In like fashion, any three, four, five or more of the above-described isolated enhanced placental stem cells or isolated placental stem cell populations can be combined.

Isolated placental stem cells useful in methods for generating the enhanced placental stem cells described herein can be obtained, e.g., by disruption of placental tissue, with or without enzymatic digestion or perfusion. For example, populations of isolated placental stem cells can be produced according to a method comprising perfusing a mammalian placenta that has been drained of cord blood and perfused to remove residual blood; perfusing said placenta with a perfusion solution; and collecting said perfusion solution, wherein said perfusion solution after perfusion comprises a population of placental cells that comprises isolated placental stem cells; and isolating said placental stem cells from said population of cells. In a specific embodiment, the perfusion solution is passed through both the umbilical vein and umbilical arteries and collected after it exudes from the placenta. In another specific embodiment, the perfusion solution is passed through the umbilical vein and collected from the umbilical arteries, or passed through the umbilical arteries and collected from the umbilical vein.

In various embodiments, the isolated placental stem cells, useful in methods for generating the enhanced placental stem cells described herein contained within a population of cells obtained from perfusion of a placenta, are at least 50%, 60%, 70%, 80%, 90%, 95%, 99% or at least 99.5% of said population of placental stem cells. In another specific embodiment, the isolated placental stem cells collected by perfusion comprise fetal and maternal cells. In another specific embodiment, the isolated placental stem cells collected by perfusion are at least 50%, 60%, 70%, 80%, 90%, 95%, 99% or at least 99.5% fetal cells.

In another specific embodiment, provided herein is a composition comprising a population of the isolated placental stem cells useful in methods for generating the enhanced placental stem cells described herein, collected (isolated) by perfusion, wherein said composition comprises at least a portion of the perfusion solution used to isolate the placental stem cells.

Populations of the isolated placental stem cells useful in methods for generating the enhanced placental stem cells described herein can be produced by digesting placental tissue with a tissue-disrupting enzyme to obtain a population of placental cells comprising the placental stem cells, and isolating, or substantially isolating, a plurality of the placental stem cells from the remainder of said placental cells. The whole, or any part of, the placenta can be digested to obtain the isolated placental stem cells described herein. In specific embodiments, for example, said placental tissue can be a whole placenta (e.g., including an umbilical cord), an amniotic membrane, chorion, a combination of amnion and chorion, or a combination of any of the foregoing. In other specific embodiments, the tissue-disrupting enzyme is trypsin or collagenase. In various embodiments, the isolated placental stem cells, contained within a population of cells obtained from digesting a placenta, are at least 50%, 60%, 70%, 80%, 90%, 95%, 99% or at least 99.5% of said population of placental cells.

The populations of isolated enhanced placental stem cells described above, and populations of isolated enhanced placental stem cells generally, can comprise about, at least, or no more than, $1\times10^5$, $5\times10^5$, $1\times10^6$, $5\times10^6$, $1\times10^7$, $5\times10^7$, $1\times10^8$, $5\times10^8$, $1\times10^9$, $5\times10^9$, $1\times10^{10}$, $5\times10^{10}$, $1\times10^{11}$ or more of the isolated enhanced placental stem cells. Populations of isolated enhanced placental stem cells useful in the methods and compositions described herein comprise at least 50%, 55%, 60%, 65%, 70%, 75%, 80%, 85%, 90%, 95%, 98%, or 99% viable isolated placental stem cells, e.g., as determined by, e.g., trypan blue exclusion.

For any of the above placental stem cells, or populations of placental stem cells, (e.g., unmodified placental stem cells useful in methods of producing the enhanced placental stem cells described herein, or the enhanced placental stem cells described herein, or compositions thereof) the cells or population of placental stem cells are, or can comprise, cells that have been passaged at least 1, 2, 3, 4, 5, 6, 7, 8, 9, 10, 12, 14, 16, 18, or 20 times, or more, or expanded for 1, 2, 3, 4, 5, 6, 7, 8, 9, 10, 12, 14, 16, 18, 20, 22, 24, 26, 28, 30, 32, 34, 36, 38 or 40 population doublings, or more.

In a specific embodiment of any of the above placental stem cells or placental stem cells populations (e.g., unmodified placental stem cells useful in methods of producing the enhanced placental stem cells described herein, or the enhanced placental stem cells described herein, or compositions thereof), the karyotype of the cells, or at least about 95% or about 99% of the cells in said population, is normal. In another specific embodiment of any of the above placental stem cells or placental stem cells populations (e.g., unmodified placental stem cells useful in methods of producing the enhanced placental stem cells described herein, or the enhanced placental stem cells described herein, or compositions thereof), the cells, or cells in the population of cells, are non-maternal in origin.

Isolated placental stem cells, or populations of isolated placental stem cells, (e.g., unmodified placental stem cells useful in methods of producing the enhanced placental stem cells described herein, or the enhanced placental stem cells described herein, or compositions thereof) bearing any of the above combinations of markers, can be combined in any ratio. Any two or more of the above placental stem cells populations can be isolated, or enriched, to form a placental stem cells population. For example, an population of isolated placental stem cells comprising a first population of placental stem cells defined by one of the marker combinations described above can be combined with a second population of placental stem cells defined by another of the marker combinations described above, wherein said first and second populations are combined in a ratio of about 1:99, 2:98, 3:97, 4:96, 5:95, 10:90, 20:80, 30:70, 40:60, 50:50, 60:40, 70:30, 80:20, 90:10, 95:5, 96:4, 97:3, 98:2, or about 99:1. In like fashion, any three, four, five or more of the above-described placental stem cells or placental stem cells populations can be combined.

In a specific embodiment of the above-mentioned placental stem cells (e.g., unmodified placental stem cells useful in methods of producing the enhanced placental stem cells described herein, or the enhanced placental stem cells described herein, or compositions thereof), the placental stem cells constitutively secrete IL-6, IL-8 and monocyte chemoattractant protein (MCP-1).

In certain embodiments, the enhanced placental stem cells useful in the methods provided herein, do not express CD34, as detected by immunolocalization, after exposure to 1 to 100 ng/mL VEGF for 4 to 21 days. In another specific embodiment, said enhanced placental stem cells induce endothelial cells to form sprouts or tube-like structures, e.g., when cultured in the presence of an angiogenic factor such as vascular endothelial growth factor (VEGF), epithelial growth factor (EGF), platelet derived growth factor (PDGF) or basic fibroblast growth factor (bFGF), e.g., on a substrate such as MATRIGEL™.

In another aspect, the enhanced placental stem cells provided herein, or a population of cells, e.g., a population of enhanced placental stem cells, or a population of cells wherein at least about 50%, 60%, 70%, 80%, 90%, 95% or 98% of cells in said population of cells are enhanced placental stem cells, secrete one or more, or all, of VEGF, HGF, IL-8, MCP-3, FGF2, follistatin, G-CSF, EGF, ENA- 78, GRO, IL-6, MCP-1, PDGF-BB, TIMP-2, uPAR, or galectin-1, e.g., into culture medium in which the cell, or cells, are grown. In another embodiment, the enhanced placental stem cells express increased levels of CD202b, IL-8 and/or VEGF under hypoxic conditions (e.g., less than about 5% 02) compared to normoxic conditions (e.g., about 20% or about 21% 02).

In another embodiment, any of the enhanced placental stem cells or populations of cells comprising enhanced placental stem cells described herein can cause the formation of sprouts or tube-like structures in a population of endothelial cells in contact with said enhanced placental stem cells. In a specific embodiment, the enhanced placental stem cells are co-cultured with human endothelial cells, which form sprouts or tube-like structures, or support the formation of endothelial cell sprouts, e.g., when cultured in the presence of extracellular matrix proteins such as collagen type I and IV, and/or angiogenic factors such as vascular endothelial growth factor (VEGF), epithelial growth factor (EGF), platelet derived growth factor (PDGF) or basic fibroblast growth factor (bFGF), e.g., in or on a substrate such as placental collagen or MATRIGEL™ for at least 4 days. In another embodiment, any of the populations of cells comprising enhanced placental stem cells described herein secrete angiogenic factors such as vascular endothelial growth factor (VEGF), hepatocyte growth factor (HGF), platelet derived growth factor (PDGF), basic fibroblast growth factor (bFGF), or Interleukin-8 (IL-8) and thereby can induce human endothelial cells to form sprouts or tube-like structures when cultured in the presence of extracellular matrix proteins such as collagen type I and IV e.g., in or on a substrate such as placental collagen or MATRIGEL™.

In another embodiment, any of the above populations of cells comprising enhanced placental stem cells secretes angiogenic factors. In specific embodiments, the population of cells secretes vascular endothelial growth factor (VEGF), hepatocyte growth factor (HGF), platelet derived growth factor (PDGF), basic fibroblast growth factor (bFGF), and/or interleukin-8 (IL-8). In other specific embodiments, the population of cells comprising enhanced placental stem cells secretes one or more angiogenic factors and thereby induces human endothelial cells to migrate in an in vitro wound healing assay. In other specific embodiments, the population of cells comprising enhanced placental stem cells induces maturation, differentiation or proliferation of human endothelial cells, endothelial progenitors, myocytes or myoblasts.

In another embodiment, provided herein are enhanced placental stem cells, and populations of enhanced placental stem cells, wherein said enhanced placental stem cells comprise any of the foregoing characteristics (e.g., are CD34$^-$, CD10$^+$, CD105$^+$ and CD200$^+$), and wherein at least one survival-associated gene is downregulated/inhibited in said enhanced placental stem cells relative to the level of expression of said survival-associated gene in an equivalent number of unmodified placental stem cells (e.g., CD34$^-$, CD10$^+$, CD105$^+$ and CD200$^+$ unmodified placental stem cells). In a specific embodiment, the at least one survival-associated gene is ADAMTS9, ABCF2, DNAJB4, MYB, RTN4, ANLN, BACE1, ABHD10, EGFR, NAA15, SEC24A MAP2K1, BCL2, ACTR1A, EIF4E, NAA25, SHOC2, CCNF, CAV2, ACVR2A, EPT1, NAPG, SLC12A2, CDC14A, CD276, ADSS, FGF2, NOB1, SLC16A3, CDC25A, CDC42, ALG3, FNDC3B, NOTCH2, SLC25A22, CHEK1, CDK6, ARHGDIA, GALNT7, SLC38A5, CUL2, COL3A1, ARL2, GPAM, PDCD4, SLC7A1, FGFR1, COL4A1, ATG9A, HACE1, PDCD6IP, SNX15, ITPR1, COL4A2, PLAG1, HARS, PHKB, SPTLC1, KIF23, CPEB3, C9ORF167/TOR4A, HARS2, PISD, SQSTM1, TRIM63, CXXC6/TET1, C9ORF89, HERC6, PLK1, SRPR, CSHL1, DIABLO, CACNA2D1, HMGA1, PNN, SRPRB, WEE1, DNMT3A, CAPRIN1, HSDL2, PNPLA6, TMEM43, MLLT1, DNMT3B, CCDC109A/MCU, IGF2R, PPIF, TNFSF9, MMS19, FGA, CCND1, IPO4, SIAH1, TOMM34, RECK, IMPDH1, CCND3, ITGA2, PPP2R5C, TPM3, RNASEL, INSIG1, CCNE1, KCNN4, PSAT1, TPPP3, WT1, KREMEN2, CCNT2, KPNA3, PTCD3, UBE2V1, YIF1B, LPL, CDC14B, LAMC1, PTGS2, UBE4A, ZNF622, MCL1, CDK5RAP1, LAMTOR3, PURA, UGDH, PIK3R1, CENPJ, LUZP1, RAB9B, UTP15, PPM1D, CHORDC1, LYPLA2, RAD51C, VEGFA, SPARC, CREBL2, PIAS1, RARS, or WNT3A. In a specific embodiment, 2, 3, 4, 5, 6, 7, 8, 9, 10, or more than 10 of said survival-associated genes are downregulated/inhibited in said enhanced placental stem cells relative to the level of expression of said survival-associated gene (s) in an equivalent number of unmodified placental stem cells (e.g., CD34$^-$, CD10$^+$, CD105$^+$ and CD200$^+$ unmodified placental stem cells).

In another specific embodiment, provided herein is an isolated CD34$^-$, CD10$^+$, CD105$^+$ and CD200$^+$ enhanced placental stem cell, wherein said enhanced placental stem cell expresses the survival-associated gene CCND1, CCND3, CCNE1, CCNF, CDK6, PPP2R5C, CDC25A, WEE1, CHEK1, MCL1, BCL2, PPMID, HMGA1, AKT3, VEGFA, MYB, or ITGA2 at a decreased level as compared to the expression of the survival-associated gene in an unmodified CD34$^-$, CD10$^+$, CD105$^+$ and CD200$^+$ placental stem cell. In another specific embodiment, provided herein is an isolated CD34$^-$, CD10$^+$, CD105$^+$ and CD200$^+$ enhanced placental stem cell, wherein said enhanced placental stem cell expresses one, two, three, or more of the following placental stem cell survival-associated genes at a decreased level as compared to the expression of the same survival-associated gene (s) in a corresponding unmodified placental stem cell: CCND1, CCND3, CCNE1, CCNF, CDK6, PPP2R5C, CDC25A, WEE1, CHEK1, MCL1, BCL2, PPMID, HMGA1, AKT3, VEGFA, MYB, or ITGA2. In another specific embodiment, provided herein is an isolated CD34$^-$, CD10$^+$, CD105$^+$ and CD200$^+$ enhanced placental stem cell, wherein said enhanced placental stem cell (i) expresses one, two, three, or more of the following placental stem cell survival-associated genes at a decreased level as compared to the expression of the same survival-associated gene (s) in a corresponding unmodified placental stem cell: CCND1, CCND3, CCNE1, CCNF, CDK6, PPP2R5C, CDC25A, WEE1, CHEK1, MCL1, BCL2, PPMID, HMGA1, AKT3, VEGFA, MYB, or ITGA2; and (ii) expresses at least one additional survival-associated gene recited in Table 1 at an increased or a decreased level as compared to the expression of the same survival-associated gene (s) in a corresponding unmodified placental stem cell. Further provided herein are populations of cells comprising such enhanced placental stem cells and compositions comprising such enhanced placental stem cells.

In another specific embodiment, provided herein is an isolated CD34$^-$, CD10$^+$, CD105$^+$ and CD200$^+$ enhanced placental stem cell, wherein said enhanced placental stem cell expresses one, two, three, or more (i.e., a combination) of the following placental stem cell survival-associated genes at an increased level as compared to the expression of the same survival-associated gene(s) in a corresponding unmodified CD34$^-$, CD10$^+$, CD105$^+$ and CD200$^+$ placental stem cell: CCND1, CCND3, CCNE1, PPP2R5C, CDC25A, WEE1, MCL1, PPMID, HMGA1, AKT3, VEGFA, PPP2R5C, and/or ITGA2. In another specific embodiment, provided herein is an isolated CD34$^-$, CD10$^+$, CD105$^+$ and CD200$^+$ enhanced placental stem cell, wherein said enhanced placental stem cell expresses one, two, three, or more of the following placental stem cell survival-associated genes at an increased level as compared to the expression of the same survival-associated gene (s) in a corresponding unmodified CD34$^-$, CD10$^+$, CD105$^+$ and CD200$^+$ placental stem cell: CCND1, CCND3, CCNE1, PPP2R5C, CDC25A, WEE1, MCL1, PPMID, HMGA1, AKT3, VEGFA, PPP2R5C, and/or ITGA2. In another specific embodiment, provided herein is an isolated CD34$^-$, CD10$^+$, CD105$^+$ and CD200$^+$ enhanced placental stem cell, wherein said enhanced placental stem cell (i) expresses one, two, three, or more of the following placental stem cell survival-associated genes at an increased level as compared to the expression of the same survival-associated gene(s) in a corresponding unmodified CD34$^-$, CD10$^+$, CD105$^+$ and CD200$^+$ placental stem cell: CCND1, CCND3, CCNE1, PPP2R5C, CDC25A, WEE1, MCL1, PPMID, HMGA1, AKT3, VEGFA, PPP2R5C, and/or ITGA2; and (ii) expresses at least one additional survival-associated gene recited in Table 1 at an increased or a decreased level as compared to the expression of the same survival-associated gene (s) in a corresponding unmodified placental stem cell. Further provided herein are populations of cells comprising such enhanced placental stem cells and compositions comprising such enhanced placental stem cells.

5.3.3 Growth in Culture

The growth of placental cells, including the enhanced placental stem cells described herein, as for any mammalian cell, depends in part upon the particular medium selected for growth. During culture, the placental stem cells used in the methods of production of the enhanced placental stem cells provided herein adhere to a substrate in culture, e.g. the surface of a tissue culture container (e.g., tissue culture dish plastic, fibronectin-coated plastic, and the like) and form a monolayer.

In a specific embodiment, the enhanced placental stem cells described herein demonstrate increased survival relative to corresponding unmodified placental stem cells when cultured under conditions that cause cell death in vitro. In another specific embodiment, the enhanced placental stem cells described herein demonstrate increased survival relative to corresponding unmodified placental stem cells when cultured under conditions that cause cell death in vivo, e.g., when administered to a subject.

In certain embodiments, when cultured under conditions that cause cell death (either in vitro or in vivo), e.g., in the presence of serum (e.g., human or rat serum), complement, antibody(ies), other cells (e.g., cells of the immune system), and/or conditions that can lead to anoikis (e.g., low-attachment conditions) the enhanced placental stem cells described herein demonstrate at least a 1.5-fold, 2-fold, 2.5-fold, 3-fold, 3.5-fold, 4-fold, 4.5-fold, 5-fold, 6-fold, 7-fold, 8-fold, 9-fold, or 10-fold increase in survival relative to an equivalent amount of corresponding unmodified placental stem cells cultured under the same conditions. In certain embodiments, when cultured under conditions that cause cell death (either in vitro or in vivo), e.g., in the presence of serum (e.g., rat serum), complement, antibody(ies), other cells (e.g., cells of the immune system), and/or conditions that can lead to anoikis (e.g., low-attachment conditions) the enhanced placental stem cells described herein demonstrate a 1.5-fold to 2.5-fold, a 2-fold to 3-fold, a 2.5-fold to 3.5-fold, a 3-fold to 4-fold, a 3.5-fold to 4.5-fold, a 4-fold to 5-fold, a 5-fold to 6-fold, a 6-fold to 7-fold, a 7-fold to 8-fold, an 8-fold to 9-fold, or a 9-fold to 10-fold increase in survival relative to an equivalent amount of corresponding unmodified placental stem cells cultured under the same conditions. Survival of the enhanced placental stem cells and unmodified placental stem cells can be assessed using methods known in the art, e.g., trypan blue exclusion assay, fluorescein diacetate uptake assay, propidium iodide uptake assay; thymidine uptake assay, and MTT (3-(4,5-Dimethylthiazol-2-yl)-2,5-diphenyltetrazolium bromide) assay.

In certain embodiments, when cultured under conditions that cause cell death (either in vitro or in vivo), e.g., in the presence of serum (e.g., rat serum), complement, antibody(ies), other cells (e.g., cells of the immune system), and/or conditions that can lead to anoikis (e.g., low-attachment conditions) the enhanced placental stem cells described herein demonstrate (i) decreased caspase 3/7 activity, (ii) increased mitochondrial membrane potential, and/or (iii) increased metabolic activity as compared to corresponding unmodified placental stem cells cultured under the same condition(s). Caspase 3/7 activity, mitochondrial membrane potential, and metabolic activity can be assessed using methods known in the art, e.g., as described in Sections 6.1.1.1.3 and 6.1.1.2, below.

In certain embodiments, when cultured under conditions that cause cell death (either in vitro or in vivo), e.g., in the presence of serum (e.g., rat serum), complement, antibody(ies), cells (e.g., cells of the immune system), and/or conditions that lead to anoikis (e.g., low attachment conditions) the enhanced placental stem cells described herein exhibit (i) at least a 1.5-fold, 2-fold, 2.5-fold, 3-fold, 3.5-fold, 4-fold, 4.5-fold, 5-fold, 6-fold, 7-fold, 8-fold, 9-fold, or 10-fold decrease in caspase 3/7 activity; (ii) at least a 1.5-fold, 2-fold, 2.5-fold, 3-fold, 3.5-fold, 4-fold, 4.5-fold, 5-fold, 6-fold, 7-fold, 8-fold, 9-fold, or 10-fold increase in mitochondrial membrane potential; and/or (iii) at least a 1.5-fold, 2-fold, 2.5-fold, 3-fold, 3.5-fold, 4-fold, 4.5-fold, 5-fold, 6-fold, 7-fold, 8-fold, 9-fold, or 10-fold increase in metabolic activity as compared to corresponding unmodified placental stem cells cultured under the same condition(s).

In certain embodiments, when cultured under conditions that cause cell death (either in vitro or in vivo), e.g., in the presence of serum (e.g., rat serum), complement, antibody(ies), cells (e.g., cells of the immune system), and/or conditions that can lead to anoikis (e.g., low-attachment conditions) the enhanced placental stem cells described herein exhibit (i) at least a 1.5-fold to 2.5-fold, a 2-fold to 3-fold, a 2.5-fold to 3.5-fold, a 3-fold to 4-fold, a 3.5-fold to 4.5-fold, a 4-fold to 5-fold, a 5-fold to 6-fold, a 6-fold to 7-fold, a 7-fold to 8-fold, an 8-fold to 9-fold, or a 9-fold to 10-fold decrease in caspase 3/7 activity; (ii) at least a 1.5-fold to 2.5-fold, a 2-fold to 3-fold, a 2.5-fold to 3.5-fold, a 3-fold to 4-fold, a 3.5-fold to 4.5-fold, a 4-fold to 5-fold, a 5-fold to 6-fold, a 6-fold to 7-fold, a 7-fold to 8-fold, an 8-fold to 9-fold, or a 9-fold to 10-fold increase in mitochondrial membrane potential; and/or (iii) at least a 1.5-fold to 2.5-fold, a 2-fold to 3-fold, a 2.5-fold to 3.5-fold, a 3-fold to 4-fold, a 3.5-fold to 4.5-fold, a 4-fold to 5-fold, a 5-fold to 6-fold, a 6-fold to 7-fold, a 7-fold to 8-fold, an 8-fold to 9-fold, or a 9-fold to 10-fold increase in metabolic activity as compared to corresponding unmodified placental stem cells cultured under the same condition(s).

5.4 Methods of Obtaining Placental Stem Cells for Use in Methods of Generating Enhanced Placental Stem Cells

5.4.1 Stem Cell Collection Composition

Placental stem cells for use in the methods of generating enhanced placental stem cells described herein can be collected and isolated according to the methods provided herein. Generally, placental stem cells are obtained from a mammalian placenta using a physiologically-acceptable solution, e.g., a stem cell collection composition. A stem cell collection composition is described in detail in related U.S. Patent Application Publication No. 20070190042.

The stem cell collection composition can comprise any physiologically-acceptable solution suitable for the collection and/or culture of stem cells, for example, a saline solution (e.g., phosphate-buffered saline, Kreb's solution, modified Kreb's solution, Eagle's solution, 0.9% NaCl. etc.), a culture medium (e.g., DMEM, HDMEM, etc.), and the like.

The stem cell collection composition can comprise one or more components that tend to preserve placental stem cells, that is, prevent the placental stem cells from dying, or delay the death of the placental stem cells, reduce the number of placental stem cells in a population of cells that die, or the like, from the time of collection to the time of culturing. Such components can be, e.g., an apoptosis inhibitor (e.g., a caspase inhibitor or JNK inhibitor); a vasodilator (e.g., magnesium sulfate, an antihypertensive drug, atrial natriuretic peptide (ANP), adrenocorticotropin, corticotropin-releasing hormone, sodium nitroprusside, hydralazine, adenosine triphosphate, adenosine, indomethacin or magnesium sulfate, a phosphodiesterase inhibitor, etc.); a necrosis inhibitor (e.g., 2-(1H-Indol-3-yl)-3-pentylamino-maleimide, pyrrolidine dithiocarbamate, or clonazepam); a TNF-α inhibitor; and/or an oxygen-carrying perfluorocarbon (e.g., perfluorooctyl bromide, perfluorodecyl bromide, etc.).

The stem cell collection composition can comprise one or more tissue-degrading enzymes, e.g., a metalloprotease, a serine protease, a neutral protease, an RNase, or a DNase, or the like. Such enzymes include, but are not limited to, collagenases (e.g., collagenase I, II, III or IV, a collagenase from *Clostridium histolyticum*, etc.); dispase, thermolysin, elastase, trypsin, LIBERASE, hyaluronidase, and the like.

The stem cell collection composition can comprise a bacteriocidally or bacteriostatically effective amount of an antibiotic. In certain non-limiting embodiments, the antibiotic is a macrolide (e.g., tobramycin), a cephalosporin (e.g., cephalexin, cephradine, cefuroxime, cefprozil, cefaclor, cefixime or cefadroxil), a clarithromycin, an erythromycin, a penicillin (e.g., penicillin V) or a quinolone (e.g., ofloxacin, ciprofloxacin or norfloxacin), a tetracycline, a streptomycin, etc. In a particular embodiment, the antibiotic is active against Gram(+) and/or Gram(−) bacteria, e.g., *Pseudomonas aeruginosa, Staphylococcus aureus*, and the like.

The stem cell collection composition can also comprise one or more of the following compounds: adenosine (about 1 mM to about 50 mM); D-glucose (about 20 mM to about 100 mM); magnesium ions (about 1 mM to about 50 mM); a macromolecule of molecular weight greater than 20,000 daltons, in one embodiment, present in an amount sufficient to maintain endothelial integrity and cellular viability (e.g., a synthetic or naturally occurring colloid, a polysaccharide such as dextran or a polyethylene glycol present at about 25 g/l to about 100 g/l, or about 40 g/l to about 60 g/l); an antioxidant (e.g., butylated hydroxyanisole, butylated hydroxytoluene, glutathione, vitamin C or vitamin E present at about 25 μM to about 100 μM); a reducing agent (e.g., N-acetylcysteine present at about 0.1 mM to about 5 mM); an agent that prevents calcium entry into cells (e.g., verapamil present at about 2 μM to about 25 μM); nitroglycerin (e.g., about 0.05 g/L to about 0.2 g/L); an anticoagulant, in one embodiment, present in an amount sufficient to help prevent clotting of residual blood (e.g., heparin or hirudin present at a concentration of about 1000 units/l to about 100,000 units/l); or an amiloride containing compound (e.g., amiloride, ethyl isopropyl amiloride, hexamethylene amiloride, dimethyl amiloride or isobutyl amiloride present at about 1.0 μM to about 5 μM).

5.4.2 Collection and Handling of Placenta

Generally, a human placenta is recovered shortly after its expulsion after birth. In a preferred embodiment, the placenta is recovered from a patient after informed consent and after a complete medical history of the patient is taken and is associated with the placenta. Preferably, the medical history continues after delivery. Such a medical history can be used to coordinate subsequent use of the placenta or the stem cells harvested therefrom. For example, human placental cells can be used, in light of the medical history, for personalized medicine for the infant associated with the placenta, or for parents, siblings or other relatives of the infant.

Prior to recovery of placental stem cells, the umbilical cord blood and placental blood are removed. In certain embodiments, after delivery, the cord blood in the placenta is recovered. The placenta can be subjected to a conventional cord blood recovery process. Typically a needle or cannula is used, with the aid of gravity, to exsanguinate the placenta (see, e.g., Anderson, U.S. Pat. No. 5,372,581; Hessel et al., U.S. Pat. No. 5,415,665). The needle or cannula is usually placed in the umbilical vein and the placenta can be gently massaged to aid in draining cord blood from the placenta. Such cord blood recovery may be performed commercially, e.g., LifeBank Inc., Cedar Knolls, N.J., ViaCord, Cord Blood Registry and Cryocell. Preferably, the placenta is gravity drained without further manipulation so as to minimize tissue disruption during cord blood recovery.

Typically, a placenta is transported from the delivery or birthing room to another location, e.g., a laboratory, for recovery of cord blood and collection of stem cells by, e.g., perfusion or tissue dissociation. The placenta is preferably transported in a sterile, thermally insulated transport device (maintaining the temperature of the placenta between 20-28° C.), for example, by placing the placenta, with clamped proximal umbilical cord, in a sterile zip-lock plastic bag, which is then placed in an insulated container. In another embodiment, the placenta is transported in a cord blood collection kit substantially as described in pending U.S. patent application Ser. No. 11/230,760, filed Sep. 19, 2005. Preferably, the placenta is delivered to the laboratory four to twenty-four hours following delivery. In certain embodiments, the proximal umbilical cord is clamped, preferably within 4-5 cm (centimeter) of the insertion into the placental disc prior to cord blood recovery. In other embodiments, the proximal umbilical cord is clamped after cord blood recovery but prior to further processing of the placenta.

The placenta, prior to placental stem cell collection, can be stored under sterile conditions and at either room temperature or at a temperature of 5 to 25° C. (centigrade). The placenta may be stored for a period of longer than forty eight hours, and preferably for a period of four to twenty-four hours prior to perfusing the placenta to remove any residual cord blood. The placenta is preferably stored in an anticoagulant solution at a temperature of 5 to 25° C. (centigrade).

Suitable anticoagulant solutions are well known in the art. For example, a solution of heparin or warfarin sodium can be used. In a preferred embodiment, the anticoagulant solution comprises a solution of heparin (e.g., 1% w/w in 1:1000 solution). The exsanguinated placenta is preferably stored for no more than 36 hours before placental cells are collected.

The mammalian placenta or a part thereof, once collected and prepared generally as above, can be treated in any art-known manner, e.g., can be perfused or disrupted, e.g., digested with one or more tissue-disrupting enzymes, to obtain stem cells.

5.4.3 Physical Disruption and Enzymatic Digestion of Placental Tissue

In one embodiment, placental stem cells are collected from a mammalian placenta by physical disruption, e.g., enzymatic digestion, of the organ, e.g., using the stem cell collection composition described above. For example, the placenta, or a portion thereof, may be, e.g., crushed, sheared, minced, diced, chopped, macerated or the like, while in contact with, e.g., a buffer, medium or a stem cell collection composition, and the tissue subsequently digested with one or more enzymes. The placenta, or a portion thereof, may also be physically disrupted and digested with one or more enzymes, and the resulting material then immersed in, or mixed into, a buffer, medium or a stem cell collection composition. Any method of physical disruption can be used, provided that the method of disruption leaves a plurality, more preferably a majority, and more preferably at least 60%, 70%, 80%, 90%, 95%, 98%, or 99% of the cells in said organ viable, as determined by, e.g., trypan blue exclusion.

Typically, placental cells can be obtained by disruption of a small block of placental tissue, e.g., a block of placental tissue that is about 1, 2, 3, 4, 5, 6, 7, 8, 9, 10, 20, 30, 40, 50, 60, 70, 80, 90, 100, 200, 300, 400, 500, 600, 700, 800, 900 or about 1000 cubic millimeters in volume.

Enzymatic digestion can be performed using single enzymes or combinations of enzymes. In one embodiment, enzymatic digestion of placental tissue uses a combination of a matrix metalloprotease, a neutral protease, and a mucolytic enzyme for digestion of hyaluronic acid, such as a combination of collagenase, dispase, and hyaluronidase or a combination of LIBERASE (Boehringer Mannheim Corp., Indianapolis, Ind.) and hyaluronidase. Other enzymes that can be used to disrupt placenta tissue include papain, deoxyribonucleases, serine proteases, such as trypsin, chymotrypsin, or elastase. Serine proteases may be inhibited by alpha 2 microglobulin in serum and therefore the medium used for digestion is usually serum-free. EDTA and DNase are commonly used in enzyme digestion procedures to increase the efficiency of cell recovery. The digestate is preferably diluted so as to avoid trapping stem cells within the viscous digest.

Typical concentrations for tissue digestion enzymes include, e.g., 50-200 U/mL for collagenase I and collagenase IV, 1-10 U/mL for dispase, and 10-100 U/mL for elastase. Proteases can be used in combination, that is, two or more proteases in the same digestion reaction, or can be used sequentially in order to liberate placental cells. For example, in one embodiment, a placenta, or part thereof, is digested first with an appropriate amount of collagenase I at 2 mg/ml for 30 minutes, followed by digestion with trypsin, 0.25%, for 10 minutes, at 37° C. Serine proteases are preferably used consecutively following use of other enzymes.

In another embodiment, the tissue can further be disrupted by the addition of a chelator, e.g., ethylene glycol bis(2-aminoethyl ether)-N,N,N'N'-tetraacetic acid (EGTA) or ethylenediaminetetraacetic acid (EDTA) to the stem cell collection composition comprising the stem cells, or to a solution in which the tissue is disrupted and/or digested prior to isolation of the placental stem cells with the stem cell collection composition.

It will be appreciated that where an entire placenta, or portion of a placenta comprising both fetal and maternal cells (for example, where the portion of the placenta comprises the chorion or cotyledons) is digested to obtain placental stem cells, the placental cells collected will comprise a mix of placental cells derived from both fetal and maternal sources. Where a portion of the placenta that comprises no, or a negligible number of, maternal cells (for example, amnion) is used to obtain placental stem cells, the placental stem cells collected will comprise almost exclusively fetal placental stem cells.

5.4.4 Placental Perfusion

Placental stem cells can also be obtained by perfusion of the mammalian placenta. Methods of perfusing mammalian placenta to obtain stem cells are disclosed, e.g., in U.S. Pat. No. 7,045,148.

Placental stem cells can be collected by perfusion, e.g., through the placental vasculature, using, e.g., a stem cell collection composition as a perfusion solution. In one embodiment, a mammalian placenta is perfused by passage of perfusion solution through either or both of the umbilical artery and umbilical vein. The flow of perfusion solution through the placenta may be accomplished using, e.g., gravity flow into the placenta. Preferably, the perfusion solution is forced through the placenta using a pump, e.g., a peristaltic pump. The umbilical vein can be, e.g., cannulated with a cannula, e.g., a TEFLON® or plastic cannula, that is connected to a sterile connection apparatus, such as sterile tubing. The sterile connection apparatus is connected to a perfusion manifold.

In preparation for perfusion, the placenta is preferably oriented (e.g., suspended) in such a manner that the umbilical artery and umbilical vein are located at the highest point of the placenta. The placenta can be perfused by passage of a perfusion fluid, e.g., the stem cell collection composition provided herein, through the placental vasculature, or through the placental vasculature and surrounding tissue. In one embodiment, the umbilical artery and the umbilical vein are connected simultaneously to a pipette that is connected via a flexible connector to a reservoir of the perfusion solution. The perfusion solution is passed into the umbilical vein and artery. The perfusion solution exudes from and/or passes through the walls of the blood vessels into the surrounding tissues of the placenta, and is collected in a suitable open vessel from the surface of the placenta that was attached to the uterus of the mother during gestation. The perfusion solution may also be introduced through the umbilical cord opening and allowed to flow or percolate out of openings in the wall of the placenta which interfaced with the maternal uterine wall. In another embodiment, the perfusion solution is passed through the umbilical veins and collected from the umbilical artery, or is passed through the umbilical artery and collected from the umbilical veins.

In one embodiment, the proximal umbilical cord is clamped during perfusion, and more preferably, is clamped within 4-5 cm (centimeter) of the cord's insertion into the placental disc.

The first collection of perfusion fluid from a mammalian placenta during the exsanguination process is generally colored with residual red blood cells of the cord blood and/or placental blood; this portion of the perfusion can be discarded. The perfusion fluid becomes more colorless as perfusion proceeds and the residual cord blood cells are washed out of the placenta.

The volume of perfusion liquid used to collect placental stem cells may vary depending upon the number of placental stem cells to be collected, the size of the placenta, the number of collections to be made from a single placenta, etc. In various embodiments, the volume of perfusion liquid may be from 50 mL to 5000 mL, 50 mL to 4000 mL, 50 mL to 3000 mL, 100 mL to 2000 mL, 250 mL to 2000 mL, 500 mL to 2000 mL, or 750 mL to 2000 mL. Typically, the placenta is perfused with 700-800 mL of perfusion liquid following exsanguination.

The placenta can be perfused a plurality of times over the course of several hours or several days. Where the placenta is to be perfused a plurality of times, it may be maintained or cultured under aseptic conditions in a container or other suitable vessel, and perfused with the stem cell collection composition, or a standard perfusion solution (e.g., a normal saline solution such as phosphate buffered saline ("PBS")) with or without an anticoagulant (e.g., heparin, warfarin sodium, coumarin, bishydroxycoumarin), and/or with or without an antimicrobial agent (e.g., β-mercaptoethanol (0.1 mM); antibiotics such as streptomycin (e.g., at 40-100 µg/ml), penicillin (e.g., at 40 U/ml), amphotericin B (e.g., at 0.5 µg/ml). In one embodiment, an isolated placenta is maintained or cultured for a period of time without collecting the perfusate, such that the placenta is maintained or cultured for 1, 2, 3, 4, 5, 6, 7, 8, 9, 10, 11, 12, 13, 14, 15, 16, 17, 18, 19, 20, 21, 22, 23, or 24 hours, or 2 or 3 or more days before perfusion and collection of perfusate. The perfused placenta can be maintained for one or more additional time(s), e.g., 1, 2, 3, 4, 5, 6, 7, 8, 9, 10, 11, 12, 13, 14, 15, 16, 17, 18, 19, 20, 21, 22, 23, 24 or more hours, and perfused a second time with, e.g., 700-800 mL perfusion fluid. The placenta can be perfused 1, 2, 3, 4, 5 or more times, for example, once every 1, 2, 3, 4, 5 or 6 hours. In a preferred embodiment, perfusion of the placenta and collection of perfusion solution, e.g., stem cell collection composition, is repeated until the number of recovered nucleated cells falls below 100 cells/ml. The perfusates at different time points can be further processed individually to recover time-dependent populations of placental stem cells. Perfusates from different time points can also be pooled.

Without wishing to be bound by any theory, after exsanguination and a sufficient time of perfusion of the placenta, placental stem cells are believed to migrate into the exsanguinated and perfused microcirculation of the placenta where they are collectable, preferably by washing into a collecting vessel by perfusion. Perfusing the isolated placenta not only serves to remove residual cord blood but also provide the placenta with the appropriate nutrients, including oxygen. The placenta may be cultivated and perfused with a similar solution which was used to remove the residual cord blood cells, preferably, without the addition of anticoagulant agents.

Stem cells can be isolated from placenta by perfusion with a solution comprising one or more proteases or other tissue-disruptive enzymes. In a specific embodiment, a placenta or portion thereof is brought to 25-37° C., and is incubated with one or more tissue-disruptive enzymes in 200 mL of a culture medium for 30 minutes. Cells from the perfusate are collected, brought to 4° C., and washed with a cold inhibitor mix comprising 5 mM EDTA, 2 mM dithiothreitol and 2 mM beta-mercaptoethanol. The placental stem cells are washed after several minutes with a cold (e.g., 4° C.) stem cell collection composition described elsewhere herein.

Perfusion using the pan method, that is, whereby perfusate is collected after it has exuded from the maternal side of the placenta, results in a mix of fetal and maternal cells. As a result, the cells collected by this method comprise a mixed population of placental stem cells of both fetal and maternal origin. In contrast, perfusion solely through the placental vasculature, whereby perfusion fluid is passed through one or two placental vessels and is collected solely through the remaining vessel(s), results in the collection of a population of placental stem cells almost exclusively of fetal origin.

5.4.5 Isolation, Sorting, and Characterization of Placental Cells

Stem cells from mammalian placenta, whether obtained by perfusion or enyzmatic digestion, can initially be purified from (i.e., be isolated from) other cells by Ficoll gradient centrifugation. Such centrifugation can follow any standard protocol for centrifugation speed, etc. In one embodiment, for example, cells collected from the placenta are recovered from perfusate by centrifugation at 5000×g for 15 minutes at room temperature, which separates cells from, e.g., contaminating debris and platelets. In another embodiment, placental perfusate is concentrated to about 200 ml, gently layered over Ficoll, and centrifuged at about 1100×g for 20 minutes at 22° C., and the low-density interface layer of cells is collected for further processing.

Cell pellets can be resuspended in fresh stem cell collection composition, or a medium suitable for stem cell maintenance, e.g., IMDM serum-free medium containing 2 U/ml heparin and 2 mM EDTA (GibcoBRL, NY). The total mononuclear cell fraction can be isolated, e.g., using Lymphoprep (Nycomed Pharma, Oslo, Norway) according to the manufacturer's recommended procedure.

As used herein, "isolating" placental stem cells means removing at least 20%, 30%, 40%, 50%, 60%, 70%, 80%, 90%, 95% or 99% of the cells with which the placental stem cells are normally associated in the intact mammalian placenta.

Placental stem cells obtained by perfusion or digestion can, for example, be further, or initially, isolated by differential trypsinization using, e.g., a solution of 0.05% trypsin with 0.2% EDTA (Sigma, St. Louis Mo.). Differential trypsinization is possible because placental stem cells typically detach from plastic surfaces within about five minutes whereas other adherent populations typically require more than 20-30 minutes incubation. The detached placental stem cells can be harvested following trypsinization and trypsin neutralization, using, e.g., Trypsin Neutralizing Solution (TNS, Cambrex).

In one embodiment of isolation of placental stem cells, aliquots of, for example, about 5-10×10$^6$ placental cells are placed in each of several T-75 flasks, preferably fibronectin-coated T75 flasks. In such an embodiment, the cells can be cultured with commercially available Mesenchymal Stem Cell Growth Medium (MSCGM) (Cambrex), and placed in a tissue culture incubator (37° C., 5% CO$_2$). After 10 to 15 days, non-adherent cells are removed from the flasks by washing with PBS. The PBS is then replaced by MSCGM. Flasks are preferably examined daily for the presence of various adherent cell types and in particular, for identification and expansion of clusters of fibroblastoid cells.

The number and type of cells collected from a mammalian placenta can be monitored, for example, by measuring changes in morphology and cell surface markers using standard cell detection techniques such as flow cytometry, cell sorting, immunocytochemistry (e.g., staining with tissue specific or cell-marker specific antibodies) fluorescence activated cell sorting (FACS), magnetic activated cell sorting (MACS), by examination of the morphology of cells using light or confocal microscopy, and/or by measuring changes in gene expression using techniques well known in the art, such as PCR and gene expression profiling. These techniques can be used, too, to identify cells that are positive for one or more particular markers. For example, using antibodies to CD34, one can determine, using the techniques above, whether a cell comprises a detectable amount of CD34 as compared to, for example, an isotype control; if so, the cell is CD34$^+$. Likewise, if a cell produces enough OCT-4 RNA to be detectable by RT-PCR, or significantly more OCT-4 RNA than a terminally-differentiated cell, the cell is OCT-4$^+$. Antibodies to cell surface markers (e.g., CD markers such as CD34) and the sequence of stem cell-specific genes, such as OCT-4, are well-known in the art.

Placental cells, particularly cells that have been isolated by Ficoll separation, differential adherence, or a combination of both, may be sorted, e.g., further isolated, using a fluorescence activated cell sorter (FACS). Fluorescence activated cell sorting (FACS) is a well-known method for separating particles, including cells, based on the fluorescent properties of the particles (Kamarch, 1987, Methods Enzymol, 151:150-165). Laser excitation of fluorescent moieties in the individual particles results in a small electrical charge allowing electromagnetic separation of positive and negative particles from a mixture. In one embodiment, cell surface marker-specific antibodies or ligands are labeled with distinct fluorescent labels. Cells are processed through the cell sorter, allowing separation of cells based on their ability to bind to the antibodies used. FACS sorted particles may be directly deposited into individual wells of 96-well or 384-well plates to facilitate separation and cloning.

In one sorting scheme, placental stem cells can be sorted on the basis of expression of the markers CD34, CD38, CD44, CD45, CD73, CD105, OCT-4 and/or HLA-G, or any of the other markers listed elsewhere herein. This can be accomplished in connection with procedures to select stem cells on the basis of their adherence properties in culture. For example, adherence selection of placental stem cells can be accomplished before or after sorting on the basis of marker expression. In one embodiment, for example, placental stem cells can be sorted first on the basis of their expression of CD34; CD34$^-$ cells are retained, and cells that are CD200$^+$ or HLA-G$^-$, are separated from all other CD34$^-$ cells. In another embodiment, placental stem cells can be sorted based on their expression of CD200 and/or HLA-G, or lack thereof; for example, cells displaying either of these markers can be isolated for further use. Cells that express, e.g., CD200 and/or HLA-G can, in a specific embodiment, be further sorted based on their expression of CD73 and/or CD105, or epitopes recognized by antibodies SH2, SH3 or SH4, or lack of expression of CD34, CD38 or CD45. For example, in one embodiment, placental stem cells are sorted by expression, or lack thereof, of CD200, HLA-G, CD73, CD105, CD34, CD38 and CD45, and placental stem cells that are CD200$^+$, HLA-G$^-$, CD73$^+$, CD105$^+$, CD34$^-$, CD38$^-$ and CD45$^-$ are isolated from other placental cells for further use.

In another embodiment, magnetic beads can be used to separate cells, e.g., separate placental stem cells from other placental cells. The cells may be sorted using a magnetic activated cell sorting (MACS) technique, a method for separating particles based on their ability to bind magnetic beads (0.5-100 µm diameter). A variety of useful modifications can be performed on the magnetic microspheres, including covalent addition of antibody that specifically recognizes a particular cell surface molecule or hapten. The beads are then mixed with the cells to allow binding. Cells are then passed through a magnetic field to separate out cells having the specific cell surface marker. In one embodiment, these cells can then isolated and re-mixed with magnetic beads coupled to an antibody against additional cell surface markers. The cells are again passed through a magnetic field, isolating cells that bound both the antibodies. Such cells can then be diluted into separate dishes, such as microtiter dishes for clonal isolation.

Placental stem cells can also be characterized and/or sorted based on cell morphology and growth characteristics. For example, placental stem cells can be characterized as having, and/or selected on the basis of, e.g., a fibroblastoid appearance in culture. Placental stem cells can also be characterized as having, and/or be selected, on the basis of their ability to form embryoid-like bodies. In one embodiment, for example, placental cells that are fibroblastoid in shape, express CD73 and CD105, and produce one or more embryoid-like bodies in culture can be isolated from other placental cells. In another embodiment, OCT-4$^+$ placental cells that produce one or more embryoid-like bodies in culture are isolated from other placental cells.

In another embodiment, placental stem cells can be identified and characterized by a colony forming unit assay. Colony forming unit assays are commonly known in the art, such as Mesen Cult™ medium (Stem Cell Technologies, Inc., Vancouver British Columbia).

Placental stem cells can be assessed for viability, proliferation potential, and longevity using standard techniques known in the art, such as trypan blue exclusion assay, fluorescein diacetate uptake assay, propidium iodide uptake assay (to assess viability); and thymidine uptake assay, MTT cell proliferation assay (to assess proliferation). Longevity may be determined by methods well known in the art, such as by determining the maximum number of population doubling in an extended culture.

Placental stem cells can also be separated from other placental cells using other techniques known in the art, e.g., selective growth of desired cells (positive selection), selective destruction of unwanted cells (negative selection); separation based upon differential cell agglutinability in the mixed population as, for example, with soybean agglutinin; freeze-thaw procedures; filtration; conventional and zonal centrifugation; centrifugal elutriation (counter-streaming centrifugation); unit gravity separation; countercurrent distribution; electrophoresis; and the like.

5.5 Culture of Placental Stem Cells
5.5.1 Culture Media

Placental stem cells, including the enhanced placental stem cells described herein, can be cultured in any medium, and under any conditions, recognized in the art as acceptable for the culture of stem cells. In certain embodiments, the culture medium comprises serum. In certain embodiments, placental stem cells, including the enhanced placental stem cells described herein, can be cultured in, for example, DMEM-LG (Dulbecco's Modified Essential Medium, low glucose)/MCDB 201 (chick fibroblast basal medium) containing ITS (insulin-transferrin-selenium), LA+BSA (linoleic acid-bovine serum albumin), dextrose, L-ascorbic acid, PDGF, EGF, IGF-1, and penicillin/streptomycin; DMEM-HG (high glucose) comprising 10% fetal bovine serum (FBS); DMEM-HG comprising 15% FBS; IMDM (Iscove's modified Dulbecco's medium) comprising 10% FBS, 10% horse serum, and hydrocortisone; M199 comprising 10% FBS, EGF, and heparin; α-MEM (minimal essential medium) comprising 10% FBS, GlutaMAX™ and gentamicin; DMEM comprising 10% FBS, GlutaMAX™ and gentamicin, etc. A preferred medium is DMEM-LG/MCDB-201 comprising 2% FBS, ITS, LA+BSA, dextrose, L-ascorbic acid, PDGF, EGF, and penicillin/streptomycin.

Other media in that can be used to culture placental stem cells, including the enhanced placental stem cells described herein, include DMEM (high or low glucose), Eagle's basal medium, Ham's F10 medium (F10), Ham's F-12 medium (F12), Iscove's modified Dulbecco's medium, Mesenchymal Stem Cell Growth Medium (MSCGM), Liebovitz's L-15 medium, MCDB, DMIEM/F12, RPMI 1640, advanced DMEM (Gibco), DMEM/MCDB201 (Sigma), and CELL-GRO FREE.

The culture medium can be supplemented with one or more components including, for example, serum (e.g., fetal bovine serum (FBS), preferably about 2-15% (v/v); equine (horse) serum (ES); human serum (HS)); beta-mercaptoethanol (BME), preferably about 0.001% (v/v); one or more growth factors, for example, platelet-derived growth factor (PDGF), epidermal growth factor (EGF), basic fibroblast growth factor (bFGF), insulin-like growth factor-1 (IGF-1), leukemia inhibitory factor (LIF), vascular endothelial growth factor (VEGF), and erythropoietin (EPO); amino acids, including L-valine; and one or more antibiotic and/or antimycotic agents to control microbial contamination, such as, for example, penicillin G, streptomycin sulfate, amphotericin B, gentamicin, and nystatin, either alone or in combination.

5.5.2 Expansion and Proliferation of Placental Stem Cells

Once placental stem cells, including the enhanced placental stem cells described herein, are isolated, the stem cells or population of stem cells can be proliferated and expanded in vitro. For example, once enhanced placental stem cells are produced, such cells can also be proliferated and expanded in vitro. Placental stem cells, including the enhanced placental stem cells described herein, can be cultured in tissue culture containers, e.g., dishes, flasks, multiwell plates, or the like, for a sufficient time for the placental stem cells to proliferate to 70-90% confluence, that is, until the placental stem cells and their progeny occupy 70-90% of the culturing surface area of the tissue culture container.

Placental stem cells, including the enhanced placental stem cells described herein, can be seeded in culture vessels at a density that allows cell growth. For example, the placental stem cells may be seeded at low density (e.g., about 1,000 to about 5,000 cells/cm$^2$) to high density (e.g., about 50,000 or more cells/cm$^2$). In a preferred embodiment, the placental stem cells are cultured at about 0 to about 5 percent by volume $CO_2$ in air. In some preferred embodiments, the placental stem cells are cultured at about 2 to about 25 percent $O_2$ in air, preferably about 5 to about 20 percent $O_2$ in air. The placental stem cells preferably are cultured at about 25° C. to about 40° C., preferably 37° C. The placental stem cells are preferably cultured in an incubator. The culture medium can be static or agitated, for example, using a bioreactor. Placental stem cells can be grown under low oxidative stress (e.g., with addition of glutathione, ascorbic acid, catalase, tocopherol, N-acetylcysteine, or the like).

Once 70%-90% confluence is obtained, the placental stem cells, including the enhanced placental stem cells described herein, may be passaged. For example, the cells can be enzymatically treated, e.g., trypsinized, using techniques well-known in the art, to separate them from the tissue culture surface. After removing the placental stem cells by pipetting and counting the cells, about 20,000-100,000 stem cells, preferably about 50,000 placental stem cells, are passaged to a new culture container containing fresh culture medium. Typically, the new medium is the same type of medium from which the stem cells were removed. Provided herein are populations of placental stem cells, including the enhanced placental stem cells described herein, that have been passaged at least 1, 2, 3, 4, 5, 6, 7, 8, 9, 10, 12, 14, 16, 18, or 20 times, or more, and combinations of the same.

5.6 Preservation of Enhanced Placental Cells

Enhanced placental stem cells can be preserved, that is, placed under conditions that allow for long-term storage, or conditions that inhibit cell death by, e.g., apoptosis or necrosis.

Enhanced placental stem cells can be preserved using, e.g., a composition comprising an apoptosis inhibitor, necrosis inhibitor and/or an oxygen-carrying perfluorocarbon, as described in related U.S. Patent Application Publication No. 2007/0190042.

In one embodiment, provided herein is a method of preserving enhanced placental stem cells comprising contacting said enhanced placental stem cells with a stem cell collection composition comprising an inhibitor of apoptosis and an oxygen-carrying perfluorocarbon, wherein said inhibitor of apoptosis is present in an amount and for a time sufficient to reduce or prevent apoptosis in the population of enhanced placental stem cells, as compared to a population of enhanced placental stem cells not contacted with the inhibitor of apoptosis. In a specific embodiment, said inhibitor of apoptosis is a caspase inhibitor. In another specific embodiment, said inhibitor of apoptosis is a JNK inhibitor. In a more specific embodiment, said JNK inhibitor does not modulate differentiation or proliferation of said enhanced placental stem cells. In another embodiment, said stem cell collection composition comprises said inhibitor of apoptosis and said oxygen-carrying perfluorocarbon in separate phases. In another embodiment, said stem cell collection composition comprises said inhibitor of apoptosis and said oxygen-carrying perfluorocarbon in an emulsion. In another embodiment, the stem cell collection composition additionally comprises an emulsifier, e.g., lecithin. In another embodiment, said apoptosis inhibitor and said perfluorocarbon are between about 0° C. and about 25° C. at the time of contacting the stem cells. In another more specific embodiment, said apoptosis inhibitor and said perfluorocarbon are between about 2° C. and 10° C., or between about 2° C. and about 5° C., at the time of contacting the stem cells. In another more specific embodiment, said contacting is performed during transport of said enhanced placental stem cells. In another more specific embodiment, said contacting is performed during freezing and thawing of said population of enhanced placental stem cells.

In another embodiment, enhanced placental stem cells can be preserved by a method comprising contacting said enhanced placental stem cells with an inhibitor of apoptosis and an organ-preserving compound, wherein said inhibitor of apoptosis is present in an amount and for a time sufficient to reduce or prevent apoptosis of the enhanced placental stem cells, as compared to enhanced placental stem cells not contacted with the inhibitor of apoptosis. In a specific embodiment, the organ-preserving compound is UW solution (described in U.S. Pat. No. 4,798,824; also known as ViaSpan; see also Southard et al., *Transplantation* 49(2): 251-257 (1990)) or a solution described in Stern et al., U.S. Pat. No. 5,552,267. In another embodiment, said organ-preserving compound is hydroxyethyl starch, lactobionic acid, raffinose, or a combination thereof.

In another embodiment, placental stem cells, to be used to produce enhanced placental stem cells, are contacted with a stem cell collection composition comprising an apoptosis inhibitor and oxygen-carrying perfluorocarbon, organ-preserving compound, or combination thereof, during perfusion. In another embodiment, said placental stem cells, to be used to produce enhanced placental stem cells, are contacted during a process of tissue disruption, e.g., enzymatic digestion. In another embodiment, placental cells, to be used to produce enhanced placental stem cells, are contacted with said stem cell collection compound after collection by perfusion, or after collection by tissue disruption, e.g., enzymatic digestion.

Typically, during placental stem cell collection, enrichment and isolation, it is preferable to minimize or eliminate cell stress due to hypoxia and mechanical stress. In another embodiment of the method, therefore, placental stem cells, to be used to produce enhanced placental stem cells, are exposed to a hypoxic condition during collection, enrichment or isolation for less than six hours during said preservation, wherein a hypoxic condition is a concentration of oxygen that is less than normal blood oxygen concentration. In a more specific embodiment, said placental stem cells are exposed to said hypoxic condition for less than two hours during said preservation. In another more specific embodiment, said placental stem cells are exposed to said hypoxic condition for less than one hour, or less than thirty minutes, or is not exposed to a hypoxic condition, during collection, enrichment or isolation. In another specific embodiment, said placental stem cells are not exposed to shear stress during collection, enrichment or isolation.

The enhanced placental stem cells, as well as the placental stem cells to be used to produce enhanced placental stem cells, described herein can be cryopreserved, e.g., in cryopreservation medium in small containers, e.g., ampoules. Suitable cryopreservation medium includes, but is not limited to, culture medium including, e.g., growth medium, or cell freezing medium, for example commercially available cell freezing medium, e.g., C2695, C2639 or C6039 (Sigma). Cryopreservation medium preferably comprises DMSO (dimethylsulfoxide), at a concentration of, e.g., about 10% (v/v). Cryopreservation medium may comprise additional agents, for example, Plasmalyte, methylcellulose with or without glycerol. The stem cells are preferably cooled at about 1° C./min during cryopreservation. A preferred cryopreservation temperature is about −80° C. to about −180° C., preferably about −125° C. to about −140° C. Cryopreserved cells can be transferred to liquid nitrogen prior to thawing for use. In some embodiments, for example, once the ampoules have reached about −90° C., they are transferred to a liquid nitrogen storage area. Cryopreserved cells preferably are thawed at a temperature of about 25° C. to about 40° C., preferably to a temperature of about 37° C. In certain embodiments, enhanced placental stem cells provided herein are cryopreserved about 12, 24, 36, 48, 60 or 72 hours after being contacted with modulatory RNA molecules (e.g., transfection). In one embodiment, enhanced placental stem cells provided herein are cryopreserved about 24 hours after being contacted with modulatory RNA molecules (e.g., transfection).

5.7 Compositions 5.7.1 Compositions Comprising Enhanced Placental Stem Cells

Provided herein are compositions comprising the enhanced placental stem cells described herein. Such compositions may comprise populations of enhanced placental stem cells provided herein combined with any physiologically-acceptable or medically-acceptable compound, composition or device for use in, e.g., research or therapeutics.

Enhanced placental stem cells can be prepared in a form that is easily administrable to an individual. For example, enhanced placental stem cells described herein can be contained within a container that is suitable for medical use. Such a container can be, for example, a sterile plastic bag, flask, jar, vial, or other container from which the placental cell population can be easily dispensed. For example, the container can be a blood bag or other plastic, medically-acceptable bag suitable for the intravenous administration of a liquid to a recipient. The container is preferably one that allows for cryopreservation of the enhanced placental stem cells.

Enhanced placental stem cell populations, e.g., cryopreserved enhanced placental stem cell populations, can comprise enhanced placental stem cells derived from a single donor, or from multiple donors. The enhanced placental stem cells can be completely HLA-matched to an intended recipient, or partially or completely HLA-mismatched.

Thus, in one embodiment, provided herein is a composition comprising enhanced placental stem cells in a container. In a specific embodiment, the enhanced placental stem cells cryopreserved. In another specific embodiment, the container is a bag, flask, vial or jar. In more specific embodiment, said bag is a sterile plastic bag. In a more specific embodiment, said bag is suitable for, allows or facilitates intravenous administration of said enhanced placental stem cells. The bag can comprise multiple lumens or compartments that are interconnected to allow mixing of the enhanced placental stem cells and one or more other solutions, e.g., a drug, prior to, or during, administration. In another specific embodiment, the composition comprises one or more compounds that facilitate cryopreservation of the combined stem cell population. In another specific embodiment, said enhanced placental stem cells are contained within a physiologically-acceptable aqueous solution. In a more specific embodiment, said physiologically-acceptable aqueous solution is a 0.9% NaCl solution. In another specific embodiment, said enhanced placental stem cells are HLA-matched to a recipient of said enhanced placental stem cells. In another specific embodiment, said enhanced placental stem cells are at least partially HLA-mismatched to a recipient of said enhanced placental stem cells. In another specific embodiment, said enhanced placental stem cells are derived from placental stem cells from a plurality of donors.

5.7.1.1 Pharmaceutical Compositions

In another aspect, provided herein is a pharmaceutical composition, said pharmaceutical composition comprising a therapeutically effective amount of enhanced placental stem cells.

The enhanced placental stem cells provided herein can be formulated into pharmaceutical compositions for use in vivo. Such pharmaceutical compositions can comprise enhanced placental stem cells in a pharmaceutically-acceptable carrier, e.g., a saline solution or other accepted physiologically-acceptable solution for in vivo administration. Pharmaceutical compositions provided herein can comprise any of the enhanced placental stem cells described herein. The pharmaceutical compositions can comprise fetal, maternal, or both fetal and maternal enhanced placental stem cells. The pharmaceutical compositions provided herein can further comprise enhanced placental stem cells produced from placental stem cells obtained from a single individual or placenta, or from a plurality of individuals or placentae.

The pharmaceutical compositions provided herein can comprise any number of enhanced placental stem cells. For example, a single unit dose of enhanced placental stem cells can comprise, in various embodiments, about, at least, or no more than $1\times10^5$, $5\times10^5$, $1\times10^6$, $5\times10^6$, $1\times10^7$, $5\times10^7$, $1\times10^8$, $5\times10^8$, $1\times10^9$, $5\times10^9$, $1\times10^{10}$, $5\times10^{10}$, $1\times10^{11}$ or more enhanced placental stem cells.

The pharmaceutical compositions provided herein can comprise populations of enhanced placental stem cells that comprise 50% viable enhanced placental stem cells or more (that is, at least 50% of the cells in the population are functional or living). Preferably, at least 60% of the cells in the population are viable. More preferably, at least 70%, 80%, 90%, 95%, or 99% of the enhanced placental stem cells in the population in the pharmaceutical composition are viable.

5.7.1.2 Matrices Comprising Enhanced Placental Stem Cells

Further provided herein are matrices, hydrogels, scaffolds, and the like that comprise enhanced placental stem cells. The enhanced placental stem cells provided herein can be seeded onto a natural matrix, e.g., a placental biomaterial such as an amniotic membrane material. Such an amniotic membrane material can be, e.g., amniotic membrane dissected directly from a mammalian placenta; fixed or heat-treated amniotic membrane, substantially dry (i.e., <20%, <15%, <10%, <5%, <2%, or <1% $H_2O$) amniotic membrane, chorionic membrane, substantially dry chorionic membrane, substantially dry amniotic and chorionic membrane, and the like. Preferred placental biomaterials on which enhanced placental stem cells can be seeded are described in U.S. Application Publication No. 2004/0048796.

The enhanced placental stem cells provided herein can be suspended in a hydrogel solution suitable for, e.g., injection. Suitable hydrogels for such compositions include self-assembling peptides, such as RAD16. Enhanced placental stem cells can also be combined with, e.g., alginate or platelet-rich plasma, or other fibrin-containing matrices, for local injection. In one embodiment, a hydrogel solution comprising enhanced placental stem cells can be allowed to harden, for instance in a mold, to form a matrix having the cells dispersed therein for implantation. Enhanced placental stem cells in such a matrix can also be cultured so that the cells are mitotically expanded prior to implantation. The hydrogel can be, e.g., an organic polymer (natural or synthetic) that is cross-linked via covalent, ionic, or hydrogen bonds to create a three-dimensional open-lattice structure that entraps water molecules to form a gel. Hydrogel-forming materials include polysaccharides such as alginate and salts thereof, peptides, polyphosphazines, and polyacrylates, which are crosslinked ionically, or block polymers such as polyethylene oxide-polypropylene glycol block copolymers which are crosslinked by temperature or pH, respectively. In some embodiments, the hydrogel or matrix is biodegradable.

In some embodiments, the matrix comprises an in situ polymerizable gel (see., e.g., U.S. Patent Application Publication 2002/0022676; Anseth et al., *J. Control Release*, 78(1-3):199-209 (2002); Wang et al., *Biomaterials*, 24(22): 3969-80 (2003).

In some embodiments, the polymers are at least partially soluble in aqueous solutions, such as water, buffered salt solutions, or aqueous alcohol solutions, that have charged side groups, or a monovalent ionic salt thereof. Examples of polymers having acidic side groups that can be reacted with cations are poly(phosphazenes), poly(acrylic acids), poly (methacrylic acids), copolymers of acrylic acid and methacrylic acid, poly(vinyl acetate), and sulfonated polymers, such as sulfonated polystyrene. Copolymers having acidic side groups formed by reaction of acrylic or methacrylic acid and vinyl ether monomers or polymers can also be used. Examples of acidic groups are carboxylic acid groups, sulfonic acid groups, halogenated (preferably fluorinated) alcohol groups, phenolic OH groups, and acidic OH groups.

The enhanced placental stem cells can be seeded onto a three-dimensional framework or scaffold and implanted in vivo. Such a framework can be implanted in combination with any one or more growth factors, cells, drugs or other components that stimulate tissue formation or otherwise enhance or improve the practice of the methods of treatment described elsewhere herein.

Examples of scaffolds that can be used herein include nonwoven mats, porous foams, or self assembling peptides. Nonwoven mats can be formed using fibers comprised of a synthetic absorbable copolymer of glycolic and lactic acids (e.g., PGA/PLA) (VICRYL, Ethicon, Inc., Somerville, N.J.). Foams, composed of, e.g., poly(ε-caprolactone)/poly(glycolic acid) (PCL/PGA) copolymer, formed by processes such as freeze-drying, or lyophilization (see, e.g., U.S. Pat. No. 6,355,699), can also be used as scaffolds.

In another embodiment, the scaffold is, or comprises, a nanofibrous scaffold, e.g., an electrospun nanofibrous scaffold. In a more specific embodiment, said nanofibrous scaffold comprises poly(L-lactic acid) (PLLA), type I collagen, a copolymer of vinylidene fluoride and trifluoroethylnee (PVDF-TrFE), poly(-caprolactone), poly(L-lactide-co-ε-caprolactone) [P(LLA-CL)] (e.g., 75:25), and/or a copolymer of poly(3-hydroxybutyrate-co-3-hydroxyvalerate) (PHBV) and type I collagen. Methods of producing nanofibrous scaffolds, e.g., electrospun nanofibrous scaffolds, are known in the art. See, e.g., Xu et al., *Tissue Engineering* 10(7):1160-1168 (2004); Xu et al., *Biomaterials* 25:877-886 (20040; Meng et al., *J. Biomaterials Sci., Polymer Edition* 18(1):81-94 (2007).

The enhanced placental stem cells described herein can also be seeded onto, or contacted with, a physiologically-acceptable ceramic material including, but not limited to, mono-, di-, tri-, alpha-tri-, beta-tri-, and tetra-calcium phosphate, hydroxyapatite, fluoroapatites, calcium sulfates, calcium fluorides, calcium oxides, calcium carbonates, magnesium calcium phosphates, biologically active glasses such as BIOGLASS®, and mixtures thereof. Porous biocompatible ceramic materials currently commercially available include SURGIBONE® (CanMedica Corp., Canada), ENDOBON® (Merck Biomaterial France, France), CEROS® (Mathys, AG, Bettlach, Switzerland), and mineralized collagen bone grafting products such as HEALOS™ (DePuy, Inc., Raynham, Mass.) and VITOSS®, RHAKOSS™, and COR-TOSS® (Orthovita, Malvern, Pa.). The framework can be a mixture, blend or composite of natural and/or synthetic materials.

In another embodiment, enhanced placental stem cells can be seeded onto, or contacted with, a felt, which can be, e.g., composed of a multifilament yarn made from a bioabsorbable material such as PGA, PLA, PCL copolymers or blends, or hyaluronic acid.

The enhanced placental stem cells described herein can, in another embodiment, be seeded onto foam scaffolds that may be composite structures. Such foam scaffolds can be molded into a useful shape. In some embodiments, the framework is treated, e.g., with 0.1M acetic acid followed by incubation in polylysine, PBS, and/or collagen, prior to inoculation of the enhanced placental stem cells in order to enhance cell attachment. External surfaces of a matrix may be modified to improve the attachment or growth of cells and differentiation of tissue, such as by plasma-coating the matrix, or addition of one or more proteins (e.g., collagens, elastic fibers, reticular fibers), glycoproteins, glycosaminoglycans (e.g., heparin sulfate, chondroitin-4-sulfate, chondroitin-6-sulfate, dermatan sulfate, keratin sulfate, etc.), a cellular matrix, and/or other materials such as, but not limited to, gelatin, alginates, agar, agarose, and plant gums, and the like.

In some embodiments, the scaffold comprises, or is treated with, materials that render it non-thrombogenic. These treatments and materials may also promote and sustain endothelial growth, migration, and extracellular matrix deposition. Examples of these materials and treatments include but are not limited to natural materials such as basement membrane proteins such as laminin and Type IV collagen, synthetic materials such as EPTFE, and segmented polyurethaneurea silicones, such as PURSPAN™ (The Polymer Technology Group, Inc., Berkeley, Calif.). The scaffold can also comprise anti-thrombotic agents such as heparin; the scaffolds can also be treated to alter the surface charge (e.g., coating with plasma) prior to seeding with enhanced placental stem cells.

6. EXAMPLES

6.1 Example 1: Identification of Survival-Associated Genes Associated with Placental Stem Cell Survival This example describes the identification of molecular pathways and specific genes associated with the response of placental stem cells to environmental insult. Increases of cellular caspase 3/7 activity as well as decreases in cellular metabolic activity and mitochondrial membrane potential are known to be associated with decrease in cellular survival. Accordingly, augmentation of survival was assessed by measurement of caspase 3/7 activity, metabolic activity, and mitochondrial membrane potential of placental stem cells following insult.

6.1.1 Methods

6.1.1.1 MicroRNA Library Screen

A microRNA library screen was used to identify microRNA capable of augmenting the survival of placental stem cells exposed to environmental insult. Placental stem cells were seeded on tissue culture plates for 24 hours, transfected with a microRNA library for 24 hours, then insulted with 100% normal rat serum overnight. Following the overnight culture in insult (100% rat serum), the cells were assayed for cell survival augmentation. The protocol is described in greater detail below.

6.1.1.1.1 MicroRNA Transfection $CD34^-$, $CD10^+$, $CD105^+$, $CD200^+$ Placental stem cells were seeded in 96-well tissue culture plates, in duplicate, at a concentration of $3\times10^3$ ("Day 0"). After 24 h, on Day 1, the cells were transfected with 100 nM of the Ambion Pre-miR Mimic Library (miRBase v15), appropriate controls (no treatment; vehicle; and negative controls 1 and 2, obtained from the manufacturer), and Ambion's Amine transfection reagent.

6.1.1.1.2 Environmental Insult

On Day 2, the transfection media was removed and replaced with either culture medium or 100% Normal Rat Serum (insult) (Invitrogen) and incubated overnight.

6.1.1.1.3 Insult/Capase 3/7 Assessment

On Day 3 the insult media was removed, replaced with 100 μL of 0.5 μM Hoechst 33342 stain, and the cells were incubated for 1 hour at 37° C. The stained cells were then imaged using an InCell Analyzer (GE) and nuclei counts were analyzed. After imaging, the Hoechst stain was removed and the cells were incubated with 100 μL of Caspase-Glo 3/7 (Promega) reagent for 1 hour at room temperature. Following incubation, absolute luminescence was read using a Biotek Synergy Plate Reader, and Luminescence readouts and nuclei counts were used to calculate caspase 3/7 activity/cell. Hits were analyzed against both negative controls and microRNAs that significantly lowered caspase 3/7 activity in the placental stem cells vs. either Negative Control ($p<0.05$, Student's t-Test) were identified.

6.1.1.2 Metabolic Activity and Mitochondrial Membrane Potential Studies

In addition to the microRNA library screen, metabolic activity and mitochondrial membrane potential of placental stem cells exposed to environmental insult was assessed using the Cell Titer Glo Assay (Promega) and the TMRE Mitochondrial Membrane Potential Assay Kit (Abcam), respectively.

For the assessment of metabolic activity, placental stem cells exposed to insult (rat serum) as described above were incubated with 100 μL of Cell Titer Glo (Promega) reagent for 15 minutes at room temperature. Following incubation, absolute luminescence was read using a Biotek Synergy Plate Reader, and luminescence readouts and nuclei counts were used to calculate metabolic activity/cell.

For the assessment of mitochondrial membrane potential, placental stem cells exposed to insult (rat serum) as described above were incubated with 1.5 μM of TMRE stain (Abcam) reagent for 30 minutes at 37° C. Following incubation, cells were washed twice with 0.2% BSA-PBS, and fluorescence was read using a Biotek Synergy Plate Reader. The mean fluorescence intensity readouts and nuclei counts were used to calculate mitochondrial membrane potential/cell.

For both assays, hits were analyzed against both negative controls (Negative Control #1 and Negative Control #1, obtained from Ambion) and identified as microRNAs that significantly improved placental stem cell metabolic activity/cell and/or mitochondrial membrane potential/cell vs. either negative control ($p<0.05$, Student's t-Test).

6.1.1.3 Bioinformatic Target Gene Prediction/Pathway Analysis

A database consolidating of ten microRNA prediction databases was utilized to generate the predicted target genes of the confirmed microRNA hits from the library screen. This database consisted of prediction algorithms from Diana-microT, miRDB, miRTar, miRanda, miRBase, picTar, Targetscan, TarBase, miRecords, and miRTarBase. The pathway analysis and biological function information of predicted target genes were completed using Ingenuity Pathway Analysis (IPA) (Ingenuity Systems).

6.1.1.4 MicroRNA and Target Gene Validation Studies with PCR

For MicroRNA/target gene validation studies, placental stem cells were transfected with microRNA library screen confirmed hits, as described above but without insult, and microRNA and mRNA were isolated using the MiRvana microRNA Isolation Kit (Ambion). Serum starvation (culture in DMEM) and contact inhibition (doubling the cell seeding number) were conditions included in the study as positive cell cycle arrest controls to compare with microRNA gene modification.

For microRNA transfection assessment, RT-PCR was completed using Taqman MicroRNA Reverse Transcription Kit and Taqman MicroRNA Assays (Life Technologies) specific for each transfected microRNA mimic. PCR was completed using the Taqman MicroRNA Assays with Taqman 2× Universal PCR Master Mix with No AMPErase UNG (Life Technologies) and cDNA, and was run in standard mode on the Applied Biosystems 7900HT Fast Real-Time PCR Instrument. All data was analyzed in RQ Manager (Applied Biosystems).

To assess mRNA/target gene expression, RT-PCR was completed using the Superscript VILO Master Mix (Life Technologies). PCR was completed using Taqman Gene Expression Assays (Life Technologies) specific for predicted target genes, Taqman Fast Universal PCR Master Mix (Life Technologies), and cDNA, and was run on the Applied Biosystems 7900HT Fast Real-Time PCR Instrument in fast mode. All data was analyzed in RQ Manager (Applied Biosystems).

6.1.1.5 MicroRNA Cell Cycle Validation

A microRNA cell cycle validation study was completed to test whether microRNA cell survival hits induce a state of cellular quiescence in placental stem cells that protects the cells against insult.

Placental stem cells were seeded and transfected with microRNA cell survival hits as described above, but without 100% Rat Serum insult. Cells were then harvested and stained with the BrdU Flow Kit (BD Pharmingen), as per manufacturer's protocol, for cell cycle distribution analysis.

In addition, placental stem cells were evaluated for the effects of the microRNA cell survival hits on the expression of key cell cycle proteins, using antibodies against human CDK6, Cyclin D1 (CCND1), Cyclin D3 (CCND3), and Cyclin E (CCNE1) proteins. Standard techniques were used for CDK6 and CCND1.

For Cyclin D3 staining, cells were fixed with 1% Formaldehyde for 15 minutes at 4° C., followed by incubation with cold 75% Ethanol for a minimum of 2 hours at −20° C. Cells were permeabilized with cold 0.25% Triton X-100 for 5 minutes at 4° C., washed with 1% FBS-PBS, and incubated with FcR Blocking Reagent (Miltenyi Biotec) for 10 minutes at 4° C. Placental stem cells were then stained with 2.5× manufacturer's recommended staining concentration of Mouse anti-Human Cyclin D3 Fitc antibody (BD Pharmingen), with matched concentration of Mouse IgG1 Isotype control (BD Pharmingen), and stained for 30 minutes at room temperature and in the dark. Data was acquired using a FACS Canto II Flow Cytometer (BD Biosciences) and analyzed in FlowJo (Tree Star).

For Cyclin E staining, cells were fixed with 4% Paraformaldehyde for 15 minutes at 4° C., and permeabilized with cold 0.1% Tween-20 for 20 minutes at 4° C. Cells were washed with 1% FBS-PBS, and incubated with FcR Blocking Reagent (Miltenyi Biotec) for 10 minutes at 4° C. Placental stem cells were then stained for 30 minutes at room temperature with 2.5× manufacturer's recommended staining concentration of Mouse anti-Human Cyclin E antibody (Abcam), with matched concentration of Mouse IgG1 Isotype control (Abcam), followed by secondary staining with Goat Polyclonal Secondary to Mouse IgG Dylight 488(Abcam) for 30 minutes at room temperature. Data was acquired using a FACS Canto II Flow Cytometer (BD Biosciences) and analyzed in FlowJo (Tree Star).

6.1.2 Results 6.1.2.1 MicroRNA Library Screen

The screening of 1,090 microRNAs for augmentation of placental stem cell survival upon exposure to 100% Rat Serum insult resulted in diverse effects caspase 3/7 activity/cell in placental stem cells.

Several transfected microRNAs lowered caspase 3/7 activity/cell post-insult. As shown in Table 3, a total of 36 microRNA hits significantly decreased caspase 3/7 activity/cell post insult, as compared to either of the negative controls provided in the assay kit. Modulation ranged from a decrease of −7.23% to −34.44% in caspase 3/7 activity/cell.

TABLE 3

List microRNA hits from the library screen for placental stem cell survival augmentation MicroRNA Library Screen for PDAC Cell Survival Augmentation Hits

| hsa-miR-424 | hsa-miR-141 | hsa-miR-3142 | hsa-miR-4310 | hsa-miR-1826 | hsa-miR-1308 |
| --- | --- | --- | --- | --- | --- |
| hsa-miR-143 | hsa-miR-581 | hsa-miR-1201 | hsa-miR-1203 | hsa-miR-3158 | hsa-miR-1227 |
| hsa-miR-136 | hsa-miR-362-5p | hsa-miR-4305 | hsa-miR-1271 | hsa-miR-1236 | hsa-miR-369-5p |
| hsa-miR-662 | hsa-miR-613 | hsa-miR-126* | hsa-miR-3123 | hsa-miR-432 | hsa-miR-450b-5p |
| hsa-miR-432* | hsa-miR-611 | hsa-miR-591 | hsa-miR-631 | hsa-miR-3170 | hsa-miR-548k |
| hsa-miR-16 | hsa-miR-199a-5p | hsa-miR-521 | hsa-miR-301a | hsa-miR-514b-5p | hsa-miR-29a |

6.1.2.2 Metabolic Activity and Mitochondrial Membrane Potential Studies

Each of microRNA MiR-16, miR-29a, miR-424, miR-4305, miR-3142, and miR-613 were determined to cause a statistically significant decrease in caspase 3/7 activity/cell post insult as compared to the negative controls (FIG. 1).

Figure 2:
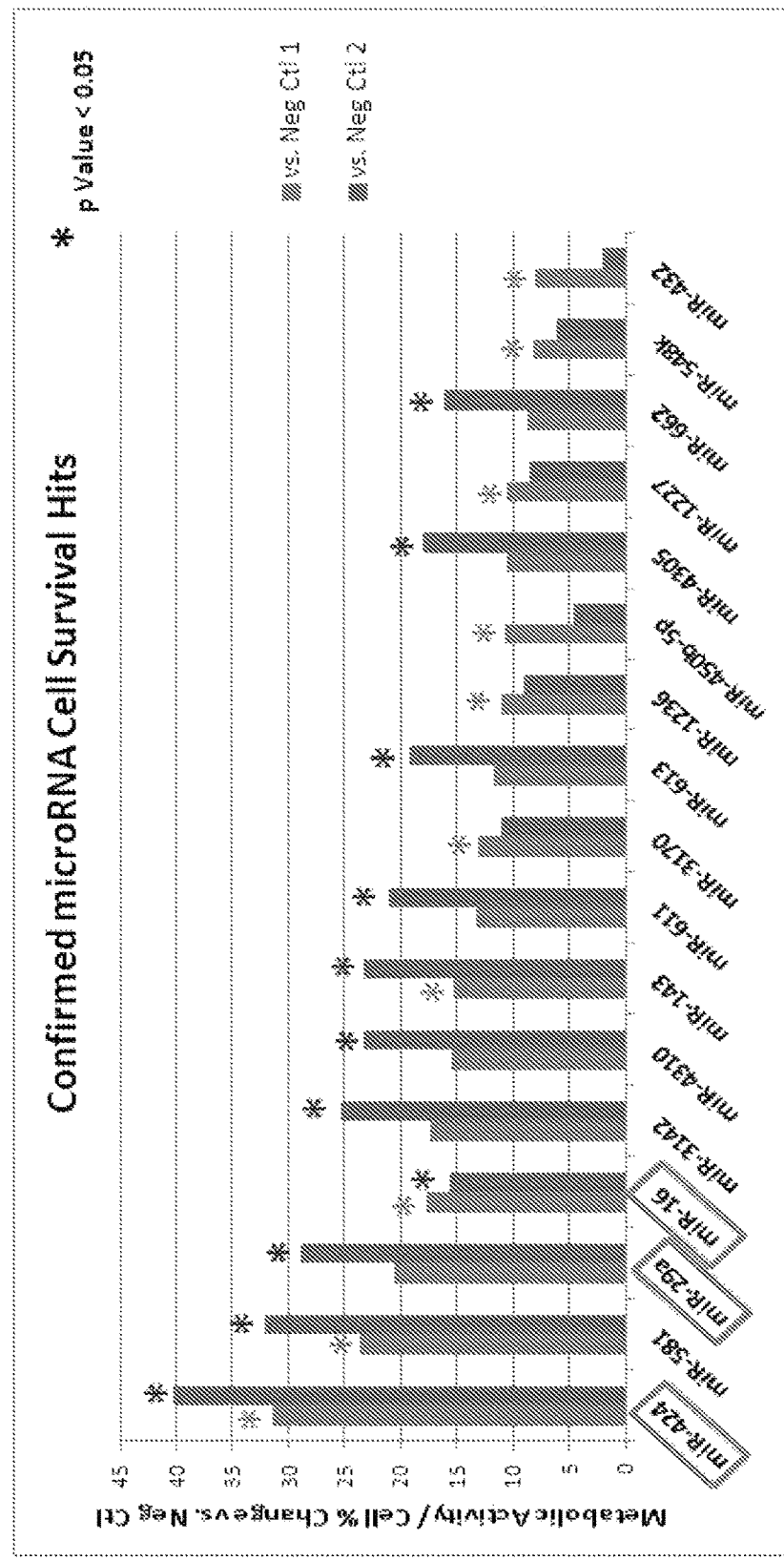
FIG. 2 depicts metabolic activity of placental stem cells transfected with different microRNAs as compared to metabolic activity of placental stem cells transfected with negative controls.
Figure 3:
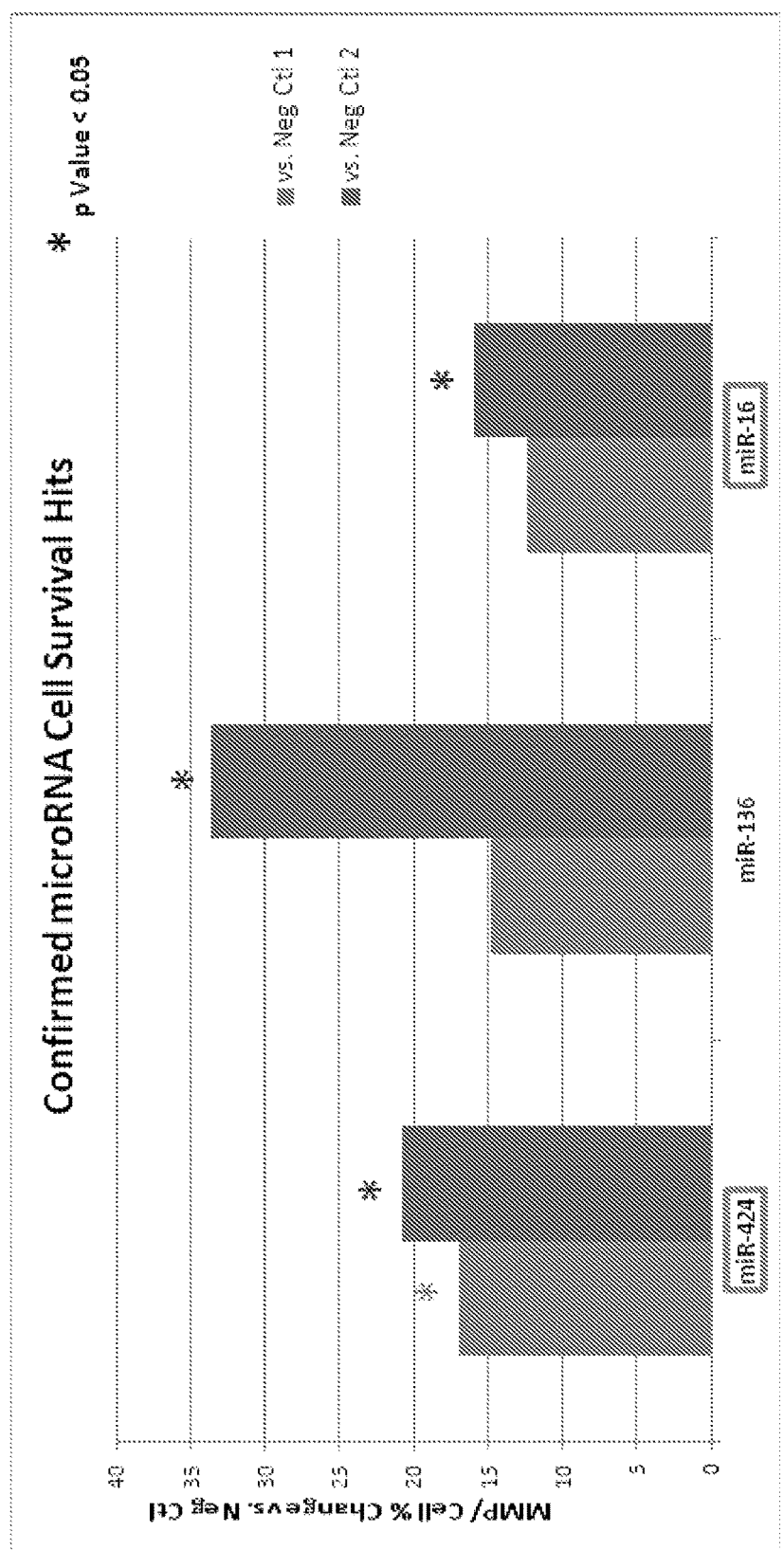
FIG. 3 depicts mitochondrial membrane potential of placental stem cells transfected with different microRNAs as compared to mitochondrial membrane potential of placental stem cells transfected with negative controls.

Each of these microRNA hits was also found to increase placental stem cell metabolic activity/cell post insult (FIG. 2). Of the six confirmed hits, miR-16 and miR-424 also increased placental stem cell mitochondrial membrane potential/cell (FIG. 3), further confirming cell survival augmentation.

The top confirmed caspase 3/7 modulators, miR-16, miR-424, and miR-29a, were found to share similar seed sequences that bind to their target mRNA, i.e., the 5' sequence of miRNA important to function of the miRNA (based on its complementarity to the nucleic acid sequence of the target mRNA). MiR-16 and miR-424 have identical seed sequences, while miR-29a varies by one nucleotide in the 5th position (Table 4). Accordingly, it was expected that these microRNA target and modulate a similar subset of target genes and pathways/biological functions.

TABLE 4

Seed sequence similarity between microRNA (seed sequences as present in the mature miRNA are boxed)
Confirmed Cell Survival miR Hits

| miRNA Mature Name(s) | Ambion_miProd_ID | Mature_Sequence | Confirmation Screens: Change in Caspase Activity |
|---|---|---|---|
| hsa-miR-16 | PM10339 | U|AGCAGCA|CGUAAAUAUUGGCG | 21-23% Decrease |
| hsa-miR-424 | PM10306 | C|AGCAGCA|AUUCAUGUUUUGAA | 12-14% Decrease |
| hsa-miR-29a | PM12499 | U|AGCACCA|UCUGAAAUCGGUUA | 17-20% Decrease |
| hsa-miR-613 | PM11528 | AGGAAUGUUCCUUCUUUGCC | 4% Decrease |
| hsa-miR-3142 | PM18673 | AAGGCCUUUCUGAACCUUCAGA | 6% Decrease |
| hsa-miR-4305 | PM18703 | CCUAGACACCUCCAGUUC | 8% Decrease |

6.1.2.3 Target Gene Prediction/Pathway Analysis

Bioinformatic analysis of miR-29a, miR-16, and miR-424 identified a total of 150 experimentally validated genes that were predicted to be targeted by these microRNAs. Prediction analysis of miR-29a resulted in 26 target genes, analysis of miR-16 predicted 105 target genes, while analysis of miR-424 resulted in 19 genes (Table 5).

TABLE 5

MicroRNA target gene prediction of experimentally validated genes for miR-29a, miR-16, and miR-424

Experimentally Validated Genes
(Number in parentheses denotes # of predicted databases)

| hsa-miR-29a | hsa-miR-16 | | | | hsa-miR-424 |
|---|---|---|---|---|---|
| ADAMTS9 (5) | ABCF2 (2) | DNAJB4 (3) | MYB (5) | RTN4 (2) | ANLN (1) |
| BACE1 (3) | ABHD10 (1) | EGFR (1) | NAA15 (3) | SEC24A (1) | CCND1 (3) |
| BCL2 (1) | ACTR1A (2) | EIF4E (2) | NAA25 (2) | SHOC2 (4) | CCND3 (2) |
| CAV2 (3) | ACVR2A (5) | EPT1 (3) | NAPG (2) | SLC12A2 (4) | CCNE1 (5) |
| CD276 (3) | ADSS (1) | FGF2 (3) | NOB1 (2) | SLC16A3 (1) | CCNF (1) |
| CDC42 (2) | ALG3 (1) | FNDC3B (2) | NOTCH2 (1) | SLC25A22 (1) | CDC14A (1) |
| CDK6 (3) | ARHGDIA (3) | GALNT7 (1) | PAFAH1B2 (3) | SLC38A5 (1) | CDC25A (5) |
| COL3A1 (5) | ARL2 (3) | GPAM (1) | PDCD4 (4) | SLC7A1 (1) | CDK6 (2) |
| COL4A1 (4) | ATG9A (3) | HACE1 (1) | PDCD6IP (2) | SNX15 (1) | CHEK1 (4) |
| COL4A2 (2) | BCL2 (3) | HARS (1) | PHKB (1) | SPTLC1 (3) | CUL2 (7) |
| CPEB3 (2) | C9ORF167 (1) | HARS2 (1) | PISD (2) | SQSTM1 (1) | FGFR1 (6) |
| CXXC6 (1) | C9ORF89 (2) | HERC6 (1) | PLK1 (1) | SRPR (5) | ITPR1 (6) |
| DIABLO (1) | CACNA2D1 (1) | HMGA1 (4) | PNN (1) | SRPRB (2) | KIF23 (5) |
| DNMT3A (5) | CAPRIN1 (2) | HSDL2 (1) | PNPLA6 (3) | TMEM43 (1) | MAP2K1 (5) |
| DNMT3B (3) | CCDC109A (1) | IGF2R (2) | PPIF (1) | TNFSF9 (1) | MYB (7) |
| FGA (1) | CCND1 (3) | IPO4 (1) | PPM1D (4) | TOMM34 (2) | PIAS1 (1) |
| IMPDH1 (2) | CCND3 (2) | ITGA2 (3) | PPP2R5C (3) | TPM3 (2) | PLAG1 (5) |
| INSIG1 (3) | CCNE1 (5) | KCNN4 (3) | PSAT1 (2) | TPPP3 (2) | SIAH1 (5) |
| KREMEN2 (2) | CCNT2 (6) | KPNA3 (2) | PTCD3 (1) | UBE2V1 (1) | WEE1 (6) |
| LPL (3) | CDC14B (2) | LAMC1 (1) | PTGS2 (1) | UBE4A (1) | |
| MCL1 (1) | CDK5RAP1 (1) | LAMTOR3 (1) | PURA (4) | UGDH (1) | |
| PIK3R1 (4) | CDK6 (1) | LUZP1 (3) | RAB9B (2) | UTP15 (1) | |
| PPM1D (4) | CENPJ (1) | LYPLA2 (2) | RAD51C (1) | VEGFA (4) | |
| SPARC (3) | CHORDC1 (3) | MCL1 (1) | RARS (1) | WNT3A (5) | |
| TET1 (4) | CREBL2 (1) | MLLT1 (1) | RECK (5) | WT1 (2) | |
| TRIM63 (3) | CSHL1 (1) | MMS19 (2) | RNASEL (1) | YIF1B (1) | |
| | | | | ZNF622 (3) | |
| 26 | 105 | | | | 19 |

150 TOTAL

Several of the experimentally validated genes were predicted to be targeted by two or more microRNA hits (Tables 5 and 6). These predicted genes included genes related to apoptosis, cell cycle regulation, transcription activation, and the cell stress response pathway.

TABLE 6

List and function of experimentally validated genes predicted to be targeted by two or more confirmed placental stem cell survival augmenting microRNA hits Genes targeted by >2 miRs
(Number in parentheses denotes # of mirs)

| | | |
|---|---|---|
| miR-29a, miR-16 | BCL2 (2) | B-cell lymphoma 2; Apoptosis Regulator: Anti-apoptotic; Implicated in a number of Cancers |
| miR-16, miR-424 | CCND1 (2) | Cyclin D1; Forms a complex with CDK4 and CDK6 and initiates G1/S phase cell cycle transition; Over expressed in a variety of tumors |
| miR-16, miR-424 | CCND3 (2) | Cyclin D3; Forms a complex with CDK4 and CDK6 and initiates G1/S phase cell cycle transition |
| miR-16, miR-424 | CCNE1 (2) | Cyclin E1; Forms a complex with CDK2 and initiates G1/S phase cell cycle transition; Over expressed in a variety of tumors |
| miR-29a, miR-16, miR-424 | CDK6 (3) | Cyclin-Dependent Kinase 6; Associates with Cyclin D to initiate G1/S phase cell cycle transition/progression |
| miR-29a, miR-16 | MCL1 (2) | Induced Myeloid Leukemia Cell Differentiation Protein; Alternative splicing of gene can result in a gene product that either inhibits or promotes apoptosis |
| miR-16, miR-424 | MYB (2) | Myeloblastosis Proto-Oncogene Protein/ Transcriptional Activator; Transcription Factor; Plays a role in the regulation of hematopoiesis and tumorigenesis |
| miR-29a, miR-16 | PPM1D (2) | Protein phosphatase 1D; Ser/Thr protein phosphatase; Negative regulator of cell stress response pathways; Reduces p53-mediated transcription and stress induced apoptosis; Plays a role in Cancer development |

6.1.2.4 MicroRNA and Target Gene Validation Studies with PCR

Figure 4A:
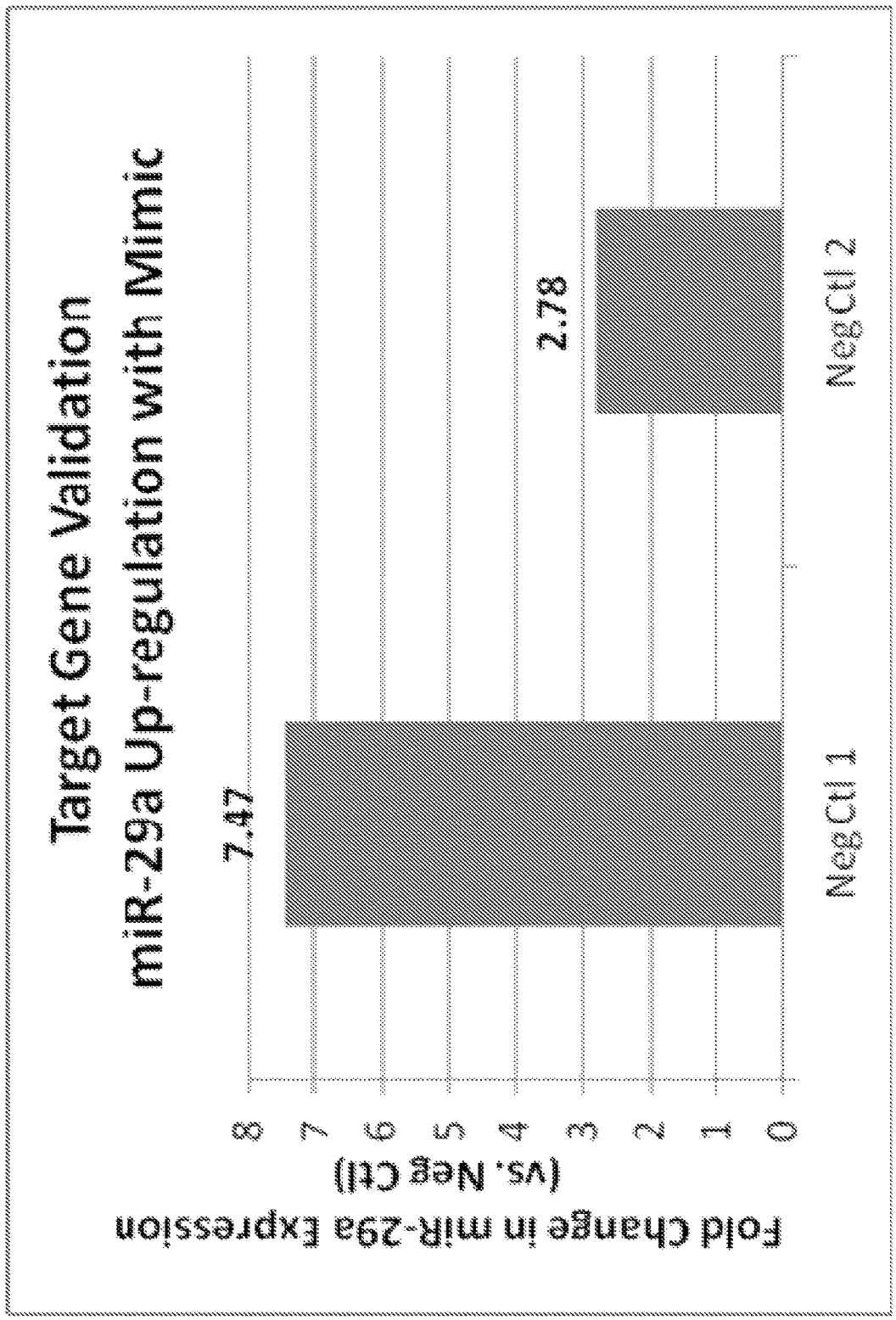
FIG. 4A, FIG. 4B and FIG. 4C depict expression levels of: miR-29A (FIG. 4A), miR-16 (FIG. 4B), and miR-424 (FIG. 4C) in placental stem cells transfected with the different miRs as compared to levels observed when placental stem cells were transfected with negative controls.
Figure 4B:
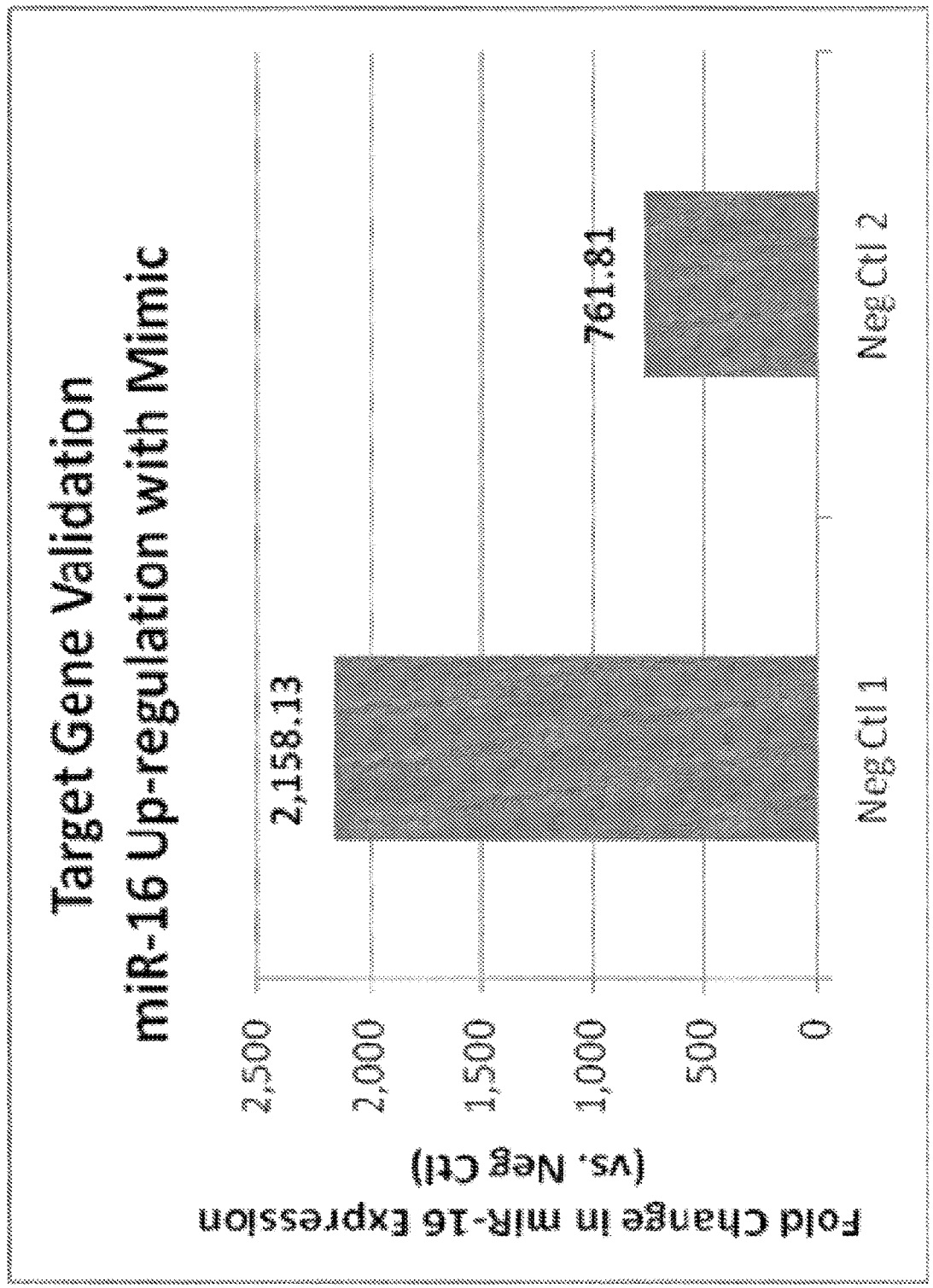
Figure 4C:
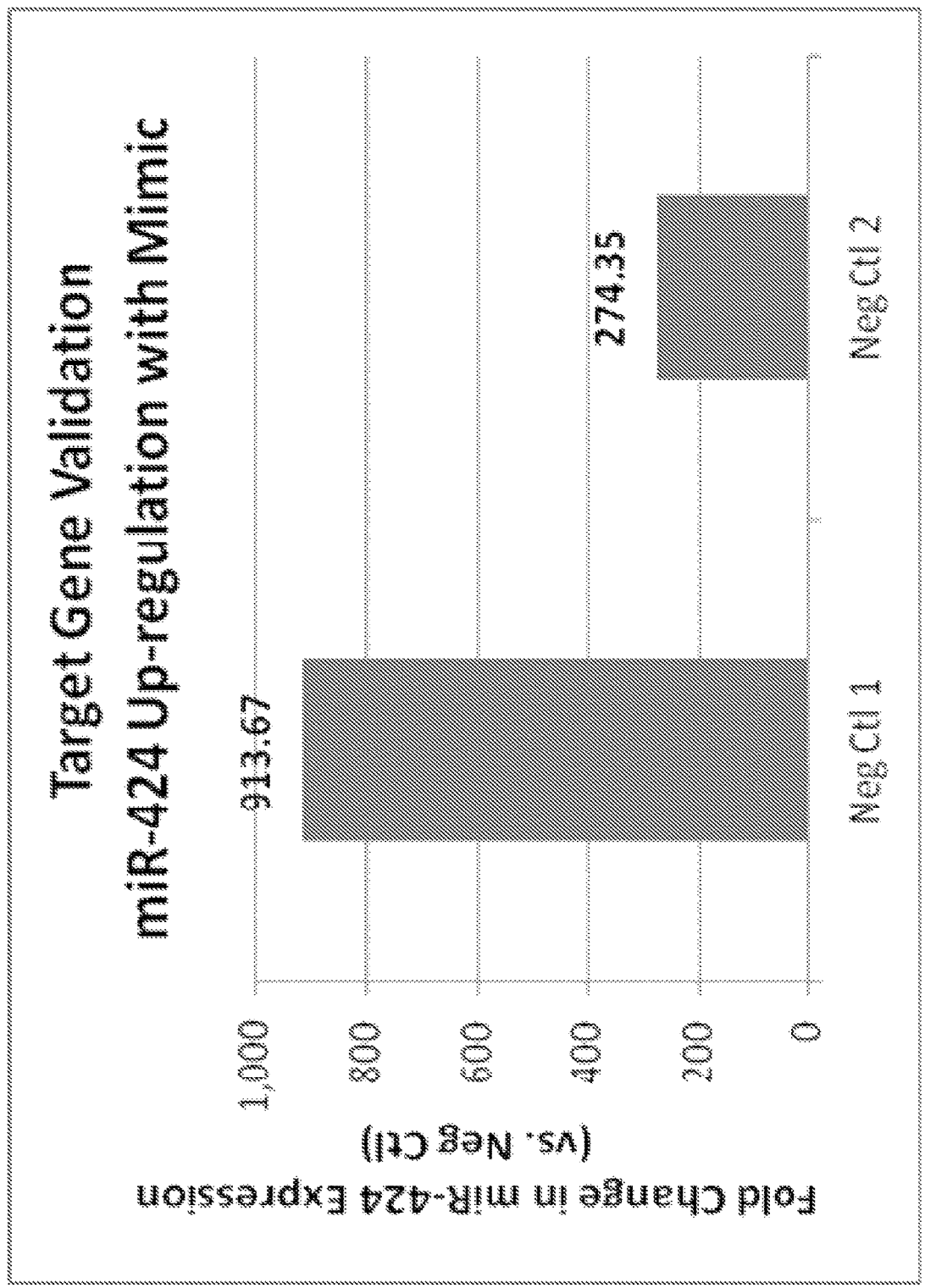

MicroRNA validation studies using qPCR confirmed successful transfection of placental stem cells with microRNA mimics prior to insult. Transfection of placental stem cells with miR-29a resulted in a 2.78-7.47 fold increase in miR-29a expression (FIG. 4A), transfection with miR-16 resulted in a 762-2,158 fold increase in miR-16 expression (FIG. 4B), and transfection with miR-424 resulted in a 274-914 fold increase in miR-424 expression (FIG. 4C).

Gene expression studies validated and confirmed numerous genes predicted to be targeted by the microRNA hits in the bioinformatic studies. All of the experimentally validated genes that were predicted to be targeted by two or more microRNA hits (italicized) were confirmed to be targeted and modulated by the microRNA hits within the gene expression studies.

miR-16 and miR424 had similar target gene modulation patterns that were consistent with serum starvation and contact inhibition condition signatures, but distinct from miR-29a. MiR-16 and miR-424 both down-regulated genes related to cell cycle progression (CCND1, CCND3, CCNE1, CCNF, and CDK6), cell cycle regulation (CDC25A, WEE1, and CHEK1) and transcription activation (MyB). MiR-16 and miR-424 up-regulated negative regulators of cell growth and division (PPP2R5C), inhibitors of apoptosis (MCL1), negative regulators of cell stress pathway/p53 (PPM1D and HMGA1), as well as genes related to cell survival signaling (AKT3 and VEGFA) and adhesion (ITGA2). These molecular changes, taken together and compared to changes resulting from serum starvation and contact inhibition, suggest a role of cell cycle arrest as a mechanism for placental stem cell survival augmentation with miR-16 and miR-424.

miR-29a up-regulated CCND1, CCND3, CCNE1, CDC25A, WEE1 gene expression, and down-regulated MCL1, PPMID, HMGA1, AKT3, VEGFA, and ITGA2 gene expression, implicating a slightly different underlying mechanism for cell survival augmentation for this microRNA.

The molecular changes observed in the target gene validation studies indicate that these miR treatments induce a state of quiescence in placental stem cells that is protective against insult, and augments cell survival.

6.1.2.5 MicroRNA Cell Cycle Validation

Figure 5A:
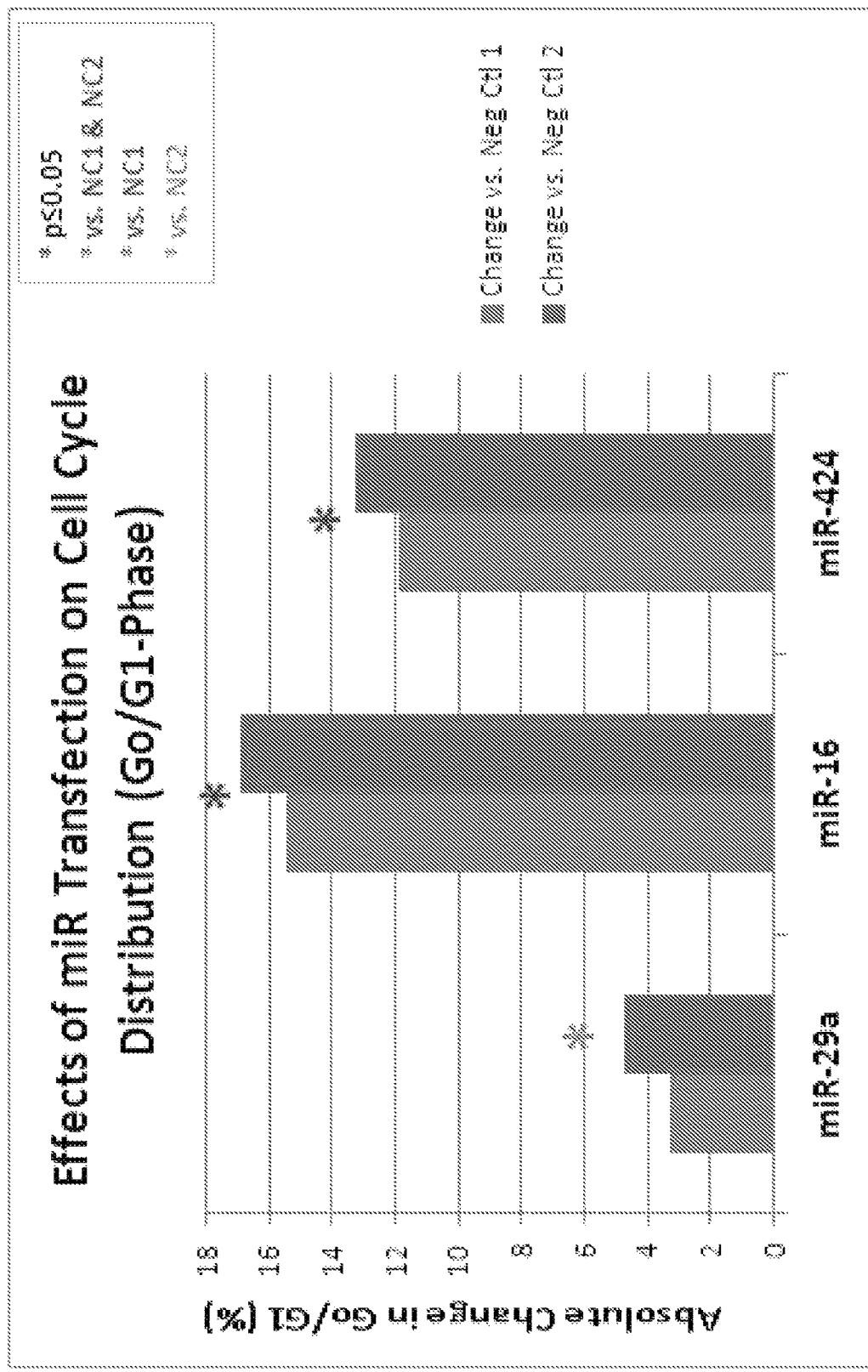
FIG. 5A, FIG. 5B and FIG. 5C depict the effect of miR-29A, miR-16, and miR-424 transfection on the cell cycle distribution of placental stem cells.
Figure 5B:
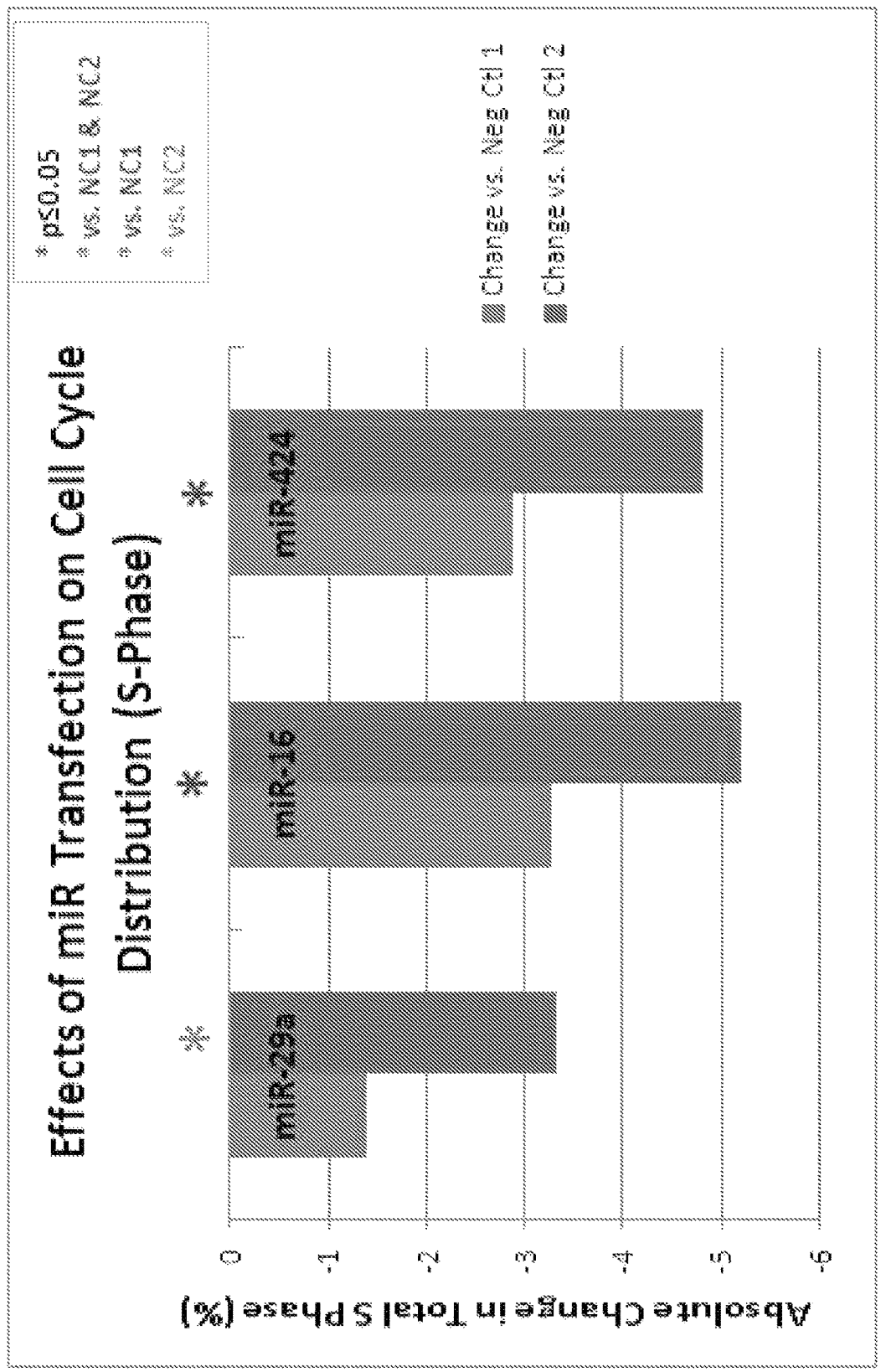
Figure 5C:
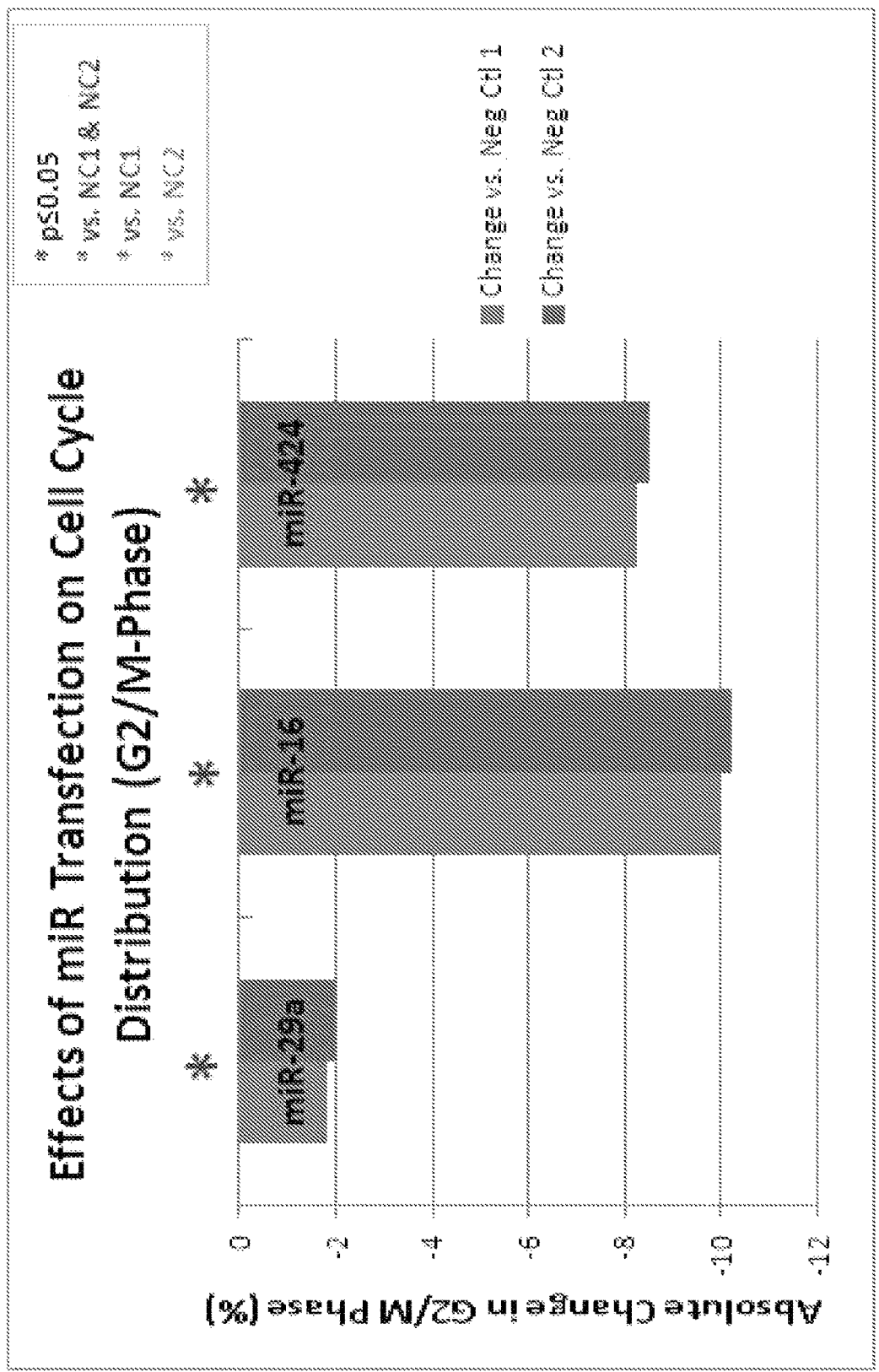

Placental stem cell microRNA cell cycle validation studies, using BrdU, confirmed that the microRNA cell survival hits described above induce a state of cellular quiescence in placental stem cells that is protective against insult. Transfection of placental stem cells with miR-29a resulted in a 3.32% to 4.77% absolute increase in the distribution of cells in the G0/G1-phase (FIG. 5A), a −1.4% to −3.32% absolute decrease in the distribution of cells in the S-phase (FIG. 5B), and a −1.8% to −2.05% absolute decrease in the distribution of cells in the G2/M-phase of the cell cycle (FIG. 5C). Transfection with miR-16 resulted in a 15.45% to 16.9% absolute increase in the distribution of cells in the G0/G1-phase (FIG. 5A), a −3.27% to −5.2% absolute decrease in the distribution of cells in the S-phase (FIG. 5B), and a −9.99% to −10.24% absolute decrease in the distribution of cells in the G2/M-phase of the cell cycle (FIG. 5C). Transfection with miR-424 resulted in a 11.85% to 13.3% absolute increase in the distribution of cells in the G0/G1-phase (FIG. 5A), a −2.88% to −4.81% absolute decrease in the distribution of cells in the S-phase (FIG. 5B), and a −8.27% to −8.52% absolute decrease in the distribution of cells in the G2/M-phase of the cell cycle (FIG. 5C).

Flow cytometric evaluation further validated Cyclin D3 and Cyclin E as targets of miR-16 and miR-424. Transfection with miR-16 resulted in a −29.55% to −35.25% absolute decrease in placental stem cell Cyclin D3 expression (FIG. 6A), and a −20.75% to −23.2% absolute decrease in placental stem cell Cyclin E expression (FIG. 6B). Transfection with miR-424 resulted in a −20.25% to −25.95% absolute decrease in placental stem cell Cyclin D3 expression (FIG. 6A), and a −11.15% to −13.6% absolute decrease in placental stem cell Cyclin E expression (FIG. 6B).

Figure 6A:
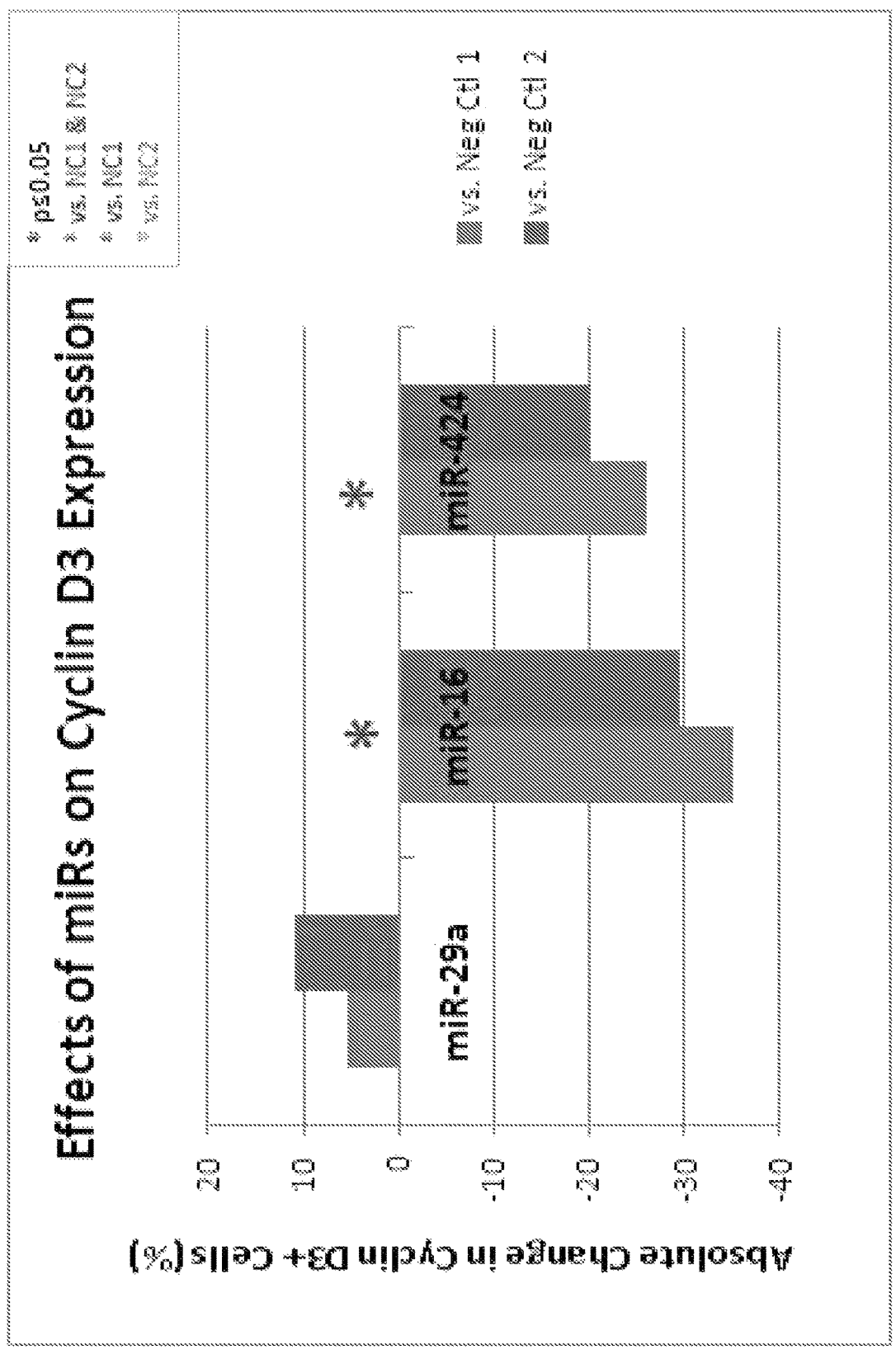
FIG. 6A and FIG. 6B depicts the effect of miR-29A, miR-16, and miR-424 on placental stem cell expression of Cyclin D3 (FIG. 6A) and Cyclin E (FIG. 6B).
Figure 6B:
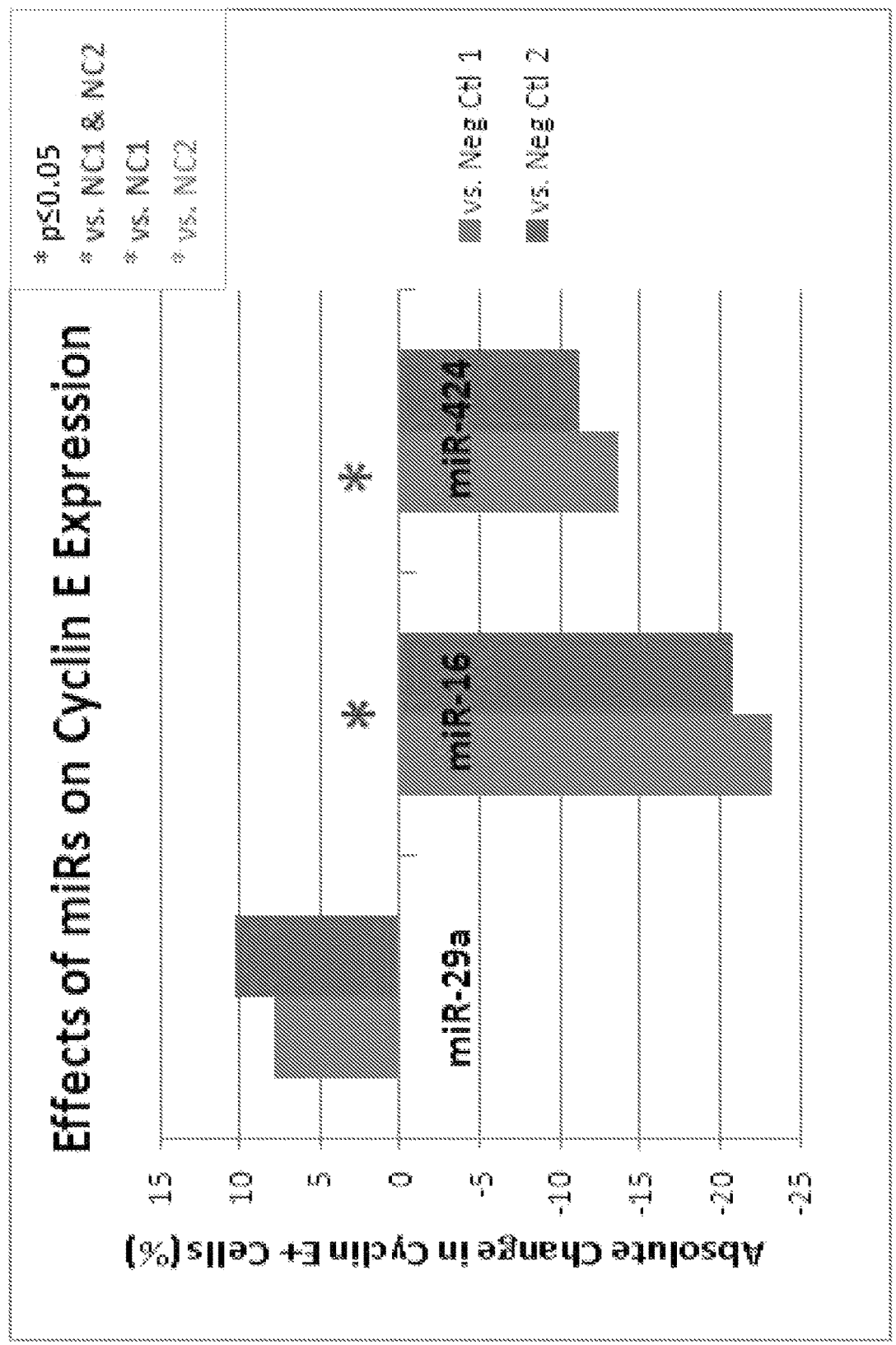

Transfection of placental stem cells with miR-29a resulted in an up-regulation of Cyclin D3 and Cyclin E gene expression by the placental stem cells, as well as an increase in Cyclin D3 and Cyclin E protein expression (FIG. 6A-B). Without wishing to be bound by any particular theory or mechanism, based on the cell cycle studies described above, cell cycle arrest is the most likely mechanism of placental stem cell survival augmentation with miR-29a. However, these data indicate that the mechanism is not likely mediated by the targeting and down-regulation of Cyclins D3 and E, as in the case of miR-16 and miR-424.

These cell cycle validation studies further demonstrate that modulatory RNA, such as microRNA, can augment placental stem cell survival in the face of insult by targeting cell cycle related genes/proteins.

6.1.3 Conclusion microRNAs capable of augmenting placental stem cell survival in the presence of insult were identified and validated, as were the molecular targets and biological pathways/mechanisms linked to cell survival augmentation. The data indicate that targeting of the molecular targets and biological pathways/mechanisms results in induction of quiescence in the placental stem cells with enhanced survival capability. Modulation of microRNAs and their targeted genes/pathways (e.g., through mechanisms other than use of microRNA) represents a novel means by which enhanced placental stem cells capable of surviving under suboptimal conditions, or surviving for longer durations of time under normal culture/in vivo conditions, can be generated.

Equivalents

The compositions and methods disclosed herein are not to be limited in scope by the specific embodiments described herein. Indeed, various modifications of the compositions and methods in addition to those described will become apparent to those skilled in the art from the foregoing description and accompanying figures. Such modifications are intended to fall within the scope of the appended claims.

Various publications, patents and patent applications are cited herein, the disclosures of which are incorporated by reference in their entireties.

What is claimed is:

1. An isolated placental stem cell, wherein said placental stem cell has been modified to comprise or express miR-29a, and wherein said placental stem cell demonstrates increased survival relative to corresponding unmodified placental stem cells when cultured under one or more conditions that cause cell death.

2. The isolated placental stem cell of claim 1, wherein said placental stem cell expresses at least one survival-associated gene at a decreased level as compared to the expression of the same survival-associated gene in a corresponding unmodified placental stem cell.

3. The isolated placental stem cell of claim 2, wherein said survival-associated gene is ADAMTS9, BACE1, BCL2, CAV2, CD276, CDC42, CDK6, COL3A1, COL4A1, COL4A2, CPEB3, TRIM63, CXXC6/TET1, DIABLO, DNMT3A, DNMT3B, FGA, IMPDH1, INSIG1, KREMEN2, LPL, MCL1, PIK3R1, PPM1D, SPARC.

4. The isolated placental stem cell of claim 1, wherein said miR-29a causes said placental cell to express Cyclin D3 and/or Cyclin E at an increased level as compared to a corresponding unmodified placental stem cell.

5. The isolated placental stem cell of claim 1, wherein said placental stem cell exhibits (i) decreased expression of caspase 3/7, (ii) increased mitochondrial membrane potential, and/or (iii) increased metabolic activity when cultured under one or more conditions that cause cell death as compared to corresponding unmodified placental stem cells cultured under the same condition(s).

6. An isolated population of cells, wherein at least 50% of the cells in said population are the cells of claim 1.

7. The isolated population of cells of claim 6, wherein at least 80% of the cells in said population of cells are the cells of claim 1.

8. The population of cells of claim 6, wherein said placental stem cells in said population are CD10$^+$, CD34$^-$, CD105$^+$, CD200$^+$placental stem cells.

9. A composition comprising the isolated placental stem cell of claim 1.

10. The placental stem cell of claim 1, wherein said placental stem cell is a CD10$^+$, CD34$^-$, CD105$^+$, CD200$^+$ placental stem cell.

11. The composition of claim 1, wherein said placental stem cells are CD10$^+$, CD34$^-$, CD105$^+$, CD200$^+$placental stem cells.

12. A method of producing placental stem cells that comprise or express miR-29a, wherein said placental stem cells demonstrate increased survival relative to corresponding unmodified placental stem cells when cultured under one or more conditions that cause cell death, said method comprising contacting a population of placental stem cells with an effective amount of miR-29a, such that said placental stem cells, after having been contacted with said miR-29a express Cyclin D3 and/or Cyclin E at an increased level as compared to a corresponding number of unmodified placental stem cells not contacted with said miR-29a.

13. An isolated placental stem cell or population thereof produced by the method of claim 12.

14. A composition comprising an isolated placental stem cell produced by the method of claim 12.

15. The method of claim 12, wherein said placental stem cells are CD10$^+$, CD34$^-$, CD105$^+$, CD200$^+$placental stem cells.

* * * * *

SEQUENCE LISTING

```
<160> NUMBER OF SEQ ID NOS: 6

<210> SEQ ID NO 1
<211> LENGTH: 22
<212> TYPE: RNA
<213> ORGANISM: Artificial Sequence
<220> FEATURE:
<223> OTHER INFORMATION: mature microRNA

<400> SEQUENCE: 1
uagcagcacg uaaauauugg cg                                              22

<210> SEQ ID NO 2
<211> LENGTH: 22
<212> TYPE: RNA
<213> ORGANISM: Artificial Sequence
<220> FEATURE:
<223> OTHER INFORMATION: mature microRNA

<400> SEQUENCE: 2
cagcagcaau ucauguuuug aa                                              22

<210> SEQ ID NO 3
<211> LENGTH: 22
<212> TYPE: RNA
<213> ORGANISM: Artificial Sequence
<220> FEATURE:
<223> OTHER INFORMATION: mature microRNA

<400> SEQUENCE: 3
uagcaccauc ugaaaucggu ua                                              22

<210> SEQ ID NO 4
<211> LENGTH: 20
<212> TYPE: RNA
<213> ORGANISM: Artificial Sequence
<220> FEATURE:
<223> OTHER INFORMATION: mature microRNA

<400> SEQUENCE: 4
aggaauguuc cuucuuugcc                                                 20

<210> SEQ ID NO 5
<211> LENGTH: 22
<212> TYPE: RNA
<213> ORGANISM: Artificial Sequence
<220> FEATURE:
<223> OTHER INFORMATION: mature microRNA

<400> SEQUENCE: 5
aaggccuuuc ugaaccuuca ga                                              22
```

```
<210> SEQ ID NO 6
<211> LENGTH: 18
<212> TYPE: RNA
<213> ORGANISM: Artificial Sequence
<220> FEATURE:
<223> OTHER INFORMATION: mature microRNA

<400> SEQUENCE: 6
ccuagacacc uccaguuc                                                  18
```